(12) United States Patent
Marban et al.

(10) Patent No.: US 11,872,251 B2
(45) Date of Patent: Jan. 16, 2024

(54) CARDIOSPHERE-DERIVED CELLS AND EXOSOMES SECRETED BY SUCH CELLS IN THE TREATMENT OF HEART FAILURE WITH PRESERVED EJECTION FRACTION

(71) Applicant: Cedars-Sinai Medical Center, Los Angeles, CA (US)

(72) Inventors: Eduardo Marban, Santa Monica, CA (US); Romain Gallet, Paris (FR)

(73) Assignee: Cedars-Sinai Medical Center, Los Angeles, CA (US)

( * ) Notice: Subject to any disclaimer, the term of this patent is extended or adjusted under 35 U.S.C. 154(b) by 114 days.

(21) Appl. No.: 17/469,441

(22) Filed: Sep. 8, 2021

(65) Prior Publication Data

US 2021/0401896 A1 Dec. 30, 2021

Related U.S. Application Data

(62) Division of application No. 16/066,014, filed as application No. PCT/US2017/013054 on Jan. 11, 2017, now Pat. No. 11,253,551.

(60) Provisional application No. 62/277,359, filed on Jan. 11, 2016.

(51) Int. Cl.
| | |
|---|---|
| *A61K 35/34* | (2015.01) |
| *C12N 5/077* | (2010.01) |
| *A61P 9/04* | (2006.01) |
| *A61K 9/00* | (2006.01) |

(52) U.S. Cl.
CPC ............ *A61K 35/34* (2013.01); *A61K 9/0019* (2013.01); *A61P 9/04* (2018.01); *C12N 5/0657* (2013.01)

(58) Field of Classification Search
None
See application file for complete search history.

(56) References Cited

U.S. PATENT DOCUMENTS

| | | | |
|---|---|---|---|
| 3,470,876 A | 10/1969 | Barchilon | |
| 3,964,468 A | 6/1976 | Schulz | |
| 4,106,488 A | 8/1978 | Gordon | |
| 4,659,839 A | 4/1987 | Nicolotti et al. | |
| 4,921,482 A | 5/1990 | Hammerslag et al. | |
| 4,960,134 A | 10/1990 | Webster, Jr. | |
| 5,028,588 A | 7/1991 | Hoffman et al. | |
| 5,052,402 A | 10/1991 | Bencini et al. | |
| 5,104,787 A | 4/1992 | Lindstrom et al. | |
| 5,175,004 A | 12/1992 | Matsumura | |
| 5,199,950 A | 4/1993 | Schmitt | |
| 5,228,441 A | 7/1993 | Lundquist | |
| 5,243,167 A | 9/1993 | Lundquist | |
| 5,287,857 A | 2/1994 | Mann | |
| 5,315,996 A | 5/1994 | Lundquist | |
| 5,322,064 A | 6/1994 | Lundquist | |
| 5,329,923 A | 7/1994 | Lundquist | |
| 5,334,145 A | 8/1994 | Lundquist et al. | |
| 5,383,852 A | 1/1995 | Stevens-Wright | |
| 5,436,128 A | 7/1995 | Harpold et al. | |
| 5,454,787 A | 10/1995 | Lundquist | |
| 5,477,856 A | 12/1995 | Lundquist | |
| 5,492,825 A | 2/1996 | Jan et al. | |
| 5,507,725 A | 4/1996 | Savage et al. | |
| 5,616,568 A | 4/1997 | Prestwich et al. | |
| 5,618,294 A | 4/1997 | Aust et al. | |
| 5,670,335 A | 9/1997 | Jan et al. | |
| 5,685,868 A | 11/1997 | Lundquist | |
| 5,702,433 A | 12/1997 | Taylor et al. | |
| 5,702,905 A | 12/1997 | Takahashi et al. | |
| 5,762,069 A | 6/1998 | Kelleher et al. | |
| 5,782,748 A | 7/1998 | Palmer et al. | |
| 5,824,031 A | 10/1998 | Cookston et al. | |
| 5,840,502 A | 11/1998 | Van Vlasselaer | |
| 5,851,212 A | 12/1998 | Zirps et al. | |
| 5,856,155 A | 1/1999 | Li | |
| 5,872,109 A | 2/1999 | Akima et al. | |

(Continued)

FOREIGN PATENT DOCUMENTS

| | | |
|---|---|---|
| CA | 2488346 | 12/2003 |
| CN | 1537646 | 10/2004 |

(Continued)

OTHER PUBLICATIONS

Gallet et al. JACC 1(1):14-28, Jan. 1, 2016 (Year: 2016).*
Ibrahim et al. Stem Cell Reports 2:606-619, 2014 (Year: 2014).*
Takeda et al., "Induced Pluripotant Stem (IPS) Cell-Based Cell Therapy for Duchenne Muscular Dystrophy", History of Medicine, Dec. 31, 2011, vol. 239, No. 14, pp. 1440-1444.
Takehara, MD, PhD, et al., "Controlled Delivery of Basic Fibroblast Growth Factor Promotes Human Cardiosphere-Derived Cell Engraftment to Enhance Cardiac Repair for Chronic Myocardial Infarction" Journal of the American College of Cardiology, 2008, vol. 52, No. 23, pp. 1858-1865.
Takeshita et al. "Osteoblast-Specific Factor 2: Cloning of a Putative Bone Adhesion Protein with Homology with the Insect Protein Fasciclin I", Biochemical Journal, 1993, vol. 294, pp. 271-278.

(Continued)

*Primary Examiner* — Marcia S Noble
(74) *Attorney, Agent, or Firm* — Knobbe, Martens, Olson & Bear, LLP

(57) ABSTRACT

Heart failure with preserved ejection fraction (HFpEF) is a disease condition characterized by heart failure (HF) signs and symptoms, but with normal or near normal left ventricular ejection fraction (LVEF) and is not responsive to standard therapy for treatment of HF. Described herein are compositions and methods related to use of cardiosphere derived cells (CDCs) and their exosomes to improve left ventricular structure, function and overall outcome. Administration of CDCs led to improved LV relaxation, lower LV end-diastolic pressure, decreased lung congestion and enhanced survival. Lower risk of arrhythmias in HFpEF was also observed following CDC administration. Improvement of diastolic dysfunction following administration of CDC-derived exosomes was observed, along with decreased mortality. In view of these salutary effects, CDCs and CDC-derived exosomes are beneficial in the treatment of HFpEF.

7 Claims, 42 Drawing Sheets

(56) References Cited

U.S. PATENT DOCUMENTS

| | | |
|---|---|---|
| 5,874,417 A | 2/1999 | Prestwich et al. |
| 5,938,603 A | 8/1999 | Ponzi |
| 5,955,275 A | 9/1999 | Kamb |
| 5,957,863 A | 9/1999 | Koblish et al. |
| 5,981,165 A | 11/1999 | Weiss et al. |
| 6,004,295 A | 12/1999 | Langer et al. |
| 6,074,408 A | 6/2000 | Freeman |
| 6,077,287 A | 6/2000 | Taylor et al. |
| 6,086,582 A | 7/2000 | Altman et al. |
| 6,099,832 A | 8/2000 | Mickle et al. |
| 6,102,887 A | 8/2000 | Altman |
| 6,132,390 A | 10/2000 | Cookston et al. |
| 6,153,582 A | 11/2000 | Skelnik |
| 6,165,164 A | 12/2000 | Hill et al. |
| 6,193,763 B1 | 2/2001 | Mackin |
| 6,203,487 B1 | 3/2001 | Consigny |
| 6,224,587 B1 | 5/2001 | Gibson |
| 6,296,630 B1 | 10/2001 | Altman et al. |
| RE37,463 E | 12/2001 | Altman |
| 6,326,198 B1 | 12/2001 | Emerson et al. |
| 6,337,387 B1 | 1/2002 | Sakano et al. |
| 6,338,942 B2 | 1/2002 | Kraus et al. |
| 6,346,099 B1 | 2/2002 | Altman |
| 6,358,247 B1 | 3/2002 | Altman et al. |
| 6,361,997 B1 | 3/2002 | Huss |
| 6,387,369 B1 | 5/2002 | Pittenger et al. |
| 6,408,203 B2 | 6/2002 | Mackin |
| 6,416,510 B1 | 7/2002 | Altman et al. |
| 6,443,949 B2 | 9/2002 | Altman |
| 6,478,776 B1 | 11/2002 | Rosenman et al. |
| 6,488,659 B1 | 12/2002 | Rosenman |
| 6,500,167 B1 | 12/2002 | Webster, Jr. |
| 6,511,471 B2 | 1/2003 | Rosenman et al. |
| 6,511,477 B2 | 1/2003 | Altman et al. |
| 6,514,481 B1 | 2/2003 | Prasad et al. |
| 6,530,944 B2 | 3/2003 | West et al. |
| 6,540,725 B1 | 4/2003 | Ponzi |
| 6,547,787 B1 | 4/2003 | Altman et al. |
| 6,569,144 B2 | 5/2003 | Altman |
| 6,572,611 B1 | 6/2003 | Falwell |
| 6,577,895 B1 | 6/2003 | Altman |
| 6,585,716 B2 | 7/2003 | Altman |
| 6,716,242 B1 | 4/2004 | Altman |
| 6,726,654 B2 | 4/2004 | Rosenman |
| 6,726,662 B2 | 4/2004 | Altman |
| 6,739,342 B1 | 5/2004 | Fredriksson et al. |
| 6,783,510 B1 | 8/2004 | Gibson et al. |
| 6,796,963 B2 | 9/2004 | Carpenter et al. |
| 6,805,860 B1 | 10/2004 | Alt |
| 6,818,757 B2 | 11/2004 | Lee et al. |
| 6,866,117 B2 | 3/2005 | Moss et al. |
| 6,866,843 B2 | 3/2005 | Habener et al. |
| 6,905,827 B2 | 6/2005 | Wohlgemuth et al. |
| 6,925,327 B2 | 8/2005 | Altman |
| 6,971,998 B2 | 12/2005 | Rosenman et al. |
| 6,997,863 B2 | 2/2006 | Handy et al. |
| 7,026,121 B1 | 4/2006 | Wohlgemuth et al. |
| 7,029,466 B2 | 4/2006 | Altman |
| 7,034,008 B2 | 4/2006 | Donahue et al. |
| 7,037,648 B1 | 5/2006 | Marbán et al. |
| 7,048,711 B2 | 5/2006 | Rosenman et al. |
| 7,074,175 B2 | 7/2006 | Handy et al. |
| 7,104,988 B2 | 9/2006 | Altman et al. |
| 7,138,275 B2 | 11/2006 | Kremer et al. |
| 7,156,824 B2 | 1/2007 | Rosenman et al. |
| 7,220,582 B2 | 5/2007 | Epstein et al. |
| 7,259,011 B2 | 8/2007 | Lucas et al. |
| 7,280,863 B2 | 10/2007 | Shachar |
| 7,329,638 B2 | 2/2008 | Yang et al. |
| 7,351,237 B2 | 4/2008 | Altman |
| 7,402,151 B2 | 7/2008 | Rosenman et al. |
| 7,452,532 B2 | 11/2008 | Alt |
| 7,468,276 B2 | 12/2008 | Hariri |
| 7,470,425 B2 | 12/2008 | Vacanti et al. |
| 7,500,970 B2 | 3/2009 | Altman |
| 7,514,074 B2 | 4/2009 | Pittenger et al. |
| 7,517,686 B2 | 4/2009 | Kremer et al. |
| 7,531,354 B2 | 5/2009 | Stice et al. |
| 7,547,301 B2 | 6/2009 | Altman et al. |
| 7,547,674 B2 | 6/2009 | Anversa et al. |
| 7,553,663 B2 | 6/2009 | Kremer et al. |
| 7,592,177 B2 | 9/2009 | Chen et al. |
| 7,625,581 B2 | 12/2009 | Laredo et al. |
| 7,659,118 B2 | 2/2010 | Furcht et al. |
| 7,686,799 B2 | 3/2010 | Leonhardt et al. |
| 7,731,648 B2 | 6/2010 | Ivkov |
| 7,745,113 B2 | 6/2010 | Evans et al. |
| 7,794,702 B2 | 9/2010 | Rosen et al. |
| 7,837,631 B2 | 11/2010 | Diamond et al. |
| 7,862,810 B2 | 1/2011 | Anversa |
| 7,875,451 B2 | 1/2011 | Murray et al. |
| 7,971,592 B2 | 7/2011 | Ochi |
| 7,999,025 B2 | 8/2011 | Shumaker-Parry et al. |
| 8,008,254 B2 | 8/2011 | Anversa |
| 8,017,389 B2 | 9/2011 | Phillips et al. |
| 8,119,123 B2 | 2/2012 | Anversa et al. |
| 8,193,161 B2 | 6/2012 | Hosoda |
| 8,232,102 B2 | 7/2012 | Dobson et al. |
| 8,258,113 B2 | 9/2012 | Dimmeler et al. |
| 8,268,619 B2 | 9/2012 | Giacomello et al. |
| 8,562,972 B2 | 10/2013 | Edinger et al. |
| 8,772,030 B2 | 7/2014 | Giacomello et al. |
| 8,846,396 B2 | 9/2014 | Giacomello et al. |
| 8,945,558 B2 | 2/2015 | Kobara |
| 9,249,392 B2 | 2/2016 | Marbán et al. |
| 9,828,603 B2 | 11/2017 | Marbán et al. |
| 9,845,457 B2 | 12/2017 | Marbán et al. |
| 9,884,076 B2 | 2/2018 | Kreke et al. |
| 10,457,942 B2 | 10/2019 | Marbán et al. |
| 2001/0024824 A1 | 9/2001 | Moss et al. |
| 2002/0022259 A1 | 2/2002 | Lee et al. |
| 2002/0061587 A1 | 5/2002 | Anversa |
| 2002/0098167 A1 | 7/2002 | Anversa et al. |
| 2002/0155101 A1 | 10/2002 | Donahue et al. |
| 2002/0156383 A1 | 10/2002 | Altman et al. |
| 2002/0177772 A1 | 11/2002 | Altman et al. |
| 2003/0054973 A1 | 3/2003 | Anversa |
| 2003/0129221 A1 | 7/2003 | Semple et al. |
| 2003/0135113 A1 | 7/2003 | Altman et al. |
| 2003/0161817 A1 | 8/2003 | Young et al. |
| 2003/0195432 A1 | 10/2003 | Kortenbach et al. |
| 2003/0229386 A1 | 12/2003 | Rosenman et al. |
| 2004/0014209 A1 | 1/2004 | Lassar et al. |
| 2004/0018174 A1 | 1/2004 | Palasis |
| 2004/0030286 A1 | 2/2004 | Altman |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0102759 A1 | 5/2004 | Altman et al. |
| 2004/0110287 A1 | 6/2004 | Clarke et al. |
| 2004/0126879 A1 | 7/2004 | Schneider et al. |
| 2004/0136966 A1 | 7/2004 | Anversa et al. |
| 2004/0137621 A1 | 7/2004 | Rosen et al. |
| 2004/0153139 A1 | 8/2004 | Altman |
| 2004/0158313 A1 | 8/2004 | Altman |
| 2004/0168341 A1 | 9/2004 | Petersen et al. |
| 2004/0214182 A1 | 10/2004 | Sharma et al. |
| 2004/0254134 A1 | 12/2004 | Marbán et al. |
| 2005/0031854 A1 | 2/2005 | Lorenz et al. |
| 2005/0058630 A1 | 3/2005 | Harris et al. |
| 2005/0074880 A1 | 4/2005 | Sang et al. |
| 2005/0090732 A1 | 4/2005 | Ivkov |
| 2005/0176620 A1 | 8/2005 | Prestwich et al. |
| 2005/0214938 A1 | 9/2005 | Gold et al. |
| 2005/0215991 A1 | 9/2005 | Altman et al. |
| 2005/0255588 A1 | 11/2005 | Young et al. |
| 2005/0260748 A1 | 11/2005 | Chang et al. |
| 2005/0260750 A1 | 11/2005 | Kerr-Conte et al. |
| 2005/0271745 A1 | 12/2005 | Gruettner et al. |
| 2006/0018897 A1 | 1/2006 | Lee et al. |
| 2006/0020158 A1 | 1/2006 | Altman |
| 2006/0025713 A1 | 2/2006 | Rosengart et al. |
| 2006/0041182 A1 | 2/2006 | Forbes et al. |
| 2006/0078496 A1 | 4/2006 | Altman et al. |

(56) References Cited

U.S. PATENT DOCUMENTS

| | | |
|---|---|---|
| 2006/0083712 A1 | 4/2006 | Anversa |
| 2006/0084089 A1 | 4/2006 | Fort et al. |
| 2006/0084943 A1 | 4/2006 | Rosenman et al. |
| 2006/0142749 A1 | 6/2006 | Ivkov |
| 2006/0165805 A1 | 7/2006 | Steinhoff |
| 2006/0198829 A1 | 9/2006 | Rosen et al. |
| 2006/0205071 A1 | 9/2006 | Hasson et al. |
| 2006/0224111 A1 | 10/2006 | Rosenman et al. |
| 2006/0233712 A1 | 10/2006 | Penades et al. |
| 2006/0234375 A1 | 10/2006 | Doronin et al. |
| 2006/0239980 A1 | 10/2006 | Miana et al. |
| 2006/0239983 A1 | 10/2006 | Anversa |
| 2006/0281791 A1 | 12/2006 | Keating et al. |
| 2007/0003528 A1 | 1/2007 | Consigny et al. |
| 2007/0014869 A1 | 1/2007 | Matheny |
| 2007/0048383 A1 | 3/2007 | Helmus |
| 2007/0053839 A1 | 3/2007 | Zhang |
| 2007/0054397 A1 | 3/2007 | Ott et al. |
| 2007/0072291 A1 | 3/2007 | Kremer et al. |
| 2007/0088244 A1 | 4/2007 | Miller et al. |
| 2007/0099268 A1 | 5/2007 | Cohen et al. |
| 2007/0129296 A1 | 6/2007 | Zhou |
| 2007/0134210 A1 | 6/2007 | Heidaran |
| 2007/0142774 A1 | 6/2007 | Rosenman |
| 2007/0166288 A1 | 7/2007 | Murray et al. |
| 2007/0196281 A1 | 8/2007 | Jin et al. |
| 2007/0196918 A1 | 8/2007 | Sayre et al. |
| 2007/0197891 A1 | 8/2007 | Shachar et al. |
| 2007/0231393 A1 | 10/2007 | Ritter et al. |
| 2007/0248580 A1 | 10/2007 | Garcia Castro et al. |
| 2007/0292353 A1 | 12/2007 | Levy et al. |
| 2008/0006281 A1 | 1/2008 | Ou et al. |
| 2008/0027313 A1 | 1/2008 | Shachar |
| 2008/0031854 A1 | 2/2008 | Prestwich et al. |
| 2008/0076176 A1 | 3/2008 | Dominko et al. |
| 2008/0089874 A1 | 4/2008 | Li et al. |
| 2008/0103536 A1 | 5/2008 | Xiao |
| 2008/0138416 A1 | 6/2008 | Rauh et al. |
| 2008/0187514 A1 | 8/2008 | Anversa |
| 2008/0213230 A1 | 9/2008 | Phillips et al. |
| 2008/0213812 A1 | 9/2008 | Andrews et al. |
| 2008/0260704 A1 | 10/2008 | Riordan et al. |
| 2008/0267921 A1 | 10/2008 | Marbán et al. |
| 2008/0268061 A1 | 10/2008 | Jordan et al. |
| 2008/0274998 A1 | 11/2008 | Cohen et al. |
| 2008/0287918 A1 | 11/2008 | Rosenman et al. |
| 2008/0297287 A1 | 12/2008 | Shachar et al. |
| 2008/0319420 A1 | 12/2008 | Rosenman et al. |
| 2009/0011004 A1 | 1/2009 | Lutz et al. |
| 2009/0074728 A1 | 3/2009 | Gronthos et al. |
| 2009/0081170 A1 | 3/2009 | Riley |
| 2009/0081276 A1 | 3/2009 | Alsberg et al. |
| 2009/0099611 A1 | 4/2009 | Sigg et al. |
| 2009/0123366 A1 | 5/2009 | Dobson et al. |
| 2009/0136582 A1 | 5/2009 | Albrecht et al. |
| 2009/0143296 A1 | 6/2009 | Anversa et al. |
| 2009/0143748 A1 | 6/2009 | Mickley et al. |
| 2009/0148415 A1 | 6/2009 | de la Fuente et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0177152 A1 | 7/2009 | Altman |
| 2009/0180998 A1 | 7/2009 | Anversa et al. |
| 2009/0226521 A1 | 9/2009 | Smyth et al. |
| 2009/0317369 A1 | 12/2009 | Hosoda et al. |
| 2010/0010073 A1 | 1/2010 | Thum et al. |
| 2010/0012880 A1 | 1/2010 | Rampersaud et al. |
| 2010/0040587 A1 | 2/2010 | Haag et al. |
| 2010/0068811 A1 | 3/2010 | Marbán et al. |
| 2010/0081200 A1 | 4/2010 | Rajala et al. |
| 2010/0233216 A1 | 9/2010 | Cantaluppi et al. |
| 2010/0239538 A9 | 9/2010 | Anversa et al. |
| 2010/0255034 A1 | 10/2010 | Meinke et al. |
| 2010/0303716 A1 | 12/2010 | Jin et al. |
| 2010/0303722 A1 | 12/2010 | Jin et al. |
| 2010/0303909 A1 | 12/2010 | Oh et al. |
| 2010/0310534 A1 | 12/2010 | Oved et al. |
| 2011/0003003 A1 | 1/2011 | Goldberg et al. |
| 2011/0003008 A1 | 1/2011 | Lim |
| 2011/0034753 A1 | 2/2011 | Dobson et al. |
| 2011/0064675 A1 | 3/2011 | Hadjipanayis et al. |
| 2011/0070153 A1 | 3/2011 | Hyde et al. |
| 2011/0070154 A1 | 3/2011 | Hyde et al. |
| 2011/0091428 A1 | 4/2011 | Anversa |
| 2011/0091448 A1 | 4/2011 | Moon et al. |
| 2011/0092961 A1 | 4/2011 | Hyde et al. |
| 2011/0110897 A1 | 5/2011 | Schwarz et al. |
| 2011/0111412 A1 | 5/2011 | Tai et al. |
| 2011/0123500 A1 | 5/2011 | Anversa et al. |
| 2011/0135577 A1 | 6/2011 | Wu et al. |
| 2011/0152835 A1 | 6/2011 | Anversa |
| 2011/0165068 A1 | 7/2011 | Liu et al. |
| 2011/0177054 A1 | 7/2011 | Gibbings et al. |
| 2011/0256105 A1 | 10/2011 | Marbán et al. |
| 2011/0256621 A1 | 10/2011 | Albrecht et al. |
| 2011/0258716 A1 | 10/2011 | Baltimore et al. |
| 2011/0280834 A1 | 11/2011 | Forrester et al. |
| 2011/0300111 A1 | 12/2011 | White et al. |
| 2011/0300112 A1 | 12/2011 | Marbán et al. |
| 2012/0021019 A1 | 1/2012 | Giacomello et al. |
| 2012/0034156 A1 | 2/2012 | Hyde et al. |
| 2012/0034157 A1 | 2/2012 | Hyde et al. |
| 2012/0039857 A1 | 2/2012 | Smith et al. |
| 2012/0093879 A1 | 4/2012 | Giacomello et al. |
| 2012/0093885 A1 | 4/2012 | Sahoo et al. |
| 2012/0165392 A1 | 6/2012 | Olson et al. |
| 2012/0171291 A1 | 7/2012 | Rademacher et al. |
| 2012/0177574 A1 | 7/2012 | Gho et al. |
| 2012/0183528 A1 | 7/2012 | Ebert et al. |
| 2012/0201795 A1 | 8/2012 | Ware et al. |
| 2012/0238619 A1 | 9/2012 | Dimmeler et al. |
| 2012/0253102 A1 | 10/2012 | Marbán et al. |
| 2012/0258093 A1 | 10/2012 | Butler-Browne et al. |
| 2012/0315252 A1 | 12/2012 | Marbán et al. |
| 2013/0059006 A1 | 3/2013 | Schmuck et al. |
| 2013/0177593 A1 | 7/2013 | Gunn et al. |
| 2013/0266543 A1 | 10/2013 | Nadal-Ginard |
| 2013/0288962 A1 | 10/2013 | Anversa et al. |
| 2013/0295060 A1 | 11/2013 | Yang et al. |
| 2013/0309304 A1 | 11/2013 | Nadal-Ginard |
| 2014/0031256 A1 | 1/2014 | Lim |
| 2014/0120066 A1 | 5/2014 | Yeghiazarians et al. |
| 2014/0121171 A1 | 5/2014 | Muñoz-Cánoves et al. |
| 2014/0156200 A1 | 6/2014 | Verhaegh et al. |
| 2014/0235526 A1 | 8/2014 | Srivastava et al. |
| 2014/0275976 A1 | 9/2014 | Moro |
| 2015/0010640 A1 | 1/2015 | Marbán et al. |
| 2015/0273113 A1 | 10/2015 | Marbán et al. |
| 2015/0328263 A1 | 11/2015 | Kaushal |
| 2016/0158291 A1 | 6/2016 | Kreke et al. |
| 2016/0244723 A1 | 8/2016 | Giacomello et al. |
| 2017/0049793 A1 | 2/2017 | Moon et al. |
| 2017/0087087 A1 | 3/2017 | Leonard et al. |
| 2017/0290860 A1 | 10/2017 | Marbán et al. |
| 2017/0304368 A1 | 10/2017 | Marbán et al. |
| 2018/0100149 A1 | 4/2018 | Marbán et al. |
| 2019/0000888 A1 | 1/2019 | Marbán et al. |
| 2019/0160111 A1 | 5/2019 | Marbán et al. |
| 2019/0255119 A1 | 8/2019 | Marbán et al. |
| 2020/0024604 A1 | 1/2020 | Marbán et al. |
| 2020/0121727 A1 | 4/2020 | Marbán et al. |
| 2020/0316226 A1 | 10/2020 | Marbán et al. |

FOREIGN PATENT DOCUMENTS

| | | |
|---|---|---|
| CN | 1772300 | 5/2006 |
| CN | 1785430 | 6/2006 |
| EP | 1 254 952 | 11/2002 |
| EP | 1 857 544 | 11/2007 |
| EP | 1 970 446 | 9/2008 |
| EP | 2 182 053 | 5/2010 |
| EP | 2 228 444 | 9/2010 |
| EP | 1 631 318 | 11/2010 |

(56) References Cited

FOREIGN PATENT DOCUMENTS

| | | |
|---|---|---|
| EP | 1 650 293 | 12/2010 |
| EP | 2 371 370 | 10/2011 |
| EP | 2 385 120 | 11/2011 |
| EP | 2 446 929 | 5/2012 |
| EP | 1 945 256 | 7/2012 |
| EP | 2 094 869 | 7/2012 |
| EP | 2 486 944 | 8/2012 |
| EP | 2 277 548 | 1/2013 |
| EP | 2 687 219 | 1/2014 |
| JP | 2005-506845 | 3/2005 |
| JP | 2005-110565 | 4/2005 |
| JP | 2006-006125 | 1/2006 |
| JP | 2008-504816 | 2/2008 |
| JP | 2008-518730 | 6/2008 |
| KR | 100830889 | 5/2008 |
| KR | 10-1818560 | 1/2018 |
| WO | WO 97/005265 | 2/1997 |
| WO | WO 97/012912 | 4/1997 |
| WO | WO 98/004708 | 2/1998 |
| WO | WO 98/032866 | 7/1998 |
| WO | WO 99/011809 | 3/1999 |
| WO | WO 99/039624 | 8/1999 |
| WO | WO 99/049015 | 9/1999 |
| WO | WO 99/051297 | 10/1999 |
| WO | WO 00/009185 | 2/2000 |
| WO | WO 00/024452 | 5/2000 |
| WO | WO 01/010482 | 2/2001 |
| WO | WO 01/026585 | 4/2001 |
| WO | WO 01/026706 | 4/2001 |
| WO | WO 01/026727 | 4/2001 |
| WO | WO 01/048151 | 7/2001 |
| WO | WO 01/076679 | 10/2001 |
| WO | WO 01/076682 | 10/2001 |
| WO | WO 02/009650 | 2/2002 |
| WO | WO 02/013760 | 2/2002 |
| WO | WO 02/051489 | 7/2002 |
| WO | WO 03/004626 | 1/2003 |
| WO | WO 03/006950 | 1/2003 |
| WO | WO 03/008535 | 1/2003 |
| WO | WO 03/049626 | 6/2003 |
| WO | WO 03/064463 | 8/2003 |
| WO | WO 03/103611 | 12/2003 |
| WO | WO 03/103764 | 12/2003 |
| WO | WO 2004/044142 | 5/2004 |
| WO | WO 2005/012510 | 2/2005 |
| WO | WO 2006/007529 | 1/2006 |
| WO | WO 2006/052925 | 5/2006 |
| WO | WO 2006/065949 | 6/2006 |
| WO | WO 2006/081190 | 8/2006 |
| WO | WO 2007/019398 | 2/2007 |
| WO | WO 2007/069666 | 6/2007 |
| WO | WO 2007/100530 | 9/2007 |
| WO | WO 2007/106175 | 9/2007 |
| WO | WO 2008/036776 | 3/2008 |
| WO | WO 2008/043521 | 4/2008 |
| WO | WO 2008/058216 | 5/2008 |
| WO | WO 2008/058273 | 5/2008 |
| WO | WO 2008/118820 | 10/2008 |
| WO | WO 2008/124133 | 10/2008 |
| WO | WO 2009/032456 | 3/2009 |
| WO | WO 2009/056116 | 5/2009 |
| WO | WO 2009/058818 | 5/2009 |
| WO | WO 2009/062143 | 5/2009 |
| WO | WO 2009/062169 | 5/2009 |
| WO | WO 2009/067644 | 5/2009 |
| WO | WO 2009/073518 | 6/2009 |
| WO | WO 2009/073594 | 6/2009 |
| WO | WO 2009/073616 | 6/2009 |
| WO | WO 2009/073618 | 6/2009 |
| WO | WO 2009/100137 | 8/2009 |
| WO | WO 2009/103818 | 8/2009 |
| WO | WO 2009/149956 | 12/2009 |
| WO | WO 2009/152111 | 12/2009 |
| WO | WO 2010/015665 | 2/2010 |
| WO | WO 2010/028090 | 3/2010 |
| WO | WO 2010/033285 | 3/2010 |
| WO | WO 2010/059806 | 5/2010 |
| WO | WO 2010/083466 | 7/2010 |
| WO | WO 2010/118059 | 10/2010 |
| WO | WO 2010/135570 | 11/2010 |
| WO | WO 2011/029092 | 3/2011 |
| WO | WO 2011/029903 | 3/2011 |
| WO | WO 2011/053901 | 5/2011 |
| WO | WO 2011/056685 | 5/2011 |
| WO | WO 2011/057249 | 5/2011 |
| WO | WO 2011/057251 | 5/2011 |
| WO | WO 2011/062244 | 5/2011 |
| WO | WO 2011/064354 | 6/2011 |
| WO | WO 2011/084460 | 7/2011 |
| WO | WO 2011/121120 | 10/2011 |
| WO | WO 2011/127625 | 10/2011 |
| WO | WO 2011/138328 | 11/2011 |
| WO | WO 2011/143499 | 11/2011 |
| WO | WO 2012/019103 | 2/2012 |
| WO | WO 2012/020307 | 2/2012 |
| WO | WO 2012/020308 | 2/2012 |
| WO | WO 2012/055971 | 5/2012 |
| WO | WO 2012/065027 | 5/2012 |
| WO | WO 2012/125471 | 9/2012 |
| WO | WO 2012/135253 | 10/2012 |
| WO | WO 2012/149557 | 11/2012 |
| WO | WO 2012/162741 | 12/2012 |
| WO | WO 2013/048734 | 4/2013 |
| WO | WO 2013/170170 | 11/2013 |
| WO | WO 2013/184527 | 12/2013 |
| WO | WO 2014/013258 | 1/2014 |
| WO | WO 2014/028493 | 2/2014 |
| WO | WO 2014/160153 | 10/2014 |
| WO | WO 2015/085096 | 6/2015 |
| WO | WO 2015/120150 | 8/2015 |
| WO | WO 2016/054591 | 4/2016 |
| WO | WO 2016/057560 | 4/2016 |
| WO | WO 2019/028223 | 2/2019 |
| WO | WO 2019/126068 | 6/2019 |
| WO | WO 2019/152549 | 8/2019 |
| WO | WO 2020/227489 | 11/2020 |

OTHER PUBLICATIONS

Tateishi et al., "Clonally Amplified Cardiac Stem Cells are Regulated by Sca-1 Signaling for Efficient Cardiovascular Regeneration", Journal of Cell Science, 2007, vol. 120, No. 10, pp. 1791-1800.

Ten Dijke et al. "Identification of Another Member of the Transforming Growth Factor Type β Gene Family", Proceedings of the National Academy of Sciences of the United States of America (PNAS), 1988, vol. 85, pp. 4715-4719.

Terrovitis, MD, et al., "Assessment and Optimization of Cell Engraftment after Transplantation into the Heart", Circulation Research, Feb. 19, 2010, vol. 106, No. 3, pp. 479-494.

Terrovitis, MD, et al., "Noninvasive Quantification and Optimization of Acute Cell Retention by In Vivo Positron Emission Tomography after Intramyocardial Cardiac-Derived Stem Cell Delivery", Journal of the American College of Cardiology, Oct. 20, 2009, vol. 54, No. 17, pp. 1619-1626.

The Exosomes Derived from CDCs Experimental Data to Show that Unexpectedly Improved Characteristics are Exhibited, p. 1.

Tomita et al., "Cardiac Neural Crest Cells Contribute to the Dorman Multipotent Stem Cell in the Mammalian Heart", Journal of Cell Biology, Sep. 26, 2005, vol. 170, No. 7, pp. 1135-1148.

Torella et al., "Cardiac Stem Cell and Myocyte Aging, Heart Failure, and Insulin-Like Growth Factor-1 Overexpression", Circulation Research, 2004, vol. 95, pp. 514-524.

Torella et al., Resident Human Cardiac Stem Cells: Role in Cardiac Cellular Homeostasis and Potential for Myocardial Regeneration, Nature Clinical Practice: Cardiovascular Medicine, Mar. 2006, vol. 3, No. 1, pp. S8-S13.

Trevethick et al., "Treating Lung Inflammation with Agonists from the Adenosine A2A Receptor: Promises, Problems and Potential Solutions", British Journal of Pharmacology, 2008, vol. 155, pp. 463-474.

(56) References Cited

OTHER PUBLICATIONS

Tsagalou, MD, et al., "Depressed Coronary Flow Reserve is Associated with Decreased Myocardial Capillary Density in Patients with Heart Failure Due to Idiopathic Dilated Cardiomyopathy", Journal of the American College of Cardiology, 2008, vol. 52, No. 17, pp. 1391-1398.
Tseliou et al., "Abstract 15925: Newt Exosomes are Bioactive on Mammalian Heart, Enhancing Proliferation of Rat Cardiomyocytes and Improving Recovery After Myocardial Infarction", Circulation, Nov. 10, 2015, vol. 132, No. 3, pp. 2.
Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.
Tsutsui, Hiroyuki, "Cardiomyopathy: Progress in Diagnosis and Treatments Topics: 1. New classification based on etiology of cardiomyopathy; 1. Classification of cardiomyopathy—its past and present status", The Japanese Society of Internal Medicine, Feb. 2014, vol. 103, No. 2, pp. 277-284.
Uemura et al., "Bone Marrow Stem Cells Prevent Left Ventricular Remodeling of Ischemic Heart Through Paracrine Signaling", Circulation Research, 2006, vol. 98, pp. 1414-1421.
Abdel-Latif et al., "Adult Bone Marrow-Derived Cells for Cardiac Repair: A Systematic Review and Meta-Analysis", Archives of Internal Medicine, vol. 167, May 28, 2007, pp. 989-997.
Abela et al., "A New Method for Isolation of Cardiac Myocytes by Percutaneous Endomyocardial Biopsy", Catheterization and Cardiovascular Diagnosis, 1996, vol. 37, pp. 227-230.
Agrahari et al., "How Are We Improving the Delivery to Back of the Eye? Advances and Challenges of Novel Therapeutic Approaches", Expert Opinion on Drug Delivery, 2017, vol. 14, No. 10, pp. 1145-1162.
Ajijola et al., "Ventricular Tachycardia in Ischemic Heart Disease Substrates", Indian Heart Journal, 2014, pp. S24-S34, S28 & S30, vol. 66, Supplement 1.
Albini et al., "A Rapid in Vitro Assay for Quantitating the Invasive Potential of Tumor Cells", Cancer Research, Jun. 15, 1987, pp. 3239-3245, vol. 47.
Ames et al., "Oxidants, Antioxidants, and the Degenerative Diseases of Aging", Proceedings of the National Academy of Sciences of the United States of America, Sep. 1993, vol. 90, pp. 7915-7922.
Aminzadeh et al., "Exosome-Mediated Benefits of Cell Therapy in Mouse and Human Models of Duchenne Muscular Dystrophy", Stem Cell Reports, Mar. 13, 2018, vol. 10, No. 3, pp. 942-955.
Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Dec. 5, 2014, vol. 115, No. 12, 24248, pp. E90-E91.
Aminzadeh et al., "Mitigation of Skeletal Myopathy After Intramyocardial Injection of Cardiosphere-derived Cells in the Mdx Mouse Model of Duchenne Muscular Dystrophy", Circulation Research, Dec. 4, 2015, No. 22919, pp. e122-e127.
Andersen et al., "Murine 'Cardiospheres' Are Not a Source of Stem Cells with Cardiomyogenic Potential," Stem Cells, 2009, vol. 27, No. 7, pp. 1571-1581.
Anversa et al., "Primitive Cells and Tissue Regeneration", Circulation Research, 2003, vol. 92, pp. 579-582.
Assmus et al., "Transplantation of Progenitor Cells and Regeneration Enhancement in Acute Myocardial Infarction (TOPCARE-AMI)", Circulation, Dec. 10, 2002, vol. 106, pp. 3009-3017.
"ATS/ACCP Statement on Cardiopulmonary Exercise Testing", American Thoracic Society/American College of Chest Physicians, American Journal of Respiratory and Critical Care Medicine, 2003, vol. 167, pp. 211-277.
Ausma et al., "Dedifferentiation of Atrial Cardiomyocytes: From in Vivo to In Vitro", Cardiovascular Research, Jul. 2002, vol. 55, No. 1, pp. 9-12.

Baker et al. "Adaptation to Culture of Human Embryonic Stem Cells and Oncogenesis in Vivo" Nature Biotechnology, Feb. 2007, vol. 25, No. 2, pp. 207-215.
Balser et al., "Global Parameter Optimization for Cardiac Potassium Channel Gating Models", Biophysical Journal, Mar. 1990, vol. 57, pp. 433-444.
Balser et al., "Local Anesthetics as Effectors of Allosteric Gating", Journal of Clinical Investigation, Dec. 1996, vol. 98, No. 12, pp. 2874-2886.
Barbash et al., "Systemic Delivery of Bone-Marrow-Derived Mesenchymal Stem Cells to the Infarcted Myocardium Feasibility, Cell Migration, and Body Distribution," Circulation, Apr. 19, 2003, vol. 108, pp. 863-868.
Barile et al., "Cardiac Stem Cells: Isolation, Expansion and Experimental use for Myocardial Regeneration", Nature Clinical Practice Cardiovascular Medicine, Feb. 2007, vol. 4, No. 1, pp. S9-S14.
Barile et al., "Endogenous Cardiac Stem Cells", Progress in Cardiovascular Diseases, Jul.-Aug. 2007, vol. 50, No. 1, pp. 31-48.
Barile et al., "Human Cardiospheres as a Source of Multipotent Stem and Progenitor Cells", Hindawi Publishing Corporation, Stem Cells International, 2013, vol. 2013, pp. 10.
Barr et al., "Efficient Catheter-Mediated Gene Transfer Into the Heart Using Replication-Defective Adenovirus", Gene Therapy, Jan. 1994, vol. 1, No. 1, pp. 51-58.
Barry et al., "Differential Expression of Voltage-Gated $K^+$ Channel Subunits in Adult Rat Heart", Circulation Research, 1995, vol. 77, pp. 361-369.
Barth et al., "Lentiviral Vectors Bearing the Cardiac Promoter of the $Na^+$-$Ca^{2+}$ Exchanger Report Cardiogenic Differentiation in Stem Cells", Molecular Therapy, May 2008, vol. 16, No. 5, pp. 957-964.
Bearzi et al., "Human Cardiac Stem Cells", Proceedings of the National Academy of Sciences of the United States of America (PNAS), Aug. 28, 2007, pp. 14068-14073, vol. 104, No. 35.
Beltrami et al., "Adult Cardiac Stem Cells are Multipotent and Support Myocardial Regeneration", Cell, Sep. 19, 2003, vol. 114, No. 6, pp. 763-776.
Beltrami et al., "Evidence That Human Cardiac Myocytes Divide After Myocardial Infarction", The New England Journal of Medicine, Jun. 7, 2001, vol. 344, pp. 1750-1757.
Beltrami et al., "Multipotent Cells Can be Generated In Vitro from Several Adult Human Organs (Heart, Liver and Bone Marrow)", Stem Cells in Hematology, Blood, 2007, pp. 3438-3446, vol. 110, No. 9.
Bénardeau et al., "Primary Culture of Human Atrial Myocytes is Associated with the Appearance of Structural and Functional Characteristics of Immature Myocardium", Journal of Molecular and Cellular Cardiology, 1997, vol. 29, pp. 1307-1320.
Bergmann et al., "Evidence for Cardiomyocyte Renewal in Humans", Science, Apr. 3, 2009, vol. 324, pp. 98-102.
Bernanke et al., "Effects of Hyaluronic Acid on Cardiac Cushion Tissue Cells in Collagen Matrix Cultures", Texas Reports on Biology and Medicine, 1979, pp. 271-285, vol. 39.
Bioptome.com, "Scholten Products", downloaded from http://www.bioptome.com/pages.php?page=Products, 2001, first date of publication unknown, printed on Nov. 1, 2005, pp. 2.
Bird et al., "The Human Adult Cardiomyocyte Phenotype", Cardiovascular Research, May 1, 2003, vol. 58, No. 2, pp. 423-434.
Birks et al., "Left Ventricular Assist Device and Drug Therapy for the Reversal of Heart Failure", The New England Journal of Medicine, 2006, vol. 355, No. 18, pp. 1873-1884.
Bjelakovic et al., "Mortality in Randomized Trials of Antioxidant Supplements for Primary and Secondary Prevention: Systematic Review and Meta-Analysis", JAMA, 2007, vol. 297, pp. 842-857.
Bosnali et al., "Generation of Transducible Versions of Transcription Factors Oct4 and Sox2", Biological Chemistry, Jul. 2008, vol. 389, pp. 851-861.
Bredemeyer et al., "ATM Stabilizes DNA Double-Strand-Break Complexes During V(D)J Recombination", Nature, Jul. 27, 2006, vol. 442, pp. 466-470.
Burstein et al., "Systemic and Coronary Delivery of Marrow Stromal Cells for Cellular Cardiomyoplasty: Advantages and Precautions", Basic and Applied Myology, 2003, vol. 13, No. 1, pp. 7-10.

(56) References Cited

OTHER PUBLICATIONS

Cai et al., "Injectable Glycosaminoglycan Hydrogels for Controlled Release of Human Basic Fibroblast Growth Factor," Biomaterials, 2005, vol. 26, pp. 6054-6067.
Cambier et al., "Y RNA Fragment in Extracellular Vesicles Confers Cardioprotection via Modulation of IL-10 Expression and Secretion", EMBO Molecular Medicine, 2017, vol. 9, No. 3, pp. 337-352.
"CArdiosphere-Derived aUtologous Stem CElls to Reverse ventricUlar dySfunction (CADUCEUS)", ClinicalTrials.gov, Identifier NCT00893360, 2009, pp. 6.
Chambers et al., "Functional Expression Cloning of Nanog, a Pluripotency Sustaining Factor in Embryonic Stem Cells", Cell, May 30, 2003, vol. 113, No. 5, pp. 643-655.
Chen et al., "Enhanced Tumorigenesis in p53 Knockout Mice Exposed in Utero to High-Dose Vitamin E", Carcinogenesis, 2006, vol. 27, No. 7, pp. 1358-1368.
Chen et al., "Mesenchymal Stem Cell Secretes Microparticles Enriched in Pre-MicroRNAs", Nucleic Acids Research, 2010, vol. 38, No. 1, pp. 215-224.
Chen et al., "Reduced Tumorigenesis in p53 Knockout Mice Exposed in Utero to Low-Dose Vitamin E", Cancer, Apr. 1, 2009, vol. 115, pp. 1563-1575.
Chen et al., "The Role of Notch 1 Activation in Cardiosphere Derived Cell Differentiation", Stem Cells and Development, 2012, pp. 2122-2129, vol. 21, No. 12.
Chen et al., "Vascular Endothelial Growth Factor Promotes Cardiomyocyte Differentiation of Embryonic Stem Cells", American Journal of Physiology-Heart and Circulatory Physiology, Oct. 2006, vol. 291, No. 4, pp. H1653-H1658.
Cheng et al., "Functional Performance of Human Cardiosphere-Derived Cells Delivered in an in situ Polymerizable Hyaluronan-Gelatin Hydrogel", Biomaterials, 2012, pp. 8.
Cheng et al., "Magnetic Targeting Enhances Engraftment and Functional Benefit of Iron-Labeled Cardiosphere-Derived Cells in Myocardial Infarction", Circulation Research, 2010, pp. 1570-1581, vol. 106.
Cheng et al., "Relative Roles of CD90 and c-Kit to the Regenerative Efficacy of Cardiosphere-Derived Cells in Humans and in a Mouse Mode of Myocardial Infarction", Journal of the American Heart Association, Oct. 9, 2014, pp. 1-10, vol. 3, No. 5.
Cheng et al., "Transplantation of Platelet Gel Spike with Cardiosphere-Derived Cells Boosts Structural and Functional Benefits Relative to Gel Transplantation Alone in Rats with Myocardial Infarction", Biomaterials, 2012, vol. 33, pp. 2872-2879.
Chimenti et al., "Abstract 3182: Paracrine Contribution versus Direct Regeneration in Cardiosphere-Derived Cell Therapy for Acute Myocardial Infarction", Circulation, 2009, vol. 120, p. S756.
Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.
Chlopčíková et al., "Neonatal Rat Cardiomyocytes—A Model for the Study of Morphological Biochemical and Electrophysiological Characteristics of the Heart", Biomedical Papers, 2001, vol. 145, No. 2, pp. 49-55.
Cho et al., "Secondary Sphere Formation Enhances the Functionality of Cardiac Progenitor Cells", Molecular Therapy, Sep. 2012, vol. 20, No. 9, pp. 1750-1766.
Christman et al., "Biomaterials for the Treatment of Myocardial Infarction", Journal of the American College Of Cardiology, 2006, vol. 48, No. 5, pp. 907-913.
Conkright et al., "A Gene Encoding an Intestinal-Enriched Member of the Krüppel-Like Factor Family Expressed in Intestinal Epithelia Cells", Nucleic Acids Research, 1999, vol. 27, No. 5, pp. 1263-1270.
Cooper et al., "Immunobiological Barriers to Xenotransplantation", International Journal of Surgery, 2015, vol. 23, pp. 211-216.
Crisostomo et al., "Embryonic Stem Cells Attenuate Myocardial Dysfunction and Inflammation After Surgical Global Ischemia Via Paracrine Actions", American Journal of Physiology-Heart and Circulatory Physiology, 2008, vol. 295, pp. H1726-H1735.
Csete, Marie, "Oxygen in the Cultivation of Stem Cells", Annals New York Academy of Sciences, 2005, vol. 1049, pp. 1-8.
"Culture Media Database", EGM-2 (Endothelial Growth Medium 2)—ID 63, downloaded from http://bio.lonza.com/3018.html#ext-comp-1003:tab_63:change, printed on Jan. 14, 2013, p. 1.
Davis et al., "Human Cardiospheres are a Source of Stem Cells with Cardiomyogenic Potential", Stem Cells, 2010, vol. 28, No. 5, pp. 903-904.
Davis et al., "Isolation and Expansion of Functionally-Competent Cardiac Progenitor Cells Directly from Heart Biopsies", Journal of Molecular and Cellular Cardiology, Aug. 2010, vol. 49, No. 2, pp. 312-321.
Davis et al., "Validation of the Cardiosphere Method to Culture Cardiac Progenitor Cells from Myocardial Tissue", PLoS One, 2009, vol. 4, No. 9, e7195, pp. 1-8.
De Bakker et al, "Slow Conduction in the Infarcted Human Heart 'Zigzag' Course of Activation", Circulation, Sep. 1993, pp. 915-926, vol. 88, No. 3.
De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.
De Pomerai et al., "Influence of Serum Factors on the Prevalence of 'Normal' and 'Foreign' Differentiation Pathways in the Cultures of Chick Embryo Neuroretinal Cells", Journal of Embryology and Experimental Morphology, 1981, pp. 291-308, vol. 62.
Deal et al., "Molecular Physiology of Cardiac Potassium Channels", Physiological Reviews, Jan. 1996, vol. 76, No. 1, pp. 49-67.
Del Monte et al., "Abrogation of Ventricular Arrhythmias in a Model of Ischemia and Reperfusion by Targeting Myocardial Calcium Cycling", Proceedings of the National Academy of Sciences of the United States of America (PNAS), Apr. 13, 2004, vol. 101, No. 15, pp. 5622-5627.
Deregibus et al., "Endothelial Progenitor Cell-Derived Microvesicles Activate an Angiogenic Program in Endothelial Cells by a Horizontal Transfer of mRNA", Blood, Oct. 1, 2007, vol. 110, No. 7, pp. 2440-2448.
Derossi et al., "The Third Helix of the Antennapedia Homeodomain Translocates through Biological Membranes", The Journal of Biological Chemistry, Apr. 8, 1994, vol. 269, No. 14, pp. 10444-10450.
Di Meglio et al., "In Vitro Cultured Progenitors and Precursors of Cardiac Cell Lineages from Human Normal and Post-Ischemic Hearts", European Journal of Histochemistry, Oct.-Dec. 2007, vol. 51, No. 4, pp. 275-285.
Dib et al., "Cell Therapy for Cardiovascular Disease: A Comparison of Methods of Delivery", Journal of Cardiovascular Translational Research, 2011, vol. 4, pp. 177-181.
Dispersyn et al., "Adult Rabbit Cardiomyocytes Undergo Hibernation-Like Dedifferentiation When Co-Cultured with Cardiac Fibroblasts", Cardiovascular Research, 2001, vol. 51, pp. 230-240.
Dispersyn et al., "Dissociation of Cardiomyocyte Apoptosis and Dedifferentiation in Infarct Border Zones", European Heart Journal, 2002, vol. 23, pp. 849-857.
Dixon et al., "Quantitative Analysis of Potassium Channel mRNA Expression in Atrial and Ventricular Muscle of Rats", Circulation Research, Aug. 1994, vol. 75, No. 2, pp. 252-260.
Dixon et al., "Role of the Kv4.3 $K^+$ Channel in Ventricular Muscle", Circulation Research, 1996, vol. 79, pp. 659-668.
Djokic et al., "Post-Transplant Lymphoproliferative Disorder Subtypes Correlate with Different Recurring Chromosomal Abnormalities", Genes, Chromosomes & Cancer, 2006, vol. 45, pp. 313-318.
Donahue et al., "Ultrarapid, Highly Efficient Viral Gene Transfer to the Heart", Proceedings of the National Academy of Sciences of the United States of America, Apr. 1997, vol. 94, pp. 4664-4668.
Dong et al., "Islet Cell and Extrapancreatic Expression of the LIM Domain Homeobox Gene isl-1", Molecular Endocrinology, 1991, vol. 5, No. 11, pp. 1633-1641.
Drakos et al., "Impact of Mechanical Unloading on Microvasculature and Associated Central Remodeling Features of the Failing Human Heart", Journal of the American College of Cardiology, Jul. 27, 2010, vol. 56, No. 5, pp. 382-391.

(56) References Cited

OTHER PUBLICATIONS

Driesen et al., "Structural Adaptation in Adult Rabbit Ventricular Myocytes: Influence of Dynamic Physical Interaction With Fibroblasts", Cell Biochemistry and Biophysics, 2006, vol. 44: 119-128.
Driesen et al., "Structural Remodeling of Cardiomyocytes in the Border Zone of Infarcted Rabbit Heart", Molecular and Cellular Biochemistry, 2007, pp. 225-232, vol. 302.
Duff et al., "CD105 is Important for Angiogenesis: Evidence and Potential Applications," FASEB Journal, Jun. 2003, vol. 17, No. 9, pp. 984-992.
Eguchi, Masakatsu, "Recent Advances in Selective Opioid Receptor Agonists and Antagonists", Medicinal Research Reviews, 2004, vol. 24, No. 2, pp. 182-212.
Elliott et al., "Intercellular Trafficking and Protein Delivery by a Herpesvirus Structural Protein", Cell, Jan. 24, 1997, vol. 88, pp. 223-233.
Elliott et al., "Intercellular Trafficking of VP22-GFP Fusion Proteins", Gene Therapy, 1999, vol. 6, pp. 149-151.
Engel et al., FGF1/p38 MAP Kinase Inhibitor Therapy Induces Cardiomyocyte Mitosis, Reduces Scarring, and Rescues Function after Myocardial Infarction, Proceedings of the National Academy of Sciences of the United States of America (PNAS), Oct. 17, 2006, vol. 103, No. 42, pp. 15546-15551.
Engel et al. "p38 MAP Kinase Inhibition Enables Proliferation of Adult Mammalian Cardiomyocytes", Genes & Development, May 2005, vol. 19, No. 10, pp. 1175-1187.
Eppenberger-Eberhardt et al., "Reexpression of α-Smooth Muscle Acting Isoform in Cultured Adult Rat Cardiomyocytes", Developmental Biology, Jun. 1990, vol. 139, No. 2, pp. 269-278.
Eschenhagen et al., "Engineering Myocardial Tissue", Circulation Research, 2005, vol. 97, pp. 1220-1231.
Falck et al., "Conserved Modes of Recruitment of ATM, ATR and DNA-PKcs to Sites of DNA Damage", Nature, Mar. 31, 2005, vol. 434, pp. 605-611.
Fehrer et al., "Reduced Oxygen Tension Attenuates Differentiation Capacity of Human Mesenchymal Stem Cells and Prolongs their Lifespan", Aging Cell, 2007, vol. 6, pp. 745-757.
Fiset et al., Shal-Type Channels Contribute to the $Ca^{2+}$-Independent Transient Outward $K^+$ Current in Rat Ventricle, Journal of Physiology, 1997, vol. 500, No. 1, pp. 51-64.
Foreman et al., "Reactive Oxygen Species Produced by NADPH Oxidase Regulate Plant Cell Growth", Nature, Mar. 27, 2003, vol. 422, pp. 442-446.
Frankel et al., "Cellular Uptake of the Tat Protein from Human Immunodeficiency Virus", Cell, vol. 55, Dec. 23, 1988, pp. 1189-1193.
Freyman et al., "A Quantitative, Randomized Study Evaluating Three Methods of Mesenchymal Stem Cell Delivery Following Myocardial Infarction", European Heart Journal, 2006, vol. 27, pp. 1114-1122.
Furlani et al., "A Transformed Cell Population Derived From Cultured Mesenchymal Stem Cells Has no Functional Effect After Transplantation Into the Injured Heart", Cell Transplantation, 2009, vol. 18, pp. 319-331.
Gallet et al, "Cardiosphere-Derived Cells Reverse Heart Failure with Preserved Ejection Fraction in Rats by Decreasing Fibrosis and Inflammation", JACC: Basic to Translational Science, Jan. 1, 2016, vol. 1, No. 1-2, pp. 14-28.
Gallet et al, "Intracoronary Delivery of Self-Assembling Heart-Derived Microtissues (Cardiospheres) For Prevention of Adverse Remodeling In a Pig Model of Convalescent Myocardial Infarction", http://circinterventions.ahajournals.org, Dec. 8, 2015, pp. 21.
Galli et al., "Neural Stem Cells: An Overview", Circulation Research, 2003, vol. 92, No. 6, pp. 598-608.
Gatti et al., Microvesicles Derived from Human Adult Mesenchymal Stem Cells Protect Against Ischaemia-Reperfusion-Induced Acute and Chronic Kidney Injury, Nephrology Dialysis Transplantation, 2011, vol. 26, No. 5, pp. 1474-1483.

George et al, "Echocardiographic Assessment of Flow Across Continuous-Flow Ventricular Assist Devices at Low Speeds", The Journal of Heart and Lung Transplantation, Nov. 2010, vol. 29, No. 11, pp. 1245-1252.
Gibco, "Insulin-Transferrin-Selenium", Product Sheet, 2014.
Gibco, "Insulin-Transferrin-Selenium: 100X (For General Tissue Culture Applications)", Product Sheet, Form No. 2672, Jun. 2001, p. 1.
Gidh-Jain et al., Differential Expression of Voltage-Gated $K^+$ Channel Genes in Left Ventricular Remodeled Myocardium After Experimental Myocardial Infarction, Circulation Research, 1996, vol. 79, pp. 669-675.
Glover et al., "Reduction of Infarct Size and Postischemic Inflammation from ATL-146e, a Highly Selective Adenosine $A_{2A}$ Receptor Agonist in Reperfused Canine Myocardium", American Journal of Physiology-Heart and Circulatory Physiology, Apr. 2005, vol. 288, No. 4, pp. H1851-H1858.
Gómez-Márquez et al., "Thymosin-β4 Gene: Preliminary Characterization and Expression in Tissues, Thymic Cells, and Lymphocytes", The Journal of Immunology, Oct. 15, 1989, vol. 143, No. 8, pp. 2740-2744.
Good et al., "ß-Amyloid Peptide Blocks the Fast-Inactivating $K^+$ Current in Rat Hippocampal Neurons", Biophysical Journal, Jan. 1996, vol. 70, pp. 296-304.
Goumans et al., "TGF-β1 Induces Efficient Differentiation of Human Cardiomyocyte Progenitor Cells into Functional Cardiomyocytes In Vitro", Stem Cell Research, 2008, vol. 1, pp. 138-149.
Grayson et al. "Hypoxia Enhances Proliferation and Tissue Formation of Human Mesenchymal Stem Cells", Biochemical and Biophysical Research Communications, 2007, vol. 358, pp. 948-953.
Green et al., "Autonomous Functional Domains of Chemically Synthesized Human Immunodeficiency Virus Tat Trans-Activator Protein", Dec. 23, 1988, Cell, vol. 55, pp. 1179-1188.
Grigorian-Shamagian et al., "Cardiac and Systemic Rejuvenation After Cardiosphere-Derived Cell Therapy in Senescent Rats", European Heart Journal, Oct. 14, 2017, vol. 38, No. 39, pp. 2957-2967.
Grigorian-Shamagian et al., "Harnessing the Heart's Resistance to Malignant Tumors; Cardiac-Derived Extracellular Vesicles Decrease Fibrosarcoma Growth and Leukemia-Related Mortality in Rodents", Oncotarget, 2017, vol. 8, No. 59, pp. 99624-99636.
Grossman et al., "Contractile State of the Left Ventricle in Man as Evaluated from End-Systolic Pressure-Volume Relations", Circulation, vol. 56, No. 5, Nov. 1977, pp. 845-852.
Gu, Yiping, "Bispecific Antibody Targeted Stem Cell Therapy for Myocardial Repair", Dissertation, University of California San Francisco and University of California Berkeley, 2008, pp. 94.
Gubbay et al., "A Gene Mapping to the Sex-Determining Region of the Mouse Y Chromosome is a Member of a Novel Family of Embryonically Expressed Genes", Nature, Jul. 19, 1990, vol. 346, pp. 245-250.
Hacein-Bey-Abina et al., "LMO2-Associated Clonal T Cell Proliferation in Two Patients after Gene Therapy for SCID-X1", Science, Oct. 17, 2003, vol. 302, pp. 415-419 with Erratum in 1 page.
Haderk et al., "Tumor-Derived Exosomes Modulate PD-L1 Expression in Monocytes", Science Immunology, Jul. 28, 2017, vol. 2, No. 13, pp. 1-11.
Hagège, MD, PhD, et al., "Skeletal Myoblast Transplantation in Ischemic Heart Failure: Long-Term Follow-Up of the First Phase I Cohort of Patients", Circulation, Jul. 4, 2006, vol. 114, No. 1, pp. I108-I113.
Haider et al., "Bone Marrow Stem Cell Transplantation for Cardiac Repair", American Journal of Physiology-Heart and Circulatory Physiology, 2005, H2557-H2567, vol. 288.
Hainsworth et al., "The Nitrone Disodium 2,4-Sulphophenyl-N-Tert-Butylnitrone is Without Cytoprotective Effect on Sodium Nitroprusside-Induced Cell Death in N1E-115 Neuroblastoma Cells in vitro", Journal of Cerebral Blood Flow & Metabolism, 2008, vol. 28, pp. 24-28.
Haj-Yahia et al., "Limited Surgical Approach for Explanting the HeartMate II Left Ventricular Assist Device after Myocardial Recovery", The Journal of Thoracic and Cardiovascular Surgery, 2008, vol. 135, No. 2, pp. 453-454.

(56) References Cited

OTHER PUBLICATIONS

Harvey, "Molecular Determinants of Cardiac Development and Congenital Disease," Mouse Development, Patterning, Morphogenesis, and Organogensis, 2002, pp. 331-370, Chapter 16.
Heng et al., "Incorporating Protein Transduction Domains (PTD) Within Recombinant 'Fusion' Transcription Factors. A Novel Strategy for Directing Stem Cell Differentiation?" Biomedicine and Pharmacotherapy, Apr. 1, 2005, vol. 59, No. 3, pp. 132-134.
Hergenreider et al., "Atheroprotective Communication Between Endothelial Cells and Smooth Muscle Cells Through miRNAs", Nature Cell Biology, Mar. 2012, vol. 14, No. 3, pp. 249-256.
Herrera et al., "Human Liver Stem Cell-Derived Microvesicles Accelerate Hepatic Regeneration in Hepatectomized Rats", Journal of Cellular and Molecular Medicine, 2010, vol. 14, No. 6B, pp. 1605-1618.
Hierlihy et al., "The Post-Natal Heart Contains a Myocardial Stem Cell Population", FEBS Letters, 2002, vol. 530, No. 1-3, pp. 239-243.
Hine et al., "NRF2 and the Phase II Response in Acute Stress Resistance Induced by Dietary Restriction", Journal of Clinical & Experimental Pathology, Jun. 19, 2012, vol. S4, No. 4, pp. 1-33.
Hochedlinger et al., "Nuclear Reprogramming and Pluripotency", Nature, Jun. 29, 2006, vol. 441, pp. 1061-1067.
Hu et al., "MicroRNA-210 as a Novel Therapy for Treatment of Ischemic Heart Disease", Circulation, Sep. 14, 2010, vol. 122, Supplement 11, S124-S131, pp. 17.
Hullinger et al., Inhibition of miR-15 Protects Against Cardiac Ischemic Injury, Circulation Research, Jan. 6, 2012, vol. 110, No. 1, pp. 71-81.
Ibrahim et al., "Exosomes as Critical Agents of Cardiac Regeneration Triggered by Cell Therapy", Stem Cell Reports, May 6, 2014, vol. 2, pp. 606-619.
Ibrahim et al., "Exosomes: Fundamental Biology and Roles in Cardiovascular Physiology", Annual Review of Physiology, 2016, vol. 78, pp. 67-83.
Ibrahim et al., "Microrna-Containing Exosomes from Cardiosphere-Derived Cells Stimulate Cardiomyocyte Proliferation and Angiogenesis in Vitro, and Improve Functional Recovery after Myocardial Infarction in Mice", Circulation, 2012, vol. 126, Abs. 14697, pp. 4.
Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.
Ikehara et al., "Grand Challenges in Stem Cell Treatments", Frontiers in Cell and Developmental Biology, Oct. 10, 2013, vol. 1, No. 2, pp. 2.
Ivanovic, Zoran, "Hypoxia or In Situ Normoxia: The Stem Cell Paradigm", Journal of Cellular Physiology, 2009, vol. 219, pp. 271-275.
Jackson et al., "Regeneration of Ischemic Cardiac Muscle and Vascular Endothelium by Adult Stem Cells", The Journal of Clinical Investigation, Jun. 2001, pp. 1395-1402, vol. 107, No. 11.
Jayawardena et al., MicroRNA-Mediated In Vitro and In Vivo Direct Reprogramming of Cardiac Fibroblasts to Cardiomyocytes, Circulation Research, 2012, vol. 110, No. 11, pp. 1465-1473.
Johnston, MD, et al., "Engraftment, Differentiation, and Functional Benefits of Autologous Cardiosphere-Derived Cells in Porcine Ischemic Cardiomyopathy", Circulation, Sep. 22, 2009, vol. 120, pp. 1075-1083.
Jutkiewicz, Emily, The Antidepressant-Like Effects of Delta-Opioid Receptor Agonists, Molecular Interventions, 2006, vol. No. 3, pp. 162-169.
Kääb et al., "Ionic Mechanism of Action Potential Prolongation in Ventricular Myocytes From Dogs With Pacing-Induced Heart Failure", Circulation Research, 1996, vol. 78, No. 2, pp. 262-273.
Kamdar et al., "Dystrophin-Deficient Cardiomyopathy", Journal of the American College of Cardiology, 2016, vol. 67, No. 21, pp. 2533-2546.

Karlsson et al., "Insulin Gene Enhancer Binding Protein Isl-1 is a Member of a Novel Class of Proteins Containing Both a Homeo-and a Cys-His Domain", Nature, Apr. 26, 1990, vol. 344, pp. 879-882.
Karoubi et al., "Single-Cell Hydrogel Encapsulation for Enhanced Survival of Human Marrow Stromal Cells", Biomaterials, 2009, vol. 30, pp. 5445-5455.
Kaspar et al., "Current Understanding and Management of Dilated Cardiomyopathy in Duchenne and Becker Muscular Dystrophy", Journal of the American Association of Nurse Practitioners, May 2009, vol. 21, No. 5, pp. 241-249.
Kawaguchi et al., "Cell Shape and Cardiosphere Differentiation: A Revelation by Proteomic Profiling", Hindawi Publishing Corporation, Biochemistry Research International, vol. 2013, Article ID 730874, pp. 1-9.
Kim et al., "Generation of Human Induced Pluripotent Stem Cells by Direct Delivery of Reprogramming Proteins", Cell Stem Cell, Jun. 5, 2009, vol. 4, No. 6, pp. 472-476.
Kisselbach et al., "CD90 Expression on Human Primary Cells and Elimination of Contaminating Fibroblasts from Cell Cultures", Cytotechnology, 2009, pp. 31-44, vol. 59.
Kooijmans et al., "PEGylated and Targeted Extracellular Vesicles Display Enhanced Cell Specificity and Circulation Time", Journal of Controlled Release, 2016, vol. 224, pp. 77-85.
Kühn et al., "Periostin Induces Proliferation of Differentiated Cardiomyocytes and Promotes Cardiac Repair", Nature Medicine, Aug. 2007, vol. 13, No. 8, pp. 962-969.
Kutschka et al., "Collagen Matrices Enhance Survival of Transplanted Cardiomyoblasts and Contribute to Functional Improvement of Ischemic Rat Hearts", Circulation, Jul. 4, 2006, vol. 114, pp. I167-I173.
Kwon et al., "Cellular Manipulation of Human Embryonic Stem Cells by TAT-PDX1 Protein Transduction," Molecular Therapy, Jul. 1, 2005, vol. 12, No. 1, pp. 28-32.
Kyrtatos et al., "Magnetic Tagging Increases Delivery of Circulating Progenitors in Vascular Injury", Journal of the American College of Cardiology: Cardiovascular Interventions, 2009, pp. 794-802, vol. 2, No. 8.
Laflamme et al., "Cardiomyocytes Derived from Human Embryonic Stem Cells in Pro-Survival Factors Enhance Function of Infarcted Rat Hearts", Nature Biotechnology, Sep. 2007, vol. 25, No. 9, pp. 1015-1024.
Lai et al., "Exosome Secreted by MSC Reduces Myocardial Ischemia/Reperfusion Injury", Stem Cell Research, 2010, vol. 4, No. 3, pp. 214-222.
Landázuri et al., "Complexation of Retroviruses with Charged Polymers Enhances Gene Transfer by Increasing the Rate that Viruses are Delivered to Cells", The Journal of Gene Medicine, 2004, vol. 6, pp. 12, pp. 1304-1319.
Lapchak et al., "Intravenous Xenogeneic Human Cardiosphere-Derived Cell Extracellular Vesicles (Exosomes) Improves Behavioral Function in Small-Clot Embolized Rabbits", Experimental Neurology, vol. 307, Sep. 2018, pp. 109-117.
Lavon et al., "Derivation of Euploid Human Embryonic Stem Cells from Aneuploid Embryos", Stem Cells, 2008, vol. 26, pp. 1874-1882.
Lee et al., "Antibody Targeting of Stem Cells to Infarcted Myocardium", Stem Cells: Translational and Clinical Research, 2007, pp. 712-717, vol. 25.
Lee et al., "Cardiac Gene Transfer by Intracoronary Infusion of Adenovirus Vector-Mediated Reporter Gene in the Transplanted Mouse Heart", The Journal of Thoracic and Cardiovascular Surgery, 1996, pp. 246-252, vol. 111.
Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.
Leferovich et al., "Heart Regeneration in Adult MRL Mice", Proceedings of the National Academy of Sciences of the United States of America (PNAS), Aug. 14, 2001, vol. 98, No. 17, pp. 9830-9835.
Leor, MD, et al., "Transplantation of Fetal Myocardial Tissue Into the Infarcted Myocardium of Rat", Circulation, Nov. 1, 1996, vol. 94, No. 9, II-332-II-336.

(56) References Cited

OTHER PUBLICATIONS

Levenberg at al., "Endothelial Cells Derived from Human Embryonic Stem Cells", Proceedings of the National Academy of Sciences of the United States of America (PNAS), Developmental Biology, Apr. 2, 2002, pp. 4391-4396, vol. 99, No. 7.

Levine et al., "Vitamin C Pharmacokinetics in Healthy Volunteers: Evidence for a Recommended Dietary Allowance", Proceedings of the National Academy of Sciences of the United States of America, Apr. 1996, vol. 93, pp. 3704-3709.

Li et al., "Cardiospheres Recapitulate a Niche-Like Microenvironment Rich in Stemness and Cell-Matrix Interactions, Rationalizing Their Enhanced Functional Potency for Myocardial Repair", Stem Cells: Translational and Clinical Research, 2010, pp. 2088-2098, vol. 28.

Li et al., "Direct Comparison of Different Stem Cell Types and Subpopulations Reveals Superior Paracrine Potency and Myocardial Repair Efficacy with Cardiosphere-Derived Cells", Journal of American College of Cardiology, 2012, vol. 59, No. 10, pp. 942-953.

Li et al., "Expansion of Human Cardiac Stem Cells in Physiological Oxygen Improves Cell Production Efficiency and Potency for Myocardial Repair", Cardiovascular Research, Jul. 29, 2010, pp. 1-9.

Li et al., "IL-6 Contributes to the Defective Osteogenesis of Bone Marrow Stromal Cells from the Vertebral Body of the Glucocorticoid-Induced Osteoporotic Mouse", PLoS ONE, Apr. 29, 2016, vol. 11, No. 4, pp. 19.

Li et al., "Late-Breaking Basic Science Abstracts From the American Heart Association's Scientific Sessions 2009", Late-Breaking Basic Science Oral Abstracts: Translational Studies, Molecular, Cellular, and Functional Phenotypes of Human Cardiac Stem Cells Dependent Upon Monolayer Versus Three-Dimensional Culture Conditions, Abstract 5173, Circulation Research, Dec. 4, 2009, vol. 105, No. 12, pp. e56-e62.

Li et al., "Molecular, Cellular, and Functional Phenotypes of Human Cardiac Stem Cells Dependent Upon Monolayer Versus Three-Dimensional Culture Conditions", Circulation Research, Dec. 4, 2009, Abs. 5173, vol. 105, No. 12, p. e58.

Li et al., "Physiological Levels of Reactive Oxygen Species Are Required to Maintain Genomic Stability in Stem Cells", Stem Cell, Stem Cell Technology: Epigenetics, Genomics, Proteomics, and Metabonomics, May 4, 2010, vol. 28, pp. 1178-1185.

Li, MD, PhD et al., "Imaging Survival and Function of Transplanted Cardiac Resident Stem Cells", Journal of the American College of Cardiology, Apr. 7, 2009, vol. 53, No. 14, pp. 1229-1240.

Liao et al., "Enhanced Efficiency of Generating Induced Pluripotent Stem (IPS) Cells from Human Somatic Cells by a Combination of Six Transcription Factors", Cell Research, 2008, vol. 18, pp. 600-603.

Lin et al., "Accelerated Growth and Prolonged Lifespan of Adipose Tissue-Derived Human Mesenchymal Stem Cells in a Medium Using Reduced Calcium and Antioxidants", Stem Cells and Development, 2005, vol. 14, pp. 92-102.

Lindsay, Mark A., "Peptide-Mediated Cell Delivery: Application in Protein Target Validation", Current Opinion in Pharmacology, 2002, vol. 2, pp. 587-594.

Lindsley et al., "The PI3K/Akt Pathway: Recent Progress in the Development of ATP-Competitive and Allosteric Akt Kinase Inhibitors", Current Cancer Drug Targets, 2008, vol. 8, pp. 7-18.

Lipinski et al., "Impact of Intracoronary Cell Therapy on Left Ventricular Function in the Setting of Acute Myocardial Infarction: A Collaborative Systematic Review and Meta-Analysis of Controlled Clinical Trials", Journal of the American College of Cardiology, 2007, vol. 50, No. 18, pp. 1761-1767.

Liu et al. "Autologous Stem Cell Transplantation for Myocardial Repair", American Journal of Physiology, Heart and Circulatory Physiology, 2004, pp. H501-H511, vol. 287.

Liu et al., "Osteochondral Defect Repair with Autologous Bone Marrow-Derived Mesenchymal Stem Cells in an Injectable, In Situ, Cross-Linked Synthetic Extracellular Matrix", Tissue Engineering, 2006, pp. 3405-3416, vol. 12, No. 12.

Liu et al., "The Immunogenicity and Immune Tolerance of Pluripotent Stem Cell Derivatives", Frontiers in Immunology, Jun. 2017, vol. 3, No. 645, pp. 1-6.

Lowry et al., "Generation of Human Induced Pluripotent Stem Cells from Dermal Fibroblasts", Proceedings of the National Academy of Sciences of the United States of America (PNAS), Feb. 26, 2008, vol. 105, No. 8, pp. 2883-2888.

Lum et al., "The New Face of Bispecific Antibodies: Targeting Cancer and Much More", Experimental Hematology, 2006, pp. 1-6, vol. 34.

Lyngbaek et al., "Cardiac Regeneration by Resident Stem and Progenitor Cells in the Adult Heart", Basic Research in Cardiology, 2007, vol. 102, pp. 101-114.

Maitra et al, Genomic Alterations in Cultured Human Embryonic Stem Cells, Nature Genetics, Oct. 2005, vol. 37, No. 10, pp. 1099-1103.

Makkar et al., "Intracoronary Cardiosphere-Derived Cells for Heart Regeneration After Myocardial Infarction (CADUCEUS): A Prospective, Randomised Phase 1 Trial", Lancet, Mar. 10, 2012, vol. 379, pp. 895-904.

Maletic-Savatic et al., "Differential Spatiotemporal Expression of $K^+$ Channel Polypeptides in Rat Hippocampal Neurons Developing In Situ and In Vitro", The Journal of Neuroscience, May 1995, vol. 15, No. 5, pp. 3840-3851.

Malliaras et al., "Intracoronary Cardiosphere-Derived Cells After Myocardial Infarction", Journal of the American College of Cardiology, 2014, vol. 63, No. 2, pp. 110-121.

Mangi et al., "Mesenchymal Stem Cells Modified with Akt Prevent Remodeling and Restore Performance of Infarcted Hearts," Nature Medicine, Sep. 2003, vol. 9, No. 9, pp. 1195-1201.

Marbán, Eduardo, "Big Cells, Little Cells, Stem Cells: Agents of Cardiac Plasticity", Circulation Research, 2007, vol. 100, No. 4, pp. 445-446.

Marshall et al., "The Jellyfish Green Fluorescent Protein: A New Tool for Studying Ion Channel Express and Function", Neuron, Feb. 1995, vol. 14, pp. 211-215.

Martens et al., "Percutaneous Cell Delivery Into the Heart Using Hydrogels Polymerizing In Situ", Cell Transplantation, 2009, vol. 18, No. 3, pp. 297-304.

Matsumura, Tsuyoshi, "Cardiaphal Association in Muscular Dystrophy", Nanbyo To Zaitaku Care (Intractable Diseases and Home Care), 2013, vol. 19, No. 8, pp. 55-57.

Matsuura et al., "Adult Cardiac Sca-1-positive Cells Differentiate into Beating Cardiomyocytes", The Journal of Biological Chemistry, Mar. 19, 2004, vol. 279, No. 12, pp. 11384-11391.

McGann et al., "Mammalian Myotube Dedifferentiation Induced by Newt Regeneration Extract", Proceedings of the National Academy of Sciences of the United States of America (PNAS), Nov. 20, 2001, vol. 98, No. 24, pp. 13699-13704.

Mehmel et al., "The Linearity of the End-Systolic Pressure-Volume Relationship in Man and its Sensitivity for Assessment of Left Ventricular Function", Circulation, 1981, vol. 63, pp. 1216-1222.

Messina et al., "Isolation and Expansion of Adult Cardiac Stem Cells from Human and Murine Heart", Oct. 29, 2004, Circulation Research, Cellular Biology, American Heart Association, vol. 95, pp. 911-921.

Middleton et al., "Newt Cells Secrete Extracellular Vesicles with Therapeutic Bioactivity in Mammalian Cardiomyocytes", Journal of Extracellular Vesicles, 2018, vol. 7, pp. 1-15.

Miller III, et al., Meta-Analysis: High-Dosage Vitamin E Supplementation May Increase All-Cause Mortality, Annals of Internal Medicine, 2005, vol. 142, pp. 37-46.

Miltenyi et al., "High Gradient Magnetic Cell Separation With MACS[1]", Cytometry, 1990, pp. 231-238, vol. 11.

Mitsui et al., "The Homeoprotein Nanog is Required for Maintenance of Pluripotency in Mouse Epiblast and ES Cells", Cell, May 30, 2003, vol. 113, No. 5, pp. 631-642.

Miyazono et al. "Latent High Molecular Weight Complex of Transforming Growth Factor β1", May 5, 1988, vol. 263, No. 13, pp. 6407-6415.

(56) References Cited

OTHER PUBLICATIONS

Montessuit et al., "Regulation of Glucose Transporter Expression in Cardiac Myocytes: p38 MAPK is a Strong Inducer of GLUT4", Cardiovascular Research, Oct. 1, 2004, vol. 64, No. 1, pp. 94-104.
Montessuit et al., "Retinoic Acids Increase Expression of GLUT4 in Dedifferentiated and Hypertrophied Cardiac Myocytes", Basic Research in Cardiology, Jan. 1, 2006, vol. 101, No. 1, pp. 27-35.
Moss et al., "Conservation of the Heterochronic Regulator Lin-28, its Developmental Expression and MicroRNA Complementary Sites", Developmental Biology, 2003, vol. 258, No. 2, pp. 432-442.
Moss, M.D., et al., Prophylactic Implantation of a Defibrillator in Patients with Myocardial Infarction and Reduced Ejection Fraction, The New England Journal of Medicine, Mar. 21, 2002, vol. 346, No. 12, pp. 877-883.
Murata et al., "C4d Deposition and Cellular Infiltrates as Markers of Acute Rejection in Rat Models of Orthotopic Lung Transplantation", Transplantation, Jul. 15, 2008, vol. 86, No. 1, pp. 123-129.
Nadal-Ginard et al, "Myocyte Death, Growth, and Regeneration in Cardiac Hypertrophy and Failure", Circulation Research, 2003, vol. 92, pp. 139-150.
Nadal-Ginard et al., "A Matter of Life and Death: Cardiac Myocyte Apoptosis and Regeneration", Journal of Clinical Investigation, May 2003, vol. 111, No. 10, pp. 1457-1459.
Naito-Matsui, Yuko, "Lack of Neu5Gc Expression Contributes to the Severity of Duchenne Muscular Dystrophy in Humans", Trends in Glycoscience and Glycotechnology, 2011, vol. 23, No. 132, pp. 194-196.
Naka et al., "Regulation of Reactive Oxygen Species and Genomic Stability in Hematopoietic Stem Cells", Antioxidants & Redox Signaling, 2008, vol. 10, No. 11, pp. 1883-1894.
Nakagawa et al., "Generation of Induced Pluripotent Stem Cells without Myc from Mouse and Human Fibroblasts", Nature Biotechnology, Jan. 2008, vol. 26, No. 1, pp. 101-106.
Nakasa et al., "Acceleration of Muscle Regeneration by Local Injection of Muscle-Specific MicroRNAs in Rat Skeletal Muscle Injury Model", Journal of Cellular and Molecular Medicine, 2010, vol. 14, No. 10, pp. 2495-2505.
Nelson et al., "CXCR4+/FLK-1+ Biomarkers Select a Cardiopoietic Lineage from Embryonic Stem Cells", Stem Cells, 2008, vol. 26, pp. 1464-1473.
Nelson, MD, PhD et al., "Repair of Acute Myocardial Infarction with iPS Induced by Human Stemness Factors", Circulation, Aug. 4, 2009, vol. 120, No. 5, pp. 408-416.
Niethammer et al., "A Tissue-Scale Gradient of Hydrogen Peroxide Mediates Rapid Wound Detection in Zebrafish", Nature, Jun. 18, 2009, vol. 459, pp. 996-999.
Noguchi et al., "Protein Transduction Technology: A Novel Therapeutic Perspective", Acta Medica Okayama, 2006, vol. 60, No. 1, pp. 1-11.
North et al., "The Intersection Between Aging and Cardiovascular Disease", Circulation Research, Apr. 13, 2012, pp. 1097-1108.
Nussbaum et al., "Transplantation of Undifferentiated Murine Embryonic Stem Cells in the Heart: Teratoma Formation and Immune Response", The FASEB Journal, Research Communication, May 2007, vol. 21, No. 7, pp. 1345-1357.
Odelberg et al., "Dedifferentiation of Mammalian Myotubes Induced by msx1", Cell, Dec. 22, 2000, vol. 103, No. 7, pp. 1099-1109.
Odelberg, Shannon J., Inducing Cellular Dedifferentiation: A Potential Method for Enhancing Endogenous Regeneration in Mammals., Seminars in Cell & Developmental Biology, 2002, vol. 13, No. 5, pp. 335-343.
Offord et al., "Photoprotective Potential of Lycopene, -Carotene, Vitamin E, Vitamin C and Carnosic in UVA-Irradiated Human Skin Fibroblasts", Free Radical Biology & Medicine, 2002, vol. 32, No. 12, pp. 1293-1303.
Oh et al., "Cardiac Muscle Plasticity in Adult and Embryo by Heart-Derived Progenitor Cells", Annals of the New York Academy of Sciences, 2004, vol. 1015, pp. 182-189.
Oh et al., "Cardiac Progenitor Cells from Adult Myocardium: Homing, Differentiation, and Fusion After Infarction", Proceedings of the National Academy of Sciences of the United States of America (PNAS), Oct. 14, 2003, pp. 12313-12318, vol. 100, No. 21.
Okita et al., Generation of Mouse Induced Pluripotent Stem Cells Without Viral Vectors, Nov. 7, 2008, Science, vol. 322, pp. 949-953.
Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, http://circ.ahajournals.org/content/132/Suppl_3/A13881.short.
Owusu-Ansah et al., "Reactive Oxygen Species Prime *Drosophila* Haematopoietic Progenitors for Differentiation", Nature, Sep. 24, 2009, vol. 461, pp. 537-541.
Park et al., "Reprogramming of Human Somatic Cells to Pluripotency with Defined Factors", Nature, Jan. 10, 2008, vol. 451, pp. 141-146.
Passier et al., "Stem-Cell-Based Therapy and Lessons from the Heart", May 15, 2008, Nature, vol. 453, pp. 322-329.
Passier et al., "Origin and Use of Embryonic and Adult Stem Cells in Differentiation and Tissue Repair", Cardiovascular Research, 2003, vol. 58, No. 2, pp. 324-335.
Payne, Anthony G., "Using Immunomagnetic Technology and Other Means to Facilitate Stem Cell Homing", Medical Hypotheses, 2004, pp. 718-720, vol. 62.
Peterson, MD, MPH, et al., "Risk Stratification After Myocardial Infarction", Annals of Internal Medicine, 1997, vol. 126, No. 7, pp. 561-582.
Pike et al., "Heparin-Regulated Release of Growth Factors In Vitro and Angiogenic Response In Vivo to Implanted Hyaluronan Hydrogels Containing VEGF and bFGF," Biomaterials, 2006, vol. 27, pp. 5242-5241.
Piper et al. "Determinants of Cardiomyocyte Development in Long-Term Primary Culture", Journal of Molecular and Cellular Cardiology, 1988, vol. 20, pp. 825-835.
Plotnikov et al., "Biological Pacemaker Implanted in Canine Left Bundle Branch Provides Ventricular Escape Rhythms that Have Physiologically Acceptable Rates", Circulation, 2004, vol. 109, pp. 506-512.
Potapova et al., "Enhanced Recovery of Mechanical Function in the Canine Heart by Seeding an Extracellular Matrix Patch with Mesenchymal Stem Cells Committed to a Cardiac Lineage", American Journal of Physiology-Heart and Circulatory Physiology, 2008, vol. 295, pp. H2257-H2263.
Prestwich et al., "The Translational Imperative: Making Cell Therapy Simple and Effective", Acta Biomaterialia, 2012, vol. 8, pp. 4200-4207.
Prunier et al., "Delayed Erythropoietin Therapy Reduces Post-MI Cardiac Remodeling Only at a Dose that Mobilizes Endothelial Progenitor Cells", American Journal of Physiology-Heart and Circulatory Physiology, 2007, vol. 292, pp. H522-H529.
Puceat, Michel, "Role of Rac-GTPase and Reactive Oxygen Species in Cardiac Differentiation of Stem Cell", Antioxidants & Redox Signaling, 2005, vol. 7, No. 11 & 12, pp. 1435-1439.
Qin et al., "ATM-Mediated Transcriptional Elevation of Prion in Response to Copper-Induced Oxidative Stress", The Journal of Biological Chemistry, Feb. 13, 2009, vol. 284, No. 7, pp. 4582-4593.
Quaini et al., "Chimerism of the Transplanted Heart", The New England Journal of Medicine, Jan. 3, 2002, vol. 346, No. 1, pp. 5-15.
Quevedo et al., "Allogeneic Mesenchymal Stem Cells Restore Cardiac Function in Chronic Ischemic Cardiomyopathy via Trilineage Differentiating Capacity", Proceedings of the National Academy of Sciences of the United States of America (PNAS), Aug. 18, 2009, vol. 106, No. 33, pp. 14022-14027.
Rajasekaran et al., "Human αB-Crystallin Mutation Causes Oxido-Reductive Stress and Protein Aggregation Cardiomyopathy in Mice", Cell, 2007, vol. 130, No. 3, pp. 427-439.
Ranghino et al., "Endothelial Progenitor Cell-Derived Microvesicles Improve Neovascularization in a Murine Model of Hindlimb Ischemia", International Journal of Immunopathology and Pharmacology, 2012, vol. 25, No. 1, pp. 75-85.
Reiffel, James A., MD, FACC, "Ten Pearls for the Use of Antiarrhythmic Drugs for Atrial Fibrillation", Aug. 17, 2012, Retrieved

(56) References Cited

OTHER PUBLICATIONS from http://www.acc.org/latest-in-cardiology/articles/2014/07/18/15/12/ten-pearls-for-the-use-of-antiarrhythmic-drugs-for-atrial-fibrillation, pp. 17.

Riazifar et al., "Stem Cell Extracellular Vesicles: Extended Messages of Regeneration", Reviews in Advance, Oct. 19, 2016, vol. 14, No. 1, pp. 1-30.

Ribera, Angeles B., "Homogeneous Development of Electrical Excitability via Heterogeneous Ion Channel Expression", The Journal of Neuroscience, Feb. 1, 1996, vol. 16, No. 3, pp. 1123-1130.

Risebro et al., "Hand1 Regulates Cardiomyocyte Proliferation Versus Differentiation in the Developing Heart", Development, Nov. 2006, vol. 133, No. 22, pp. 4595-4606.

Rogers et al., "Intravenous Delivery of Cardiosphere-Derived Cells Improves Striated Muscle Function and Structure in a Murine Model of Duchenne Muscular Dystrophy", The FASEB Journal, Apr. 22-26, 2017, vol. 31, No. S1, pp. 3.

Rossi et al., "Deficiencies in DNA Damage Repair Limit the Function of Haematopoietic Stem Cells with Age", Nature, Jun. 7, 2007, vol. 447, pp. 725-729.

Rotwein et al., "Organization and Sequence of the Human Insulin-Like Growth Factor I Gene", The Journal of Biological Chemistry, Apr. 15, 1986, vol. 261, No. 11, pp. 4828-4832.

Rubio et al., "Spontaneous Human Adult Stem Cell Transformation", Cancer Research, 2005, vol. 65, pp. 3035-3039.

Rücker-Martin et al., "Dedifferentiation of Atrial Myocytes During Atrial Fibrillation: Role of Fibroblast Proliferation in Vitro", Cardiovascular Research, 2002, vol. 55, pp. 38-52.

Rudy, B. "Diversity and Ubiquity of K Channels", Neuroscience, 1988, vol. 25, No. 3, pp. 729-749.

Saito et al., "Cell Death Caused by Selenium Deficiency and Protective Effect of Antioxidants", The Journal of Biological Chemistry, Oct. 10, 2003, vol. 278, No. 41, pp. 39428-39434.

Sareen et al., Chromosome 7 and 19 Trisomy in Cultured Human Neural Progenitor Cells, PLoS One, Oct. 2009, vol. 4, No. 10, e7630, pp. 12.

Sasano et al., "Molecular Ablation of Ventricular Tachycardia after Myocardial Infarction", Natural Medicine, 2006, vol. 12, No. 11, pp. 1256-1258.

Sasano et al., "Ventricular Tachycardia from the Healed Myocardial Infarction Scar: Validation of an Animal Model and Utility of Gene Therapy", Heart Rhythm, Aug. 2009, vol. 6, No. 8, pp. S91-S97.

Scaria et al., "Host-Virus Genome Interactions: Marco Roles for MicroRNAs", Cellular Microbiology, 2007, vol. 9, No. 12, pp. 2784-2794.

Seifried et al., "A Review of the Interaction Among Dietary Antioxidants and Reactive Oxygen Species", Journal of Nutritional Biochemistry, 2007, vol. 18, pp. 567-579.

Sempere et al., Expression Profiling of Mammalian MicroRNAs Uncovers a Subset of Brain-Expressed MicroRNAs with Possible Roles in Murine and Human Neuronal Differentiation, Genome Biology, 2004, vol. 5, No. 3, pp. R13.1-R13.11.

Serôdio et al., "Cloning of a Novel Component of A-Type K+ Channels Operating at Subthreshold Potentials With Unique Expression in Heart and Brain", Journal of Neurophysiology, May 1996, vol. 75, No. 5, pp. 2174-2179.

Sert et al., "The Radioprotective Effect of Vitamins C, E and Vitamin E + Glutathione on the Small Intestine and the Thyroid Gland in Rats Irradiated with X-Rays", Turkish Journal of Medical Sciences, 2000, vol. 30, pp. 417-425.

Sesso, ScD, MPH, et al., "Vitamins E and C in the Prevention of Cardiovascular Disease in Men: The Physicians' Health Study II Randomized Controlled Trial", The Journal of the American Medical Association (JAMA), 2008, vol. 300, pp. 2123-2133.

Sharkey et al., "Stage-Specific Expression of Cytokine and Receptor Messenger Ribonucleic Acids in Human Preimplantation Embryos", 1995, Biology of Reproduction, 1995, vol. 53, pp. 955-962.

Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.

Shen et al. "Isolation of an Insulin-Like Growth Factor II cDNA with a Unique 5' Untranslated Region from Human Placenta", Mar. 1988, Proceedings of the National Academy of Sciences of the United States of America (PNAS), vol. 85, pp. 1947-1951.

Shenje et al., "Lineage Tracing of Cardiac Explant Derived Cells", PLoS One, Apr. 2008, vol. 3, No. 4, e1929, pp. 10.

Shi et al., "3,3'-Diindolylmethane Stimulates Exosomal Wnt11 Autocrine Signaling in Human Umbilical Cord Mesenchymal Stem Cells to Enhance Wound Healing", Theranostics, 2017, vol. 7, No. 6, pp. 1674-1688.

Shimizu et al., "Fabrication of Pulsatile Cardiac Tissue Grafts Using a Novel 3-D Cell Sheet Manipulation Techniques and Temperature-Responsive Cell Culture Surfaces", Circulation Research, 2002, vol. 90, No. 3, pp. 1-10.

Shu et al., "Disulfide-Crosslinked Hyaluronan-Gelatin Hydrogel Films: A Covalent Mimic of the Extracellular Matrix for In Vitro Cell Growth", Biomaterials, 2003, vol. 24, pp. 3825-3834.

Sigma-Aldrich, Inc., "Nutrient Mixture F12 Ham Kaighn's Modification (F12K)", Product Description, May 2007, pp. 2.

Simpson et al., "A Tissue Engineering Approach to Progenitor Cell Delivery Results in Significant Cell Engraftment and Improved Myocardial Remodeling", Stem Cells, Sep. 2007, vol. 25, No. 9, pp. 2350-2357.

Singh, PhD, Jai Pal, "Enabling Technologies for Homing and Engraftment of Cells for Therapeutic Applications", JACC: Cardiovascular Interventions, Aug. 2009, vol. 2, No. 8, pp. 803-804.

Singh, et al. "High-Dose α-Tocopherol Therapy Does Not Affect HDL Subfractions in Patients with Coronary Artery Disease on Statin Therapy", Clinical Chemistry, 2007, vol. 53, No. 3, pp. 525-528.

Slaughter, MD et al., "Clinical Management of Continuous-Flow Left Ventricular Assist Devices in Advanced Heart Failure", The Journal of Heart and Lung Transplantation, Apr. 2010, vol. 29, No. 4S, pp. S1-39.

Smart et al., "De Novo Cardiomyocytes from Within the Activated Adult Heart After Injury", Nature, Jun. 30, 2011, vol. 474, pp. 640-646.

Smith, PhD et al., "Stem Cells in the Heart: What's the Buzz all About? Part 1: Preclinical Considerations", Heart Rhythm, May 2008, vol. 5, No. 5, pp. 749-757.

Smith, PhD et al., "Stem Cells in the Heart: What's the Buzz all About? Part 2: Arrhythmic Risks and Clinical Studies", Heart Rhythm, Jun. 2008, vol. 5, No. 6, pp. 880-887.

Smith et al., "Regenerative Potential of Cardiosphere-Derived Cells Expanded From Percutaneous Endomyocardial Biopsy Specimens", Circulation, Feb. 5, 2007, pp. 896-908, vol. 115.

Smith et al., "Unique Phenotype of Cardiospheres Derived from Human Endomyocardial Biopsies", Circulation, Supplement II, Oct. 25, 2005, pp. 2, vol. 112, No. 17.

Smith et al., "Unselected Human Cardiosphere-derived Cells are Functionally Superior to c-Kit- or CD90-Purified Cardiosphere-Derived Cells", Circulation, Supplement 2, Oct. 28, 2008, vol. 118, No. 17, p. 1.

Smits, Anke Maria, "Cell-Based Cardiac Repair", Thesis, Utrecht University, The Netherlands, 2009, pp. 180.

Srivastava et al., "Thymosin β4 Is Cardioprotective after Myocardial Infarction", Annals of the New York Academy of Sciences, Sep. 2007, vol. 1112, pp. 161-170. Abstract only.

Stańczyk, et al., "The Effect of Vitamin C and Glutathione on Ethanol Cytotoxicity and Selected Parameters of Pro- and Antioxidative Processes in Mouse Fibroblasts 3T3-L1", Polish Journal of Environmental Studies, 2005, vol. 15, No. 1, pp. 131-137.

Stewart et al. "Revision of the 1990 Working Formulation for the Standardization of Nomenclature in the Diagnosis of Heart Rejection", The Journal of Heart and Lung Transplantation, 2005, vol. 24, No. 11, pp. 1710-1720.

Stull et al., "Chronic Treatment With Allopurinol Boosts Survival and Cardiac Contractility in Murine Postischemic Cardiomyopathy", Circulation Research, Cellular Biology, Nov. 12, 2004, pp. 1005-1011.

(56) References Cited

OTHER PUBLICATIONS

Sussman, Mark A., "Myocardial Aging and Senescence: Where Have the Stem Cells Gone?" Annual Review of Physiology, 2004, vol. 66, pp. 29-48.
Takahashi et al., "Induction of Pluripotent Stem Cells from Adult Human Fibroblasts by Defined Factors," Cell, vol. 131, Nov. 30, 2007, pp. 861-872.
Takahashi et al., "Induction of Pluripotent Stem Cells from Fibroblast Cultures, Nature Protocols", 2007, vol. 2 No. 12, pp. 3081-3089.
Takeda et al., "Human Oct3 Gene Family: cDNA Sequences, Alternative Splicing, Gene Organization, Chromosomal Location, and Expression at Low Levels in Adult Tissues", Nucleic Acids Research, 1992, vol. 20, No. 17, pp. 4613-4620.
Ueno et al., "Biphasic Role for Wnt/β-Catenin Signaling in Cardiac Specification in Zebrafish and Embryonic Stem Cells", Proceedings of the National Academy of Sciences of the United States of America (PNAS), Jun. 5, 2007, vol. 104, No. 23, pp. 9685-9690.
Ulloa-Montoya et al., "Culture Systems for Pluripotent Stem Cells", Journal of Bioscience and Bioengineering, 2005, vol. 100, No. 1, pp. 12-27.
Urbanek et al., "Cardiac Stem Cells Possess Growth Factor Receptor Systems That After Activation Regenerate the Infarcted Myocardium, Improving Ventricular Function and Long-term Survival", Circulation Research, 2005, vol. 97, pp. 663-673.
Urbanek et al., "Intense Myocyte Formation from Cardiac Stem Cells in Human Cardiac Hypertrophy", Proceedings of the National Academy of Sciences of the United States of America (PNAS), Sep. 2, 2003, vol. 100, No. 18, pp. 10440-10445.
Urbanek et al., Myocardial Regeneration by Activation of Multipotent Cardiac Stem Cells in Ischemic Heart Failure, Proceedings of the National Academy of Sciences of the United States of America (PNAS), Jun. 14, 2005, vol. 102, No. 24, pp. 8692-8697.
Van Der Geest et al., "Quantification in Cardiac MRI", Journal of Magnetic Resonance Imaging, 1999, vol. 10, pp. 602-608.
Van Gent et al., "Chromosomal Stability and the DNA Double-Stranded Break Connection", Nature, Mar. 2001, vol. 2, pp. 196-206.
Van Vliet et al., "Progenitor Cells Isolated from the Human Heart: a Potential Cell Source for Regenerative Therapy", Netherlands Heart Journal, May 2008, vol. 16, No. 5, pp. 163-169.
Van Winkle et al, "Cardiogel: A Biosynthetic Extracellular Matrix for Cardiomyocyte Culture", In Vitro Cellular & Developmental Biology—Animal, Sep. 1996, vol. 21, pp. 478-485.
Vela et al., "Quest for the Cardiovascular Holy Grail: Mammalian Myocardial Regeneration", Cardiovascular Pathology, 2008, vol. 17, No. 1-5.
Ventura et al., "Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts", The Journal of Biological Chemistry, May 11, 2007, vol. 282, No. 19, pp. 14243-14252.
Von Harsdorf, R., "Can Cardiomyocytes Divide?" Heart, 2001, vol. 86, pp. 481-482.
Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.
Wagner, Richard, "The State of the Art in Antisense Research", Nature Medicine, Nov. 1995, vol. 1, No. 11, pp. 1116-1118.
Walder et al., "Up-Regulation of Neural Stem Cell Markers Suggests the Occurrence of Dedifferentiation in Regenerating Spinal Cord", Development Genes and Evolution, 2003, vol. 213, pp. 625-630.
Walravens et al., "Cardiosphere-Derived Cell and Mesenchymal Stem Cell Extracellular Vesicles Contain Distinct RNA Cargo", Scientific Program, ISEV2017, Dec. 2017, p. 173.
Wang et al., "Establishment of New Mouse Embryonic Stem Cell Lines is Improved by Physiological Glucose and Oxygen", Cloning and Stem Cells, 2006, vol. 8, No. 2, pp. 108-116.
Wang et al. "The LIM Domain Homeobox Gene isl-1: Conversation of Human, Hamster, and Rat Complementary Deoxyribonucleic Acid Sequences and Expression in Cell Types of Non-neuroendocrine Lineage", Endocrinology, 1994, vol. 134, No. 3, pp. 1416-1422.
Wernig el al., "c-Myc Is Dispensable for Direct Reprogramming of Mouse Fibroblasts", Cell Stem Cell, Jan. 2008, vol. 2, pp. 10-12.
White et al. "Intrinsic Cardiac Origin of Human Cardiosphere-Derived Cells", European Heart Journal, 2013, vol. 34, pp. 68-75.
Wilmut et al., "Viable Offspring Derived from Fetal and Adult Mammalian Cells", Nature, Feb. 27, 1997, vol. 385, pp. 810-813.
Wilson et al., "Bioluminescence Reporter Gene Imaging of Human Embryonic Stem Cell Survival, Proliferation, and Fate", Methods in Molecular Biology, 2009, vol. 574, pp. 87-103.
Wong et al., "Loss of the Y Chromosome: An Age-Related or Clonal Phenomenon in Acute Myelogenous Leukemia/Myelodysplastic Syndrome?" Archives of Pathology & Laboratory Medicine, Aug. 2008, vol. 132, pp. 1329-1332.
Wu et al., "Cellular Therapy and Myocardial Tissue Engineering: The Role of Adult Stem and Progenitor Cells", European Journal of Cardio-Thoracic Surgery, 2006, vol. 30, pp. 770-781.
Wu et al., "Cell Delivery in Cardiac Regenerative Therapy", Ageing Research Reviews, 2012, vol. 11, pp. 32-40.
Yamada et al., "Type V Collagen-Induced Oral Tolerance Plus Low-Dose Cyclosporine Prevents Rejection of MHC Class I and II Incompatible Lung Allografts", The Journal Immunology, Jul. 1, 2009, vol. 183, No. 1, pp. 237-245.
Yang et al., "Human Cardiovascular Progenitor Cells Develop from a $KDR^+$ Embryonic-Stem-Cell-Derived Population", Nature, May 22, 2008, vol. 453, pp. 524-528.
Yau MD et al., "Beneficial Effect of Autologous Cell Transplantation on Infarcted Heart Function: Comparison Between Bone Marrow Stromal Cells and Heart Cells", The Annals of Thoracic Surgery, 2003, vol. 75, No. 1, pp. 169.
Yee et al. "Allogenic Cardiospheres Delivered via Percutaneous Transendocardial Injection Increase Viable Myocardium, Decrease Scar Size, and Attenuate Cardiac Dilation in Porcine Ischemic Cardiomyopathy", PLOS One, Dec. 2, 2014, pp. 1-29.
Yu et al., "Induced Pluripotent Stem Cell Lines Derived from Human Somatic cells," Science, Dec. 21, 2007, vol. 318, pp. 1917-1920.
Yu et al., "miR-221 and miR-222 Promote Schwann Cell Proliferation and Migration by Targeting LASS2 after Sciatic Nerve Injury", Journal of Cell Science, Jan. 25, 2012, vol. 125, No. 11, pp. 2675-2683.
Zammit et al., "The Skeletal Muscle Satellite Cell: Stem Cell or Son of Stem Cell?" Differentiation, 2001, vol. 68, pp. 193-204.
Zha et al., "Complementary Functions of ATM and H2AX in Development and Suppression of Genomic Instability", Proceedings of the National Academy of Sciences of the United States of America (PNAS), Jul. 8, 2008, vol. 105, No. 27, pp. 9302-9306.
Zhang et al., "Do Cardiac Stem Cells Arise from Cardiomyocyte Dedifferentiation?" Circulation Research, Nov. 2006, vol. 99, No. 11, p. 1278. Abstract only.
Zhao et al., "Targeting Human $CD34^+$ Hematopoietic Stem Cells With Anti-CD45 x Anti-Myosin Light-Chain Bispecific Antibody Preserves Cardiac Function in Myocardial Infarction", Journal of Applied Physiology, Feb. 21, 2008, pp. 1793-1800, vol. 104.
Zhou et al., "Down-Regulation of microRNA-26a Promotes Mouse Hepatocyte Proliferation During Liver Regeneration", PLoS ONE, Apr. 2012, vol. 7, No. 4, e33577, pp. 1-7.
Zhou et al., "Generation of Induced Pluripotent Stem Cells Using Recombinant Proteins", Cell Stem Cell, May 1, 2009, vol. 4, No. 5, pp. 381-384.
Zuo et al., Assessment of Myocardial Blood Perfusion Improved by CD151 in a Pig Myocardial Infarction Model, Acta Pharmacologica Sinica, Jan. 2009, vol. 30, No. 1, pp. 70-77.
International Search Report and Written Opinion received in PCT Application No. PCT/US2017/013054, dated May 23, 2017 in 12 pages.

(56) References Cited

OTHER PUBLICATIONS

International Preliminary Report on Patentability and Written Opinion received in PCT/US2017/013054, dated Jul. 26, 2018 in 9 pages.

* cited by examiner

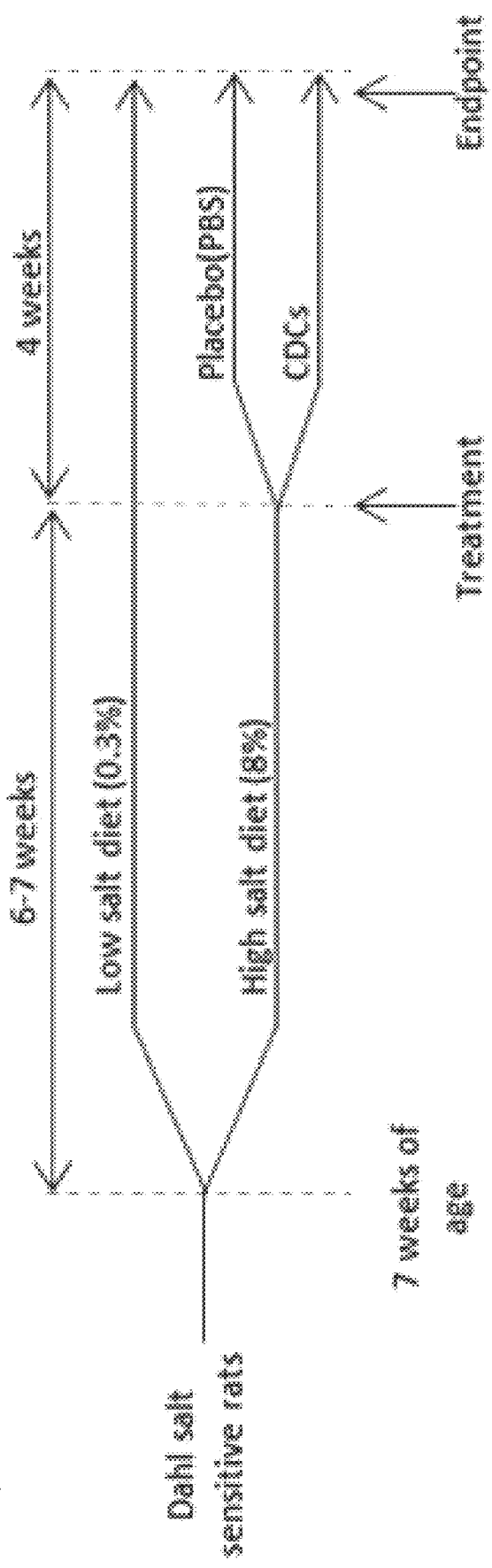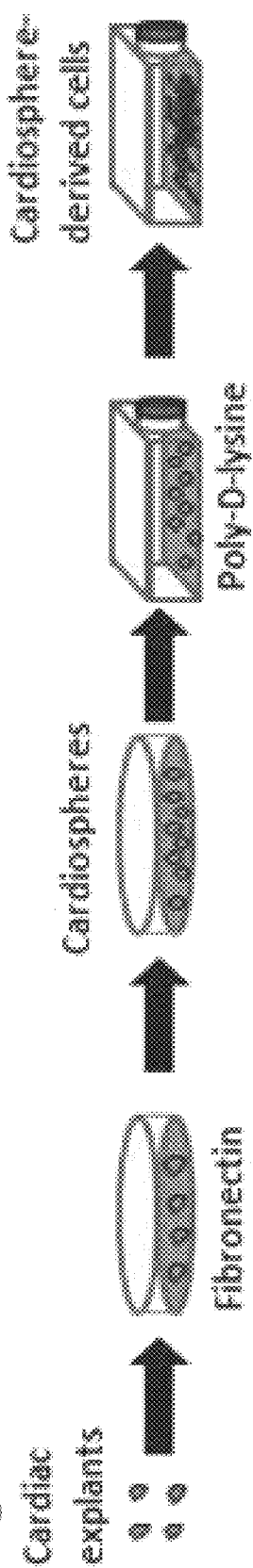
Fig. 1A
Fig. 1B

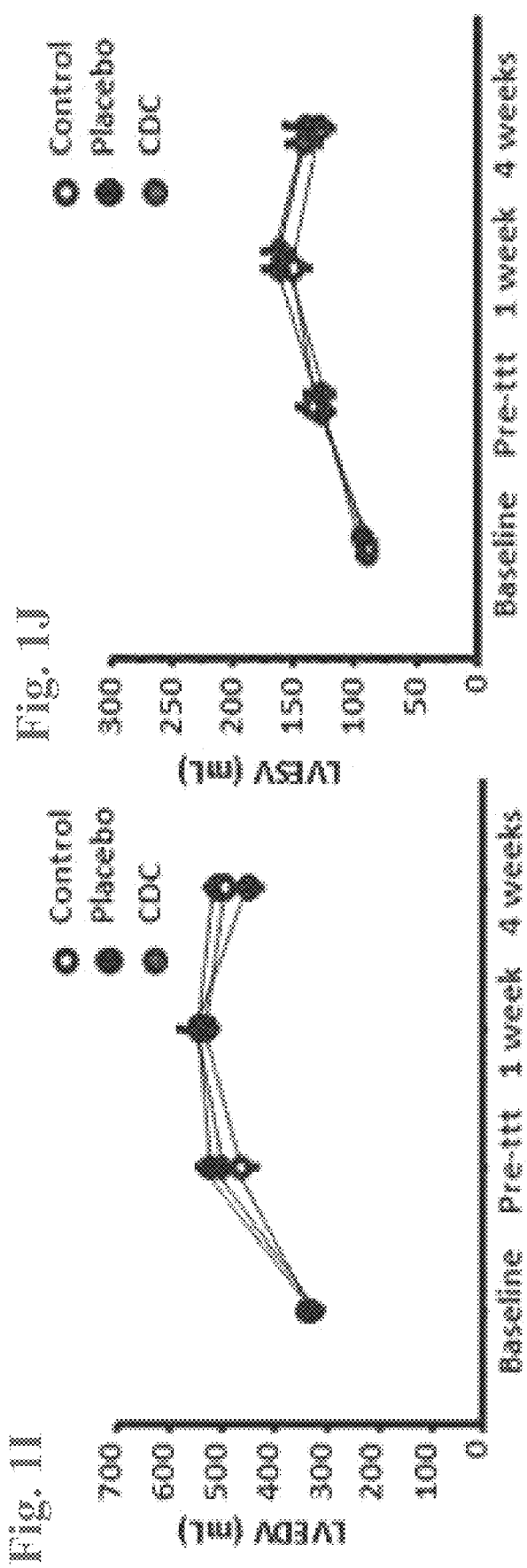

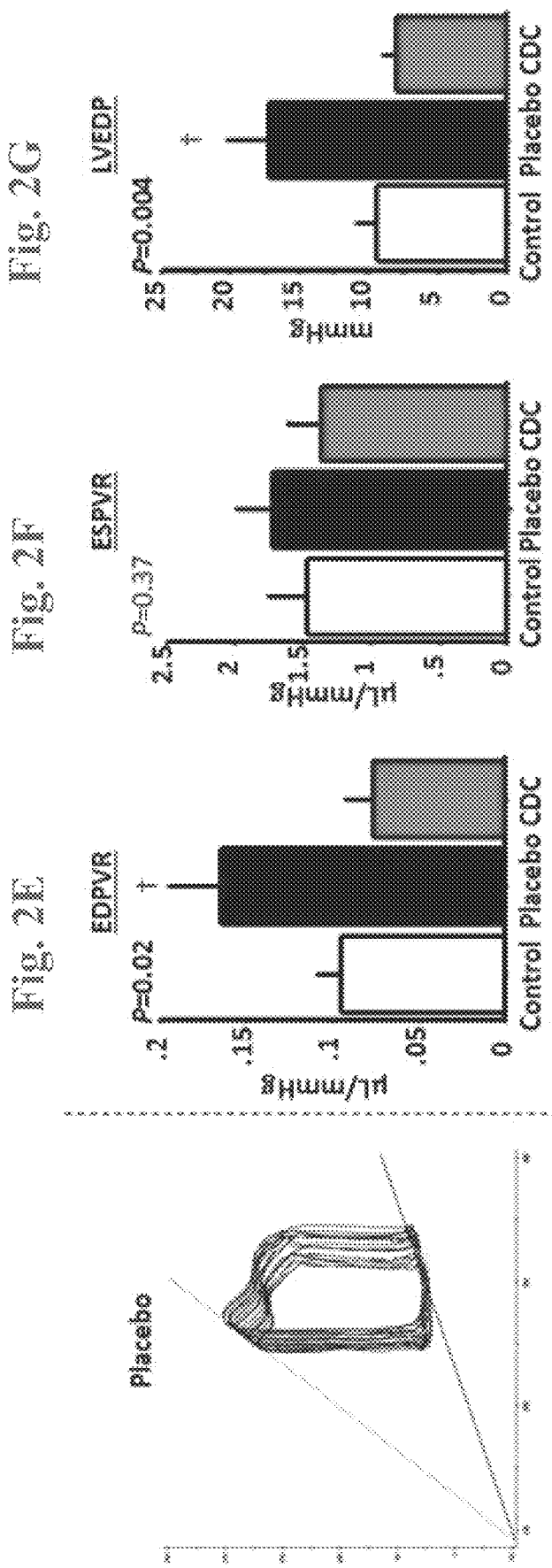

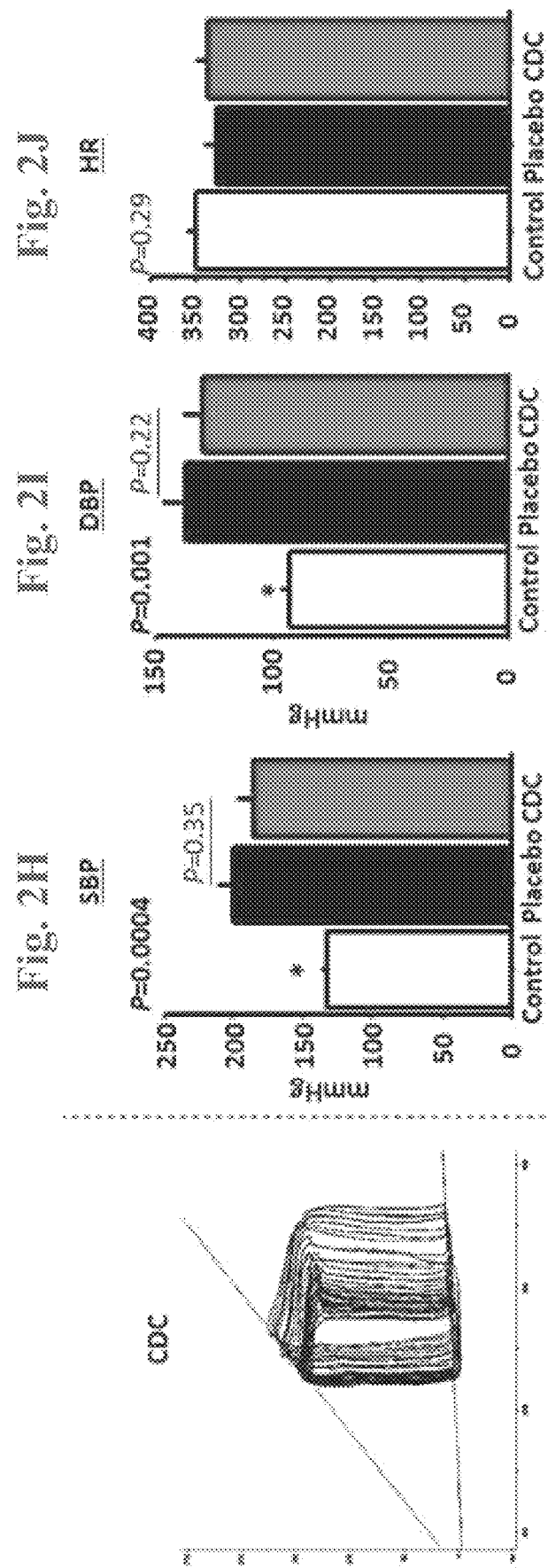

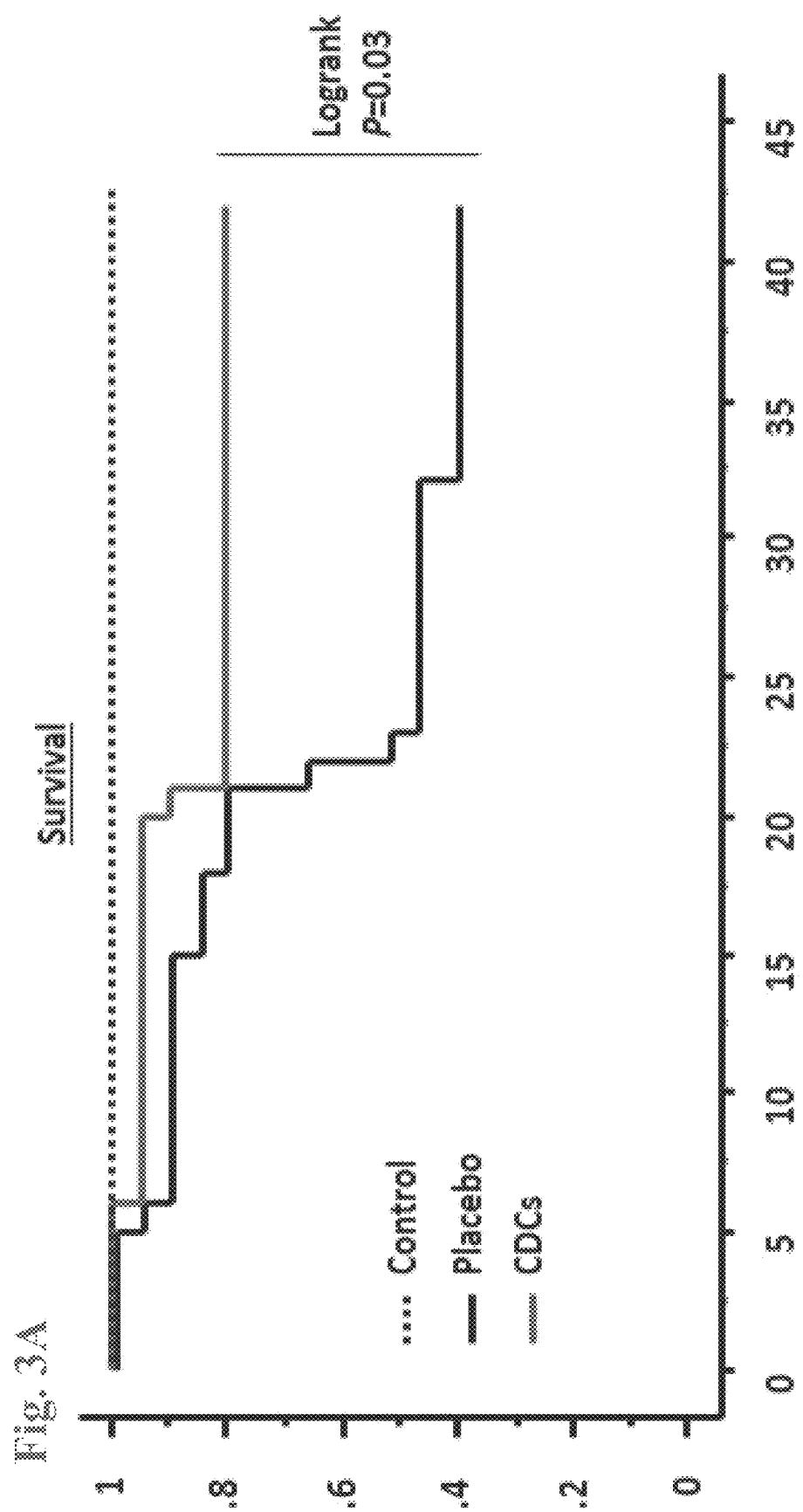

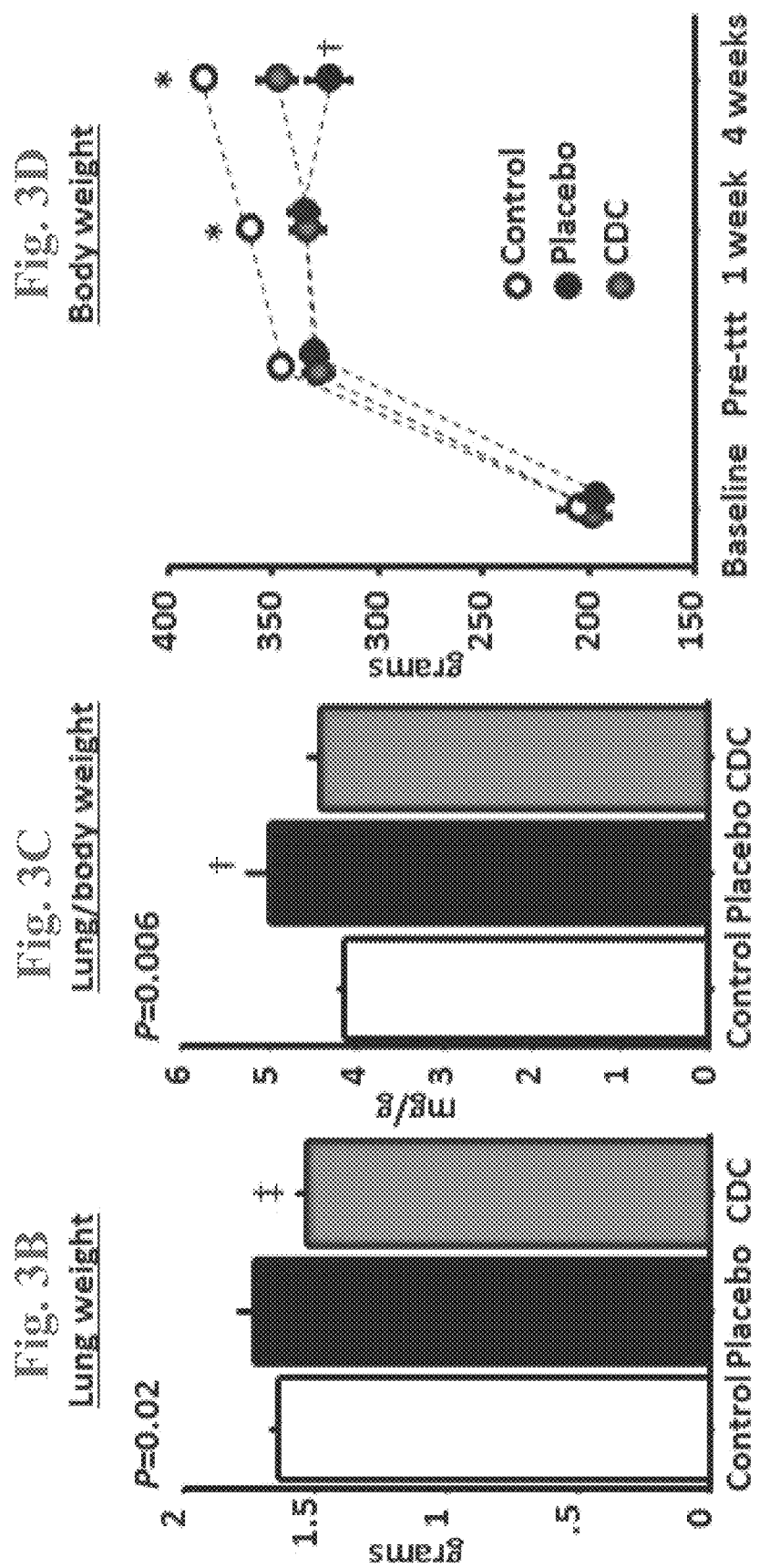

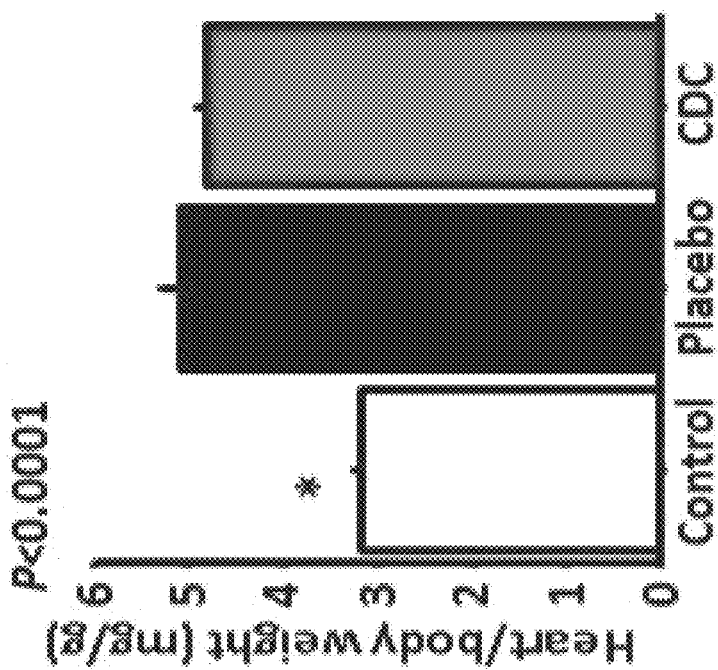
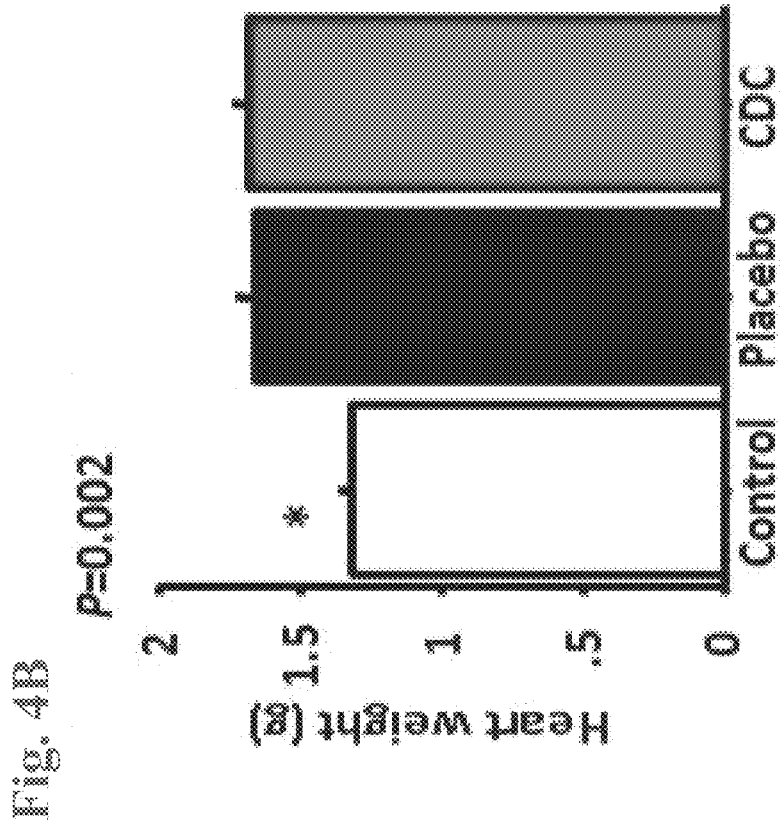
Fig. 4B

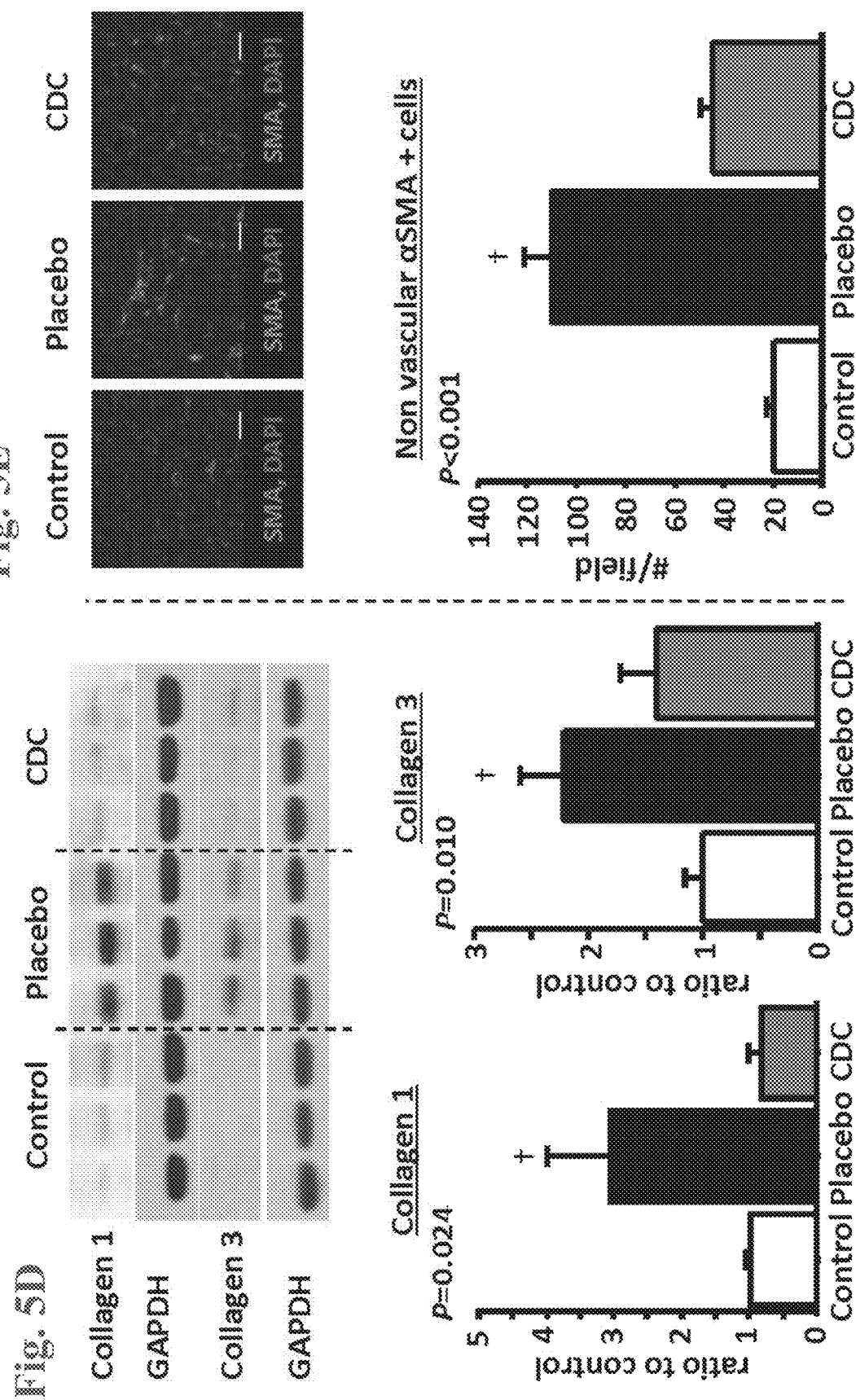

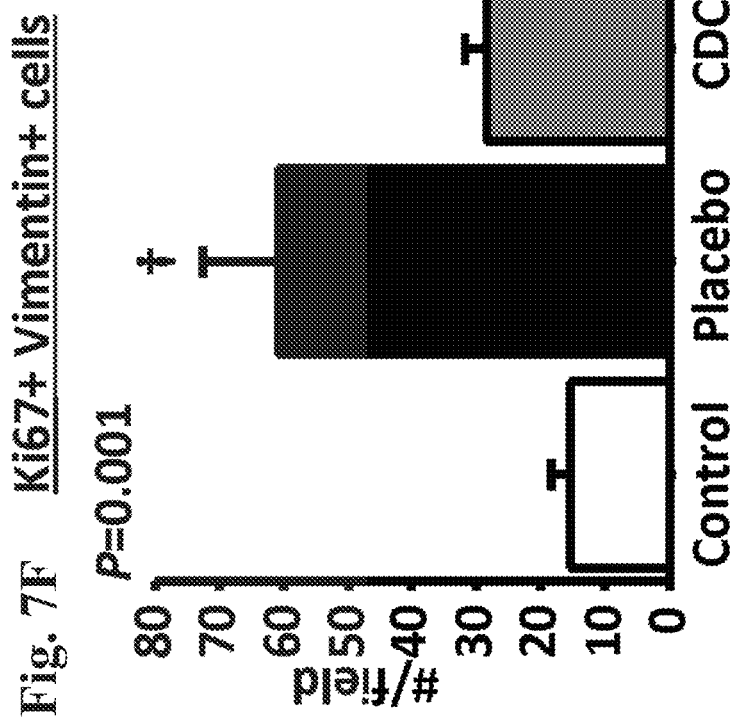
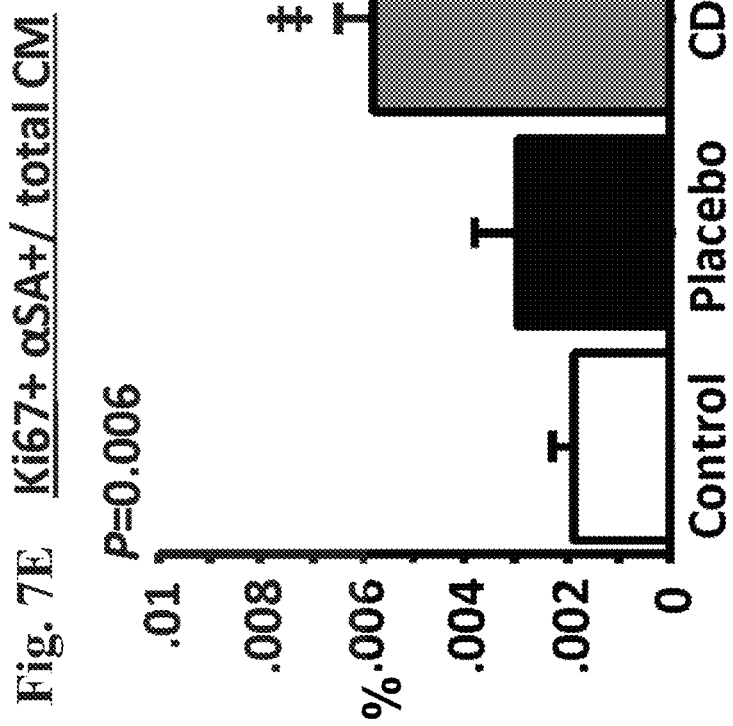

CARDIOSPHERE-DERIVED CELLS AND EXOSOMES SECRETED BY SUCH CELLS IN THE TREATMENT OF HEART FAILURE WITH PRESERVED EJECTION FRACTION

CROSS REFERENCE TO RELATED APPLICATIONS

The present application is a division of U.S. patent application Ser. No. 16/066,014, filed Jun. 25, 2018, which is a U.S. National Phase entry under 35 U.S.C. § 371 of International Patent Application No. PCT/US2017/013054, filed Jan. 11, 2017, which claims the benefit of priority to U.S. Provisional Patent Application No. 62/277,359, filed Jan. 11, 2016, the entirety of each of which is hereby incorporated by reference herein. Any and all applications for which a foreign or domestic priority claim is identified in the Application Data Sheet as filed with the present application are hereby incorporated by reference under 37 CFR 1.57.

STATEMENT REGARDING FEDERALLY-SPONSORED RESEARCH

This invention was made with government support under HL083109 awarded by the National Institutes of Health. The government has certain rights in the invention.

FIELD OF THE INVENTION

Described herein are methods and compositions related to use of cells and their exosomes in regenerative medicine application for cardiac disease.

BACKGROUND

Half of patients with heart failure (HF) have a preserved left ventricular ejection fraction. Sometimes referred to as diastolic HF, heart failure with preserved ejection fraction (HFpEF) represents ~50% of heart failure worldwide. Disability and frequent hospitalization are hallmarks of the disease. Associated comorbidities are common and notably include hypertension, diabetes, and obesity. Women are affected more frequently than men (by as much as a 2:1 preponderance). Unlike heart failure with reduced ejection fraction (HFrEF), where numerous pharmacological and device options have been proven to be effective, no treatments have been proven to reduce morbidity and mortality in HFpEF. The challenge of HFpEF is increasing as the population ages and comorbidities become more prevalent. The HFpEF hospitalization rate is now greater than that for heart failure with HFrEF. Compounding the problem is the fact that underlying pathophysiological mechanisms have not been completely elucidated.

Morbidity and mortality in HFpEF are similar to values observed in patients with HF and reduced ejection fraction (EF). However, HFpEF constitutes a distinct clinical syndrome refractory to routine medical approaches. No effective treatment has been identified and HFpEF has become a major public health concern. Its increasing prevalence, rising at a rate of ~1% per year, now exceeds that of heart failure with reduced ejection fraction (HFrEF). Outcomes of HFpEF are poor, and, so far, no treatment has been shown to decrease morbidity or mortality. For example, treatment to date has focused on the renin-angiotensin-aldosterone system and the adrenergic nervous system, but clinical trials have failed to show any significant benefit to their blockade.

HFpEF, sometimes referred to as diastolic HF, is associated with various cardiovascular risk factors (especially hypertension), extra-cardiac comorbidities and aging. The net result is impaired diastolic relaxation and filling of the left ventricle (LV), increased myocardial stiffness, impaired vascular compliance and increased diastolic pressure. Perhaps underlying different responses to pharmacological intervention, HFpEF populations can consist of patients with limited myocardial infarction at risk for unfavorable eccentric LV remodeling. Cardiac hypertrophy indeed has little in common with limited myocardial infarction, and in both conditions, mechanisms driving LV remodeling are likely to be dissimilar. There is a great need in the art for therapeutic approaches for HFpEF.

SUMMARY OF THE INVENTION

Described herein is a method of treating heart failure with preserved ejection fraction, including administering a therapeutically effective amount of a composition including cardiosphere-derived cells (CDCs) to a subject in need of treatment for heart failure with preserved ejection fraction (HFpEF), thereby treating HFpEF in the subject. In various embodiments, the CDCs are allogeneic. In various embodiments, the CDCs are autologous.

In various embodiments, the composition includes about $10 \times 10^6$ to about $100 \times 10^6$ CDCs in a single dose. In various embodiments, treating HFpEF includes an improvement in cardiac performance. In various embodiments, the improvement in cardiac performance includes an improvement in early-to-late ventricular filling (E/A) ratio, left ventricle (LV) relaxation, LV end-diastolic pressure and/or lung congestion. In various embodiments, the improvement in cardiac performance includes a reduction in Tau and/or end-diastolic pressure volume relationship. In various embodiments, treating HFpEF includes a reduction in fibrosis. In various embodiments, the reduction in fibrosis includes a reduction in collagen expression. In various embodiments, collagen includes collagen 1A1 and collagen 3. In various embodiments, treating HFpEF includes a reduction in inflammation. In various embodiments, the reduction in inflammation includes a reduction in inflammatory cells. In various embodiments, the inflammatory cells are CD68+ and/or CD45+ cells. In various embodiments, the reduction in inflammation includes a reduction in inflammatory cytokines in serum. In various embodiments, the inflammatory cytokines are MCP-1, IL-6 and TNF-α. In various embodiments, treating HFpEF includes an increase in myocardial blood flow. In various embodiments, administering a therapeutically effective amount of a composition including CDCs to the subject is primary therapy. In various embodiments, administering a therapeutically effective amount of a composition including a plurality of CDCs to the subject is adjunctive to standard therapy for heart failure. In various embodiments, administering a composition consists of one or more of: intra-arterial infusion, intravenous infusion, and percutaneous injection.

Described herein is a method of treating heart failure with preserved ejection fraction, including administering a therapeutically effective amount of a composition including a plurality of exosomes isolated from cardiosphere-derived cells (CDCs) grown in serum-free media to a subject in need of treatment for heart failure with preserved ejection fraction (HFpEF), thereby treating HFpEF in the subject. In various embodiments, the plurality of exosomes comprise exosomes with a diameter of about 90 nm to about 200 nm and are CD81+, CD63+, or both. In various embodiments, treating HFpEF includes an improvement in cardiac performance. In various embodiments, the improvement in cardiac performance includes an improvement in early-to-late ventricular filling (E/A) ratio, left ventricle (LV) relaxation, LV end-diastolic pressure and/or lung congestion. In various embodiments, the improvement in cardiac performance includes a reduction in Tau and/or end-diastolic pressure volume relationship. In various embodiments, treating HFpEF includes a reduction in fibrosis. In various embodiments, treating HFpEF includes a reduction in inflammation. In various embodiments, administering a therapeutically effective amount of a composition including a plurality of exosomes to the subject is adjunctive to standard therapy for heart failure. In various embodiments, administering a therapeutically effective amount of a composition including a plurality of exosomes to the subject is adjunctive to standard therapy for heart failure.

BRIEF DESCRIPTION OF FIGURES

FIG. 3: CDC treatment improves survival (FIG. 3A) and pulmonary congestion (FIG. 3B, lung weight [left] and FIG. 3C, lung weight/body weight [right]) in rats with HFpEF. (FIG. 3D) At endpoint, body weight loss induced by HFpEF is partially restored by CDC treatment ((N=10 for controls, n=15-20 for placebo and CDC groups). Log-rank for CDC vs. placebo. *P<0.05 vs. placebo and CDC; †P<0.05 vs. control and CDC; ‡P<0.05 vs. placebo, all by ANOVA.

FIG. 5: (FIG. 5D) Collagen 1A1 and collagen 3 content is higher in placebo- than in CDC-treated and control rats. (FIG. 5E) Immunostaining for α-smooth muscle actin in control, placebo- and CDC-treated rats. Myofibroblast infiltration into the heart is higher in placebo- than in CDC-treated and control rats. (n=6-8 in each group). †P<0.05 vs. control and CDC by ANOVA.

FIG. 6.

FIG. 8.

FIG. 9.

FIG. 17.

DETAILED DESCRIPTION OF THE INVENTION

Figure 1D:
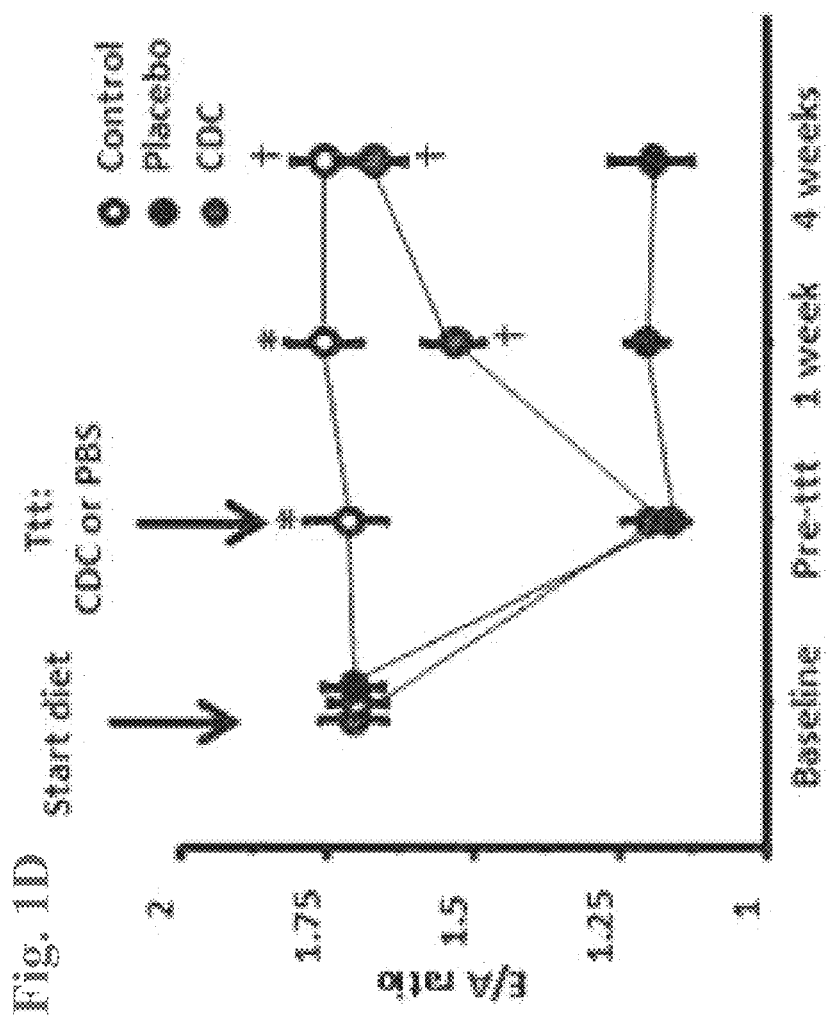
(FIG. 1D) CDC treatment normalizes E/A ratio at 4 weeks while placebo remains depressed. Systolic function assessed by LVEF (FIG. 1E and FIG. 1 F) and by fractional area change (FIG. 1G and FIG. 1H) is equivalent in all groups. LV end-diastolic (FIG. 1I) and end systolic volumes (FIG. 1J) are equivalent in all groups. CDC treatment halts HFpEF related left atrial enlargement while placebo does not. (Baseline and pre-treatment, n=10 for controls and n=24 for placebo and CDC; 1 week post treatment, n=10 for controls, n=21 for placebo and CDC; at endpoint, n=10 for controls, n=15 for placebo and n=18 for CDC). *P<0.05 vs. placebo and CDC; † for P<0.05 vs. placebo, both by ANOVA.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, NY 2006); Smith, *March's Advanced Organic Chemistry Reactions, Mechanisms and Structure* $7^{th}$ ed., J. Wiley & Sons (New York, NY 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

There is no clear pathophysiologic mechanism to HFpEF, but many elements of the cardiac, vascular, and renal systems have been implicated. Myocardial fibrosis and inflammation have been associated with HFpEF and with the transition from hypertensive LV hypertrophy without HFpEF to hypertensive LV hypertrophy with HFpEF. Here, the Inventors describe use of cardiosphere-derived cells (CDCs) and exosomes derived from CDCs (CDC-derived exosomes), which exhibit anti-fibrotic, anti-inflammatory and angiogenic properties. Positive factors exist in cellular exosomes produced by CDCs, the lipid bilayer nanovesicles secreted by cells when multivesicular endosomes fuse with the plasma membrane.

Described herein are compositions and methods demonstrating CDC and CDC-derived exosome disease-modifying activity in HFpEF. CDCs were capable of normalizing LV relaxation and LV diastolic pressure and improving survival in HFpEF despite persistent hypertension and hypertrophy. Lower risk of arrhythmias in HFpEF was also observed following CDC administration. Improvement of diastolic dysfunction following administration of CDC-derived exosomes was observed, along with decreased mortality. CDCs and CDC-derived exosomes are beneficial in the treatment of HFpEF.

HFpEF is a complex syndrome characterized by HF signs and symptoms and a normal or near-normal left ventricular ejection fraction (LVEF). More specifically, signs and symptoms of heart failure are present, including a decrease in left ventricular compliance, increased pressure at end-diastole in the left ventricle, increased left atrial pressure, but with an ejection fraction greater than 50%. Increased left atrial size is often seen with HFpEF as a result of the slow or incomplete left ventricular relaxation. Arrhythmias, including those affecting atrium (atrial fibrillation, AF) are coincident with HFpEF. A recent study found frequencies of preexisting and incident AF were 43.2% and 9.5%, respectively, in those with HFpEF. Ventricular dysfunction in HFpEF increases risk of imminently life-threatening ventricular fibrillation. The AHA staging system for HF can be applied to patients with HFpEF, to classify disease severity and to track the progression of the disease. Stage A are at high risk of developing HF, stage B includes patients with known structural disease, such as a history of myocardial infarction or systolic or diastolic dysfunction, but no overt symptoms of HF. Patients at Stage C have evidence of structural disease and symptoms of HF, such as fatigue, shortness of breath, or reduced exercise tolerance, with Stage D including refractory HF, with marked symptoms even at rest despite medical therapy.

In the absence of endocardial or pericardial disease, diastolic LV dysfunction results from increased myocardial stiffness. Myocardial diastolic stiffness of the extracellular matrix is determined by collagen through regulation of its total amount, relative abundance of collagen type I, and degree of cross-linking. In HFpEF patients, all three mechanisms appear to be involved, including excessive collagen type I deposition resulting from an imbalance between an exaggerated synthesis and a depressed degradation. In hypertensive patients with HFpEF, there is decreased matrix degradation because of downregulation of matrix metalloproteinases (MMPs) and upregulation of tissue inhibitors of matrix metalloproteinases (TIMPs). As a result, a characteristic feature of HFpEF is slow LV relaxation, which may reduce LV stroke volume, especially at high heart rates, whereas normal heart function, accelerates LV relaxation at high heart rates.

It is emphasized that HFpEF constitutes a distinct clinical syndrome refractory to routine medical approaches. Randomized clinical trials (RCTs), epidemiologic studies, and mechanistic studies in patients with chronic heart failure (HF) have generally divided HF into two clinical syndromes: HFrEF (EF<50%) and HFpEF (EF≥50%). All of these patients, regardless of EF, have the clinical syndrome of HF; nevertheless, distinct differences in several clinical and pathophysiologic features make HFpEF particularly challenging. Table 1 summarizes differences in structural and functional remodeling, molecular and cellular mechanisms, demographics and antecedent illnesses, and responsiveness to various classes of drugs. Note the utter lack of efficacy of the routine HF armamentarium. To date, because no management strategies have been demonstrated to decrease morbidity and mortality in HFpEF patients, HFpEF represents a critical unmet medical need.

HFpEF has proven refractory because so little is known about its pathophysiology and pathogenesis. There are two prevalent hypotheses for the pathogenesis of HFpEF. According to a first model, cardiac hypertrophy secondary to hypertension impairs relaxation and leads to HFpEF. If this first model is true, antihypertensive and antihypertrophic measures would be the key to treating HFpEF, but agents that act in this manner have failed in HFpEF clinical trials (Table 1).

TABLE 1

Differences Between HFpEF and HFrEF.

| Left Ventricle | HFpEF | HFrEF |
| --- | --- | --- |
| End Diastolic Volume (EDV) | ↔ | ↑ |
| End Systolic Volume (ESV) | ↔ | ↑ |
| Wall Thickness | ↑ | ↔ |
| LV Mass | ↑ | ↑ |
| Mass/EDV ratio | ↑ | ↓ |
| Remodeling | Concentric | Eccentric |
| Ejection Fraction (at rest) | ↔ | ↓ |
| Stroke Work (at rest) | ↔ | ↓ |
| End Systolic Elastance | ↔ | ↓ |
| Vascular Stiffness | ↑ | ↓ |
| End Diastolic Stiffness | ↑ | ↓ |
| Myocardial Ultrastructure | | |
| Cardiomyocyte Length | ↔ | ↑ |
| Cardiomyocyte Diameter | ↑ | ↔ |
| Remodeling | Concentric | Eccentric |
| Myocardial Fibrosis | Diffuse | Patchy, Focal |
| Effect on HF Hospitalization and CV Death | | |
| B-blockers | No Effect | Improved |
| Angiotensin Converting Enzyme Inhibitor (ACE-I) | No Effect | Improved |
| Angiotensin Receptor Blocker (ARB) | No Effect | Improved |
| Digitalis | No Effect | Improved |
| Hydralazine/Nitrates | No Effect | Improved |
| Mineralocorticoid Receptor Blocker (MRA) | Uncertain | Improved |
| PDE-5 Inhibitor | No Effect | Not Studied |

↔ = unchanged compared to control, ↑ = increased compared to control, ↓ = decreased compared to control A contrasting concept as a second model has emerged from several recent studies in animal models and humans that have implicated inflammation and collagen infiltration. Hypertension and other comorbidities can favor a pro-inflammatory state with high circulating cytokine levels, including IL-6, TNF-α and MCP-1. Inflammation leads to activation, recruitment and trans-endothelial migration of leukocytes and monocytes/macrophages into the heart. These inflammatory cells contribute to myocardial fibrosis by promoting the differentiation of fibroblasts into myofibroblasts with activation of the TGFβ pathway. The resulting increase in left ventricular (LV) collagen content is the main contributor to the increase in passive myocardial fiber stiffness, a major component of diastolic impairment in HFpEF. Abnormalities of calcium cycling and the myofilaments (e.g., cardiomyocyte remodeling) have been associated with hypertrophy and HFpEF, but a causal link with either model has not been solidly established. It is important to understand the nature and origin of the abnormalities in cardiomyocyte behavior in HFpEF, as these are the contractile cells of the heart and presumably underlie the central functional abnormalities.

Fibrosis occurs in both the heart and vascular system with impacts on both diastolic and systolic function leading to myocardial stiffening, retarded suction and filling, and the loss of early diastolic suction as mediated by alterations in the amount and composition of collagen within the extracellular matrix. It is understood that collagen synthesis is enhanced in the setting of increased load or activation of the renin-angiotensin-aldosterone system (RAAS), and it has further been observed that down-regulation of enzymes that degrade collagen occurs in patients with HFpEF. Additionally, in aldosterone-mediated fibrosis, stimulation of cardiac fibroblasts increases collagen synthesis and deposition, leading to myocardial fibrosis, increased LV stiffness, inflammation and oxidative stress. Animal models suggest that high dietary sodium intake in the setting of abnormal renal sodium handling may be a stimulus for the development and progression of HFpEF through increased oxidative stress, perivascular inflammation, and increased 'local' renal and cardiac angiotensin II and aldosterone.

The pathophysiology of HFpEF is fundamentally different from heart failure with reduced ejection fraction. Drugs used to treat heart failure with reduced ejection fraction are not effective in HFpEF and there are currently no effective treatments for HFpEF (Table 1). The Inventors have administered to patients with HFrEF, cardiosphere-derived cells (CDCs) that are capable of mediating therapeutic regeneration in humans as a candidate cell type for regenerative therapy. These heart-derived cells exhibit multilineage potential and clonogenicity, and work primarily through indirect mechanisms. These cells exert salutary anti-inflammatory and anti-fibrotic effects in HFrEF and by the secretion of nanovesicles called exosomes, which mediate cell-cell transfer of genetic payloads. As described herein, CDC-derived exosome therapy can provide broad benefit, based on several factors including superior dosage regimes (e.g., concentration, persistence in local tissue milieu, repeat dosages), and reduced or obviated safety concerns as non-viable entities. Particular advantages may be dramatic for those conditions that currently lack any treatment modality such as HFpEF.

The Inventors investigated whether allogeneic rat CDCs are able to decrease manifestations of HFpEF. Dahl salt-sensitive rats (DS rats) develop hypertension, hypertrophy and, eventually, HFpEF on a high-salt diet. Increased fibrosis and inflammation underlie the development of HFpEF, with resultant cachexia, pulmonary congestion and accelerated mortality. As described herein, the Inventors tested the efficacy of CDCs in improving LV structure and function and overall outcome in DS rats with HFpEF. CDCs improve LV structure and function and overall outcome. High-salt fed rats developed hypertension associated with left ventricular (LV) hypertrophy and diastolic dysfunction, without impairment of ejection fraction. Early-to-late ventricular filling (E/A) ratio returned to normal in CDC-treated rats and remained depressed in placebo. Tau and end-diastolic pressure volume relationship were higher in placebo-treated rats than in CDC-treated rats and control, and improved LV relaxation was also associated with lower LV end-diastolic pressure, decreased lung congestion and enhanced survival (80% vs. 48%) in CDC-treated rats. CDC treatment decreased LV fibrosis, including collagen 1A1 and 3 mRNA expression levels, decreased inflammatory infiltrates in the LV, and reduced serum inflammatory cytokines. Lower risk of arrhythmias in HFpEF was also observed following CDC administration. Improvement of diastolic dysfunction following administration of CDC-derived exosomes was observed, along with decreased mortality.

Cardiospheres

Cardiospheres are undifferentiated cardiac cells that grow as self-adherent clusters as described in WO 2005/012510, and Messina et al., "Isolation and Expansion of Adult Cardiac Stem Cells From Human and Murine Heart," Circulation Research, 95:911-921 (2004), the disclosures of which are herein incorporated by reference in their entirety.

Briefly, heart tissue can be collected from a patient during surgery or cardiac biopsy. The heart tissue can be harvested from the left ventricle, right ventricle, septum, left atrium, right atrium, crista terminalis, right ventricular endocardium, septal or ventricle wall, atrial appendages, or combinations thereof. A biopsy can be obtained, e.g., by using a percutaneous bioptome as described in, e.g., U.S. Patent Application Publication Nos. 2009/012422 and 2012/0039857, the disclosures of which are herein incorporated by reference in their entirety. The tissue can then be cultured directly, or alternatively, the heart tissue can be frozen, thawed, and then cultured. The tissue can be digested with protease enzymes such as collagenase, trypsin and the like. The heart tissue can be cultured as an explant such that cells including fibroblast-like cells and cardiosphere-forming cells grow out from the explant. In some instances, an explant is cultured on a culture vessel coated with one or more components of the extracellular matrix (e.g., fibronectin, laminin, collagen, elastin, or other extracellular matrix proteins). The tissue explant can be cultured for about 1, 2, 3, 4, or more weeks prior to collecting the cardiosphere-forming cells. A layer of fibroblast-like cells can grow from the explant onto which cardiosphere-forming cells appear. Cardiosphere-forming cells can appear as small, round, phase-bright cells under phase contrast microscopy. Cells surrounding the explant including cardiosphere-forming cells can be collected by manual methods or by enzymatic digestion. The collected cardiosphere-forming cells can be cultured under conditions to promote the formation of cardiospheres. In some aspects, the cells are cultured in cardiosphere-growth medium including buffered media, amino acids, nutrients, serum or serum replacement, growth factors including but not limited to EGF and bFGF, cytokines including but not limited to cardiotrophin, and other cardiosphere promoting factors such as but not limited to thrombin. Cardiosphere-forming cells can be plated at an appropriate density necessary for cardiosphere formation, such as about 20,000-100,000 cells/mL. The cells can be cultured on sterile dishes coated with poly-D-lysine, or other natural or synthetic molecules that hinder the cells from attaching to the surface of the dish. Cardiospheres can appear spontaneously about 2-7 days or more after cardiosphere-forming cells are plated.

Cardiosphere-Derived Cells (CDCs)

CDCs are a population of cells generated by manipulating cardiospheres in the manner as described in, e.g., U.S. Patent Application Publication No. 2012/0315252, the disclosures of which are herein incorporated by reference in their entirety. For example, CDCs can be generated by plating cardiospheres on a solid surface which is coated with a substance which encourages adherence of cells to a solid surface of a culture vessel, e.g., fibronectin, a hydrogel, a polymer, laminin, serum, collagen, gelatin, or poly-D-lysine, and expanding same as an adherent monolayer culture. CDCs can be repeatedly passaged, e.g., passaged two times or more, according to standard cell culturing methods.

Exosomes

Exosomes are vesicles formed via a specific intracellular pathway involving multivesicular bodies or endosomal-related regions of the plasma membrane of a cell. Exosomes can range in size from approximately 20-150 nm in diameter. In some cases, they have a characteristic buoyant density of approximately 1.1-1.2 g/mL, and a characteristic lipid composition. Their lipid membrane is typically rich in cholesterol and contains sphingomyelin, ceramide, lipid rafts and exposed phosphatidylserine. Exosomes express certain marker proteins, such as integrins and cell adhesion molecules, but generally lack markers of lysosomes, mitochondria, or caveolae. In some embodiments, the exosomes contain cell-derived components, such as but not limited to, proteins, DNA and RNA (e.g., microRNA and noncoding RNA). In some embodiments, exosomes can be obtained from cells obtained from a source that is allogeneic, autologous, xenogeneic, or syngeneic with respect to the recipient of the exosomes.

Certain types of RNA, e.g., microRNA (miRNA), are known to be carried by exosomes. miRNAs function as post-transcriptional regulators, often through binding to complementary sequences on target messenger RNA transcripts (mRNAs), thereby resulting in translational repression, target mRNA degradation and/or gene silencing. For example, as described in WO 2014/028493, miR146a exhibits over a 250-fold increased expression in CDCs, and miR210 is upregulated approximately 30-fold, as compared to the exosomes isolated from normal human dermal fibroblasts.

Exosomes derived from cardiospheres and CDCs are described in, e.g., WO 2014/028493, the disclosures of which are herein incorporated by reference in their entirety. Methods for preparing exosomes can include the steps of: culturing cardiospheres or CDCs in conditioned media, isolating the cells from the conditioned media, purifying the exosome by, e.g., sequential centrifugation, and optionally, clarifying the exosomes on a density gradient, e.g., sucrose density gradient. In some instances, the isolated and purified exosomes are essentially free of non-exosome components, such as components of cardiospheres or CDCs. Exosomes can be resuspended in a buffer such as a sterile PBS buffer containing 0.01-1% human serum albumin. The exosomes may be frozen and stored for future use.

Exosomes can be prepared using a commercial kit such as, but not limited to the ExoSpin™ Exosome Purification Kit, Invitrogen® Total Exosome Purification Kit, PureExo® Exosome Isolation Kit, and ExoCap™ Exosome Isolation kit. Methods for isolating exosome from stem cells are found in, e.g., Tan et al., Journal of Extracellular Vesicles, 2:22614 (2013); Ono et al., Sci Signal, 7(332):ra63 (2014) and U.S. Application Publication Nos. 2012/0093885 and 2014/0004601. Methods for isolating exosome from cardiosphere-derived cells are found in, e.g., Ibrahim et al., Stem Cell Reports, 2:606-619 (2014). Collected exosomes can be concentrated and/or purified using methods known in the art. Specific methodologies include ultracentrifugation, density gradient, HPLC, adherence to substrate based on affinity, or filtration based on size exclusion.

For example, differential ultracentrifugation has become a leading technique wherein secreted exosomes are isolated from the supernatants of cultured cells. This approach allows for separation of exosomes from nonmembranous particles, by exploiting their relatively low buoyant density. Size exclusion allows for their separation from biochemically similar, but biophysically different microvesicles, which possess larger diameters of up to 1,000 nm. Differences in flotation velocity further allows for separation of differentially sized exosomes. In general, exosome sizes will possess a diameter ranging from 30-200 nm, including sizes of 40-100 nm. Further purification may rely on specific properties of the particular exosomes of interest. This includes, e.g., use of immunoadsorption with a protein of interest to select specific vesicles with exoplasmic or outward orientations.

Among current methods, e.g., differential centrifugation, discontinuous density gradients, immunoaffinity, ultrafiltration and high performance liquid chromatography (HPLC), differential ultracentrifugation is the most commonly used for exosome isolation. This technique utilizes increasing centrifugal force from 2000×g to 10,000×g to separate the medium- and larger-sized particles and cell debris from the exosome pellet at 100,000×g. Centrifugation alone allows for significant separation/collection of exosomes from a conditioned medium, although it is insufficient to remove various protein aggregates, genetic materials, particulates from media and cell debris that are common contaminants. Enhanced specificity of exosome purification may deploy sequential centrifugation in combination with ultrafiltration, or equilibrium density gradient centrifugation in a sucrose density gradient, to provide for the greater purity of the exosome preparation (flotation density 1.1-1.2 g/mL) or application of a discrete sugar cushion in preparation.

Importantly, ultrafiltration can be used to purify exosomes without compromising their biological activity. Membranes with different pore sizes—such as 100 kDa molecular weight cut-off (MWCO) and gel filtration to eliminate smaller particles—have been used to avoid the use of a nonneutral pH or non-physiological salt concentration. Currently available tangential flow filtration (TFF) systems are scalable (to >10,000 L), allowing one to not only purify, but concentrate the exosome fractions, and such approaches are less time consuming than differential centrifugation. HPLC can also be used to purify exosomes to homogeneouslysized particles and preserve their biological activity as the preparation is maintained at a physiological pH and salt concentration.

Other chemical methods have exploit differential solubility of exosomes for precipitation techniques, addition to volume-excluding polymers (e.g., polyethylene glycols (PEGs)), possibly combined additional rounds of centrifugation or filtration. For example, a precipitation reagent, ExoQuick®, can be added to conditioned cell media to quickly and rapidly precipitate a population of exosomes, although re-suspension of pellets prepared via this technique may be difficult. Flow field-flow fractionation (FlFFF) is an elution-based technique that is used to separate and characterize macromolecules (e.g., proteins) and nano- to micro-sized particles (e.g., organelles and cells) and which has been successfully applied to fractionate exosomes from culture media.

Beyond these techniques relying on general biochemical and biophysical features, focused techniques may be applied to isolate specific exosomes of interest. This includes relying on antibody immunoaffinity to recognizing certain exosome-associated antigens. As described, exosomes further express the extracellular domain of membrane-bound receptors at the surface of the membrane. This presents a ripe opportunity for isolating and segregating exosomes in connections with their parental cellular origin, based on a shared antigenic profile. Conjugation to magnetic beads, chromatography matrices, plates or microfluidic devices allows isolating of specific exosome populations of interest as may be related to their production from a parent cell of interest or associated cellular regulatory state. Other affinity-capture methods use lectins which bind to specific saccharide residues on the exosome surface.

Described herein are compositions and methods providing significant benefits in the treatment of heart failure with preserved ejection fraction (HFpEF), including repair or regeneration of damaged or diseased tissues via CDCs and CDC-derived exosomes. Further examples and information are described in, for example, U.S. application Ser. Nos. 11/666,685, 12/622,143, 12/622,106, 14/421,355, PCT App. No. PCT/US2013/054732, PCT/US2015/053853, PCT/US2015/054301 and PCT/US2016/035561, which are fully incorporated by reference herein.

Described herein is a method for treatment for heart failure with preserved ejection fraction, including administering a therapeutically effective amount of cardiosphere-derived cells (CDCs) to a subject, thereby treating the subject. In other embodiments, the method for treatment for heart failure with preserved ejection fraction, includes administering a therapeutically effective amount of a composition including cardiosphere-derived cells (CDCs) to a subject, thereby treating the subject. In other embodiments, the method includes selecting a subject in need of treatment, and administering a composition including cardiosphere-derived cells (CDCs) to the subject, wherein administration of the composition treat the subject. In various embodiments, the method for treatment for heart failure with preserved ejection fraction includes identifying heart failure with preserved ejection fraction in a subject and administering a therapeutically effective amount of a composition including cardiosphere-derived cells (CDCs). In various embodiments, the method for treatment for heart failure with preserved ejection fraction includes treatment in a subject diagnosed with heart failure with preserved ejection fraction. In various embodiments, the method for treatment for heart failure with preserved ejection fraction includes treatment in a subject where standard therapy for heart failure has failed.

In various embodiments, HFpEF is characterized by one or more parameters including: unchanged end diastolic volume (EDV), unchanged end systolic volume (ESV), increased wall thickness, increased LV mass, increased mass/EDV ratio, concentric remodeling, unchanged ejection fraction (at rest), unchanged stroke work (at rest), unchanged end systolic elastance, increased vascular stiffness, and increased end diastolic stiffness and combinations thereof. One of ordinary skill in the art would know how to identify and/or diagnose HFpEF by considering any one or more of the aforementioned exemplary parameters. In other embodiments, HFpEF is characterized by one or more of: unchanged cardiomyocyte length, increased cardiomyocyte diameter, diffuse myocardial fibrosis, and combinations thereof. In various embodiments, HFpEF is refractory to treatment using any of B-blockers, Angiotensin Converting Enzyme Inhibitor (ACE-I), Angiotensin Receptor Blocker (ARB), Digitalis, Hydralazine/Nitrates, or PDE-5 Inhibitor. In other embodiments, CDCs are administered as a primary therapy. In certain embodiments, heart failure with preserved ejection fraction involves tissue damage or dysfunction. In other embodiments, heart failure with preserved ejection fraction involves fibrosis. In other embodiments, heart failure with preserved ejection fraction involves inflammation. In certain embodiments, CDCs are administered as adjuvant to standard therapy for HF.

In various embodiments, an effective dose of CDCs include $1\times10^5$ to $1\times10^6$ and $1\times10^6$ to $100\times10^6$ cells, such as between $10\times10^6$ and $50\times10^6$ cells. Depending on the size of the damaged region of the heart, more or less cells can be used. A larger region of damage may require a larger dose of cells, and a small region of damage may require a smaller dose of cells. On the basis of body weight of the recipient, an effective dose may be between 1 and $10\times10^6$ per kg of body weight, preferably between $1\times10^6$ and $5\times10^6$ cells per kg of body weight. Patient age, general condition, and immunological status may be used as factors in determining the dose administered. For example, it has been demonstrated that 3 mL/$3\times10^5$ CDCs, is capable of providing therapeutic benefit in intracoronary administration. In various embodiments, administration of the composition to the subject occurs through any of known techniques in the art.

In various embodiments, cardiosphere derived cells (CDCs) can be delivered systemically or locally to the heart. Local administration can be by catheter or during surgery. Systemic administration can be by intravenous or intraarterial injections, perfusion, or infusion. When the populations of cells of the invention are administered systemically, they migrate to the appropriate organ, e.g., the heart, if the cells are derived from resident heart stem cells. The beneficial effects which are observed upon administration of the cells to a mammal may be due to the cells per se, or due to products which are expressed by the cells. For example, it is possible that the engraftment of cells produces a favorable outcome. It is also possible that cytokines or chemokines or other diffusible factors stimulate resident cells to grow, reproduce, or perform better.

In other embodiments, myocardial infusion is used, for example, the use of intracoronary catheters. In various embodiments, delivery can be intra-arterial or intravenous. Additional delivery sites include any one or more compartments of the heart, such as myocardium, associated arterial, venous, and/or ventricular locations. In various embodiments, administration includes percutaneous delivery, and/or injection into heart. In certain embodiments, administration can include delivery to a tissue or organ site that is the same as the site of diseased and/or dysfunctional tissue. In certain embodiments, administration can include delivery to a tissue or organ site that is different from the site or diseased and/or dysfunctional tissue. In various embodiments, administration of the composition can include combinations of multiple delivery techniques, such as intravenous, intracoronary, and intramyocardial delivery.

In various embodiments, the composition alters gene expression in the damaged or dysfunctional tissue, improves viability of the damaged tissue, and/or enhances regeneration or production of new tissue in the individual. In various embodiments, administration of the composition results in functional improvement in the tissue. In certain embodiments, the damaged tissue is pulmonary, arterial or capillary tissue. In several embodiments, the damaged or dysfunctional tissue includes cardiac tissue.

In various embodiments, CDC treatment decreases fibrosis, including left ventricle fibrosis. In other embodiments, decreased fibrosis includes reduction in collagen 1A1 and 3 expression levels, such as protein and mRNA. In other embodiments, decreased fibrosis includes increased microvascular density. In various embodiments, CDC treatment reduces inflammation. In various embodiments, this includes reduction in inflammatory infiltrates, such as CD68+ and CD45+ cells in the left ventricle. In other embodiments, this includes reduction in inflammatory cytokines in serum, including for example MCP-1, IL-6 and TNF-α. In other embodiments, CDC treatment results in an increase in myocardial blood flow.

In various embodiments, CDCs lower risk of arrhythmias as can be exhibited, by for example, a lower arrhythmogenicity index and/or a decrease in action potential duration dispersion in the heart. In various embodiments, CDCs normalize left ventricle relaxation and diastolic pressure, improve survival, and/or confer functional benefits despite persistent hypertension and hypertrophy. For example, in certain embodiments in which pulmonary, arterial, capillary, or cardiac tissue is damaged or dysfunctional, functional improvement may include increased cardiac output, contractility, ventricular function and/or reduction in arrhythmia (among other functional improvements). For example, this may include a decrease in right ventricle systolic pressure. For other tissues, improved function may be realized as well, such as enhanced cognition in response to treatment of neural damage, improved blood-oxygen transfer in response to treatment of lung damage, improved immune function in response to treatment of damaged immunological-related tissues.

Described herein is a method of treatment for heart failure with preserved ejection fraction, including administering a therapeutically effective amount of plurality of exosomes to a subject, thereby treating the subject. In other embodiments, a method of treatment for heart failure with preserved ejection fraction, includes administering a therapeutically effective amount of a composition including a plurality of exosomes to a subject, thereby treating the subject. In various embodiments, the method includes selecting a subject in need of treatment and administering a composition including a plurality of exosomes to the subject, wherein administration of the composition treats the subject.

In various embodiments, the method for treatment for heart failure with preserved ejection fraction includes identifying heart failure with preserved ejection fraction in a subject and administering a therapeutically effective amount of a composition including a plurality of exosomes. In various embodiments, the method for treatment for heart failure with preserved ejection fraction includes treatment in a subject diagnosed with heart failure with preserved ejection fraction. In various embodiments, the method for treatment for heart failure with preserved ejection fraction includes treatment in a subject where standard therapy for heart failure has failed.

In various embodiments, the plurality of the exosomes are isolated from cardiosphere-derived cells (CDCs) grown in serum-free media, include exosomes with a diameter of about 90 nm to about 200 nm and are CD81+, CD63+, or both.

In various embodiments, HFpEF is characterized by one or more parameters including: unchanged end diastolic volume (EDV), unchanged end systolic volume (ESV), increased wall thickness, increased LV mass, increased mass/EDV ratio, concentric remodeling, unchanged ejection fraction (at rest), unchanged stroke work (at rest), unchanged end systolic elastance, increased vascular stiffness, and increased end diastolic stiffness and combinations thereof. One of ordinary skill in the art would know how to identify and/or diagnose HFpEF by considering any one or more of the aforementioned exemplary parameters. In other embodiments, HFpEF is characterized by one or more of: unchanged cardiomyocyte length, increased cardiomyocyte diameter, diffuse myocardial fibrosis, and combinations thereof. In various embodiments, HFpEF is refractory to treatment using any of B-blockers, Angiotensin Converting Enzyme Inhibitor (ACE-I), Angiotensin Receptor Blocker (ARB), Digitalis, Hydralazine/Nitrates, or PDE-5 Inhibitor. In other embodiments, CDCs are administered as a primary therapy. In certain embodiments, CDC-derived exosomes are administered as adjuvant to standard therapy for HF.

In other embodiments, the method of treatment includes modulation of fibrosis and/or inflammation. In other embodiments, administering a composition includes about 1 to about 100 mg exosome protein in a single dose. In other embodiments, a single dose is administered multiple times to the subject. In other embodiments, administering a composition includes injection. In other embodiments, the injection includes percutaneous injection. In other embodiments, the injection is directly into heart muscle. In other embodiments, administering a composition includes myocardial infusion. In other embodiments, myocardial infusion is intra-arterial or intravenous. In other embodiments, treatment of the subject results in decreased fibrosis, decreased inflammation, increased mitochondrial function and/or increased cardiomyogenesis. In other embodiments, decreased fibrosis includes a reduction in collagen accumulation. In other embodiments, collagen includes collagen I and/or collagen III. In other embodiments, decreased inflammation includes an increase in cytoplasmic nuclear factor (erythroid-derived 2)-like 2 (Nrf2), reduction in fatty acid peroxidation end products, reduced numbers of inflammatory cells, and/or upregulated expression of antioxidants. In other embodiments, antioxidants include heme oxygenase-1 (HO-1), catalase, superoxide dismutase-2 (SOD-2), and glutamate-cystein ligase catalytic (GCLC) subunit. In other embodiments, inflammatory cells include CD68+ macrophages and CD3+ T-cells. In other embodiments, increased mitochondrial function includes increased mitochondrial ultrastructure and/or increased mitochondrial biogenesis. In other embodiments, increased mitochondrial function includes increased nuclear PPAR-γ co-activator-1 (PGC-1) expression.

In various embodiments, the exosomes include one or more RNAs such as 2, 3, 4, 5, 6, 7, 8, 9, 10 or more RNAs, including non-coding RNAs. In other embodiments, the non-coding RNAs include tRNAs, yRNAs, rTNAs, mirRNAs, lncRNAs, piRNAs, snRNAs, snoRNAs, further including fragments thereof, among others. In other embodiments, the exosomes include one or more microRNAs selected from the group consisting of: microRNAs miR-146a, miR-148a, miR-22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and miR-23a.

In various embodiments, CDC-derived exosome treatment decreases fibrosis, including left ventricle fibrosis. In other embodiments, decreased fibrosis includes reduction in collagen 1A1 and 3 expression levels, such as protein and mRNA. In other embodiments, decreased fibrosis includes increased microvascular density. In various embodiments, CDC-derived exosome treatment reduces inflammation. In various embodiments, this includes reduction in inflammatory infiltrates, such as CD68+ and CD45+ cells in the left ventricle. In other embodiments, this includes reduction in inflammatory cytokines in serum, including for example MCP-1, IL-6 and TNF-α. In other embodiments, CDC-derived exosome treatment results in an increase in myocardial blood flow.

In various embodiments, CDC-derived exosomes lower risk of arrhythmias as can be exhibited, by for example, a lower arrhythmogenicity index and/or a decrease in action potential duration dispersion in the heart. In various embodiments, CDC-derived exosome treatment normalizes left ventricle relaxation and diastolic pressure, improve survival, and/or confer functional benefits despite persistent hypertension and hypertrophy. For example, in certain embodiments in which pulmonary, arterial, capillary, or cardiac tissue is damaged or dysfunctional, functional improvement may include increased cardiac output, contractility, ventricular function and/or reduction in arrhythmia (among other functional improvements). For example, this may include a decrease in right ventricle systolic pressure. For other tissues, improved function may be realized as well, such as enhanced cognition in response to treatment of neural damage, improved blood-oxygen transfer in response to treatment of lung damage, improved immune function in response to treatment of damaged immunological-related tissues.

EXAMPLES

The present invention is further described with reference to the following non-limiting examples.

Example 1

CDC Culture

CDCs were prepared as described in U.S. Patent Application Publication No. 2012/0315252, the disclosures of which are herein incorporated by reference in their entirety.

In brief, heart biopsies were minced into small fragments and briefly digested with collagenase. Explants were then cultured on 20 mg/mL fibronectin-coated dishes. Stromal-like flat cells and phase-bright round cells grew out spontaneously from tissue fragments and reached confluency by 2-3 weeks. These cells were harvested using 0.25% trypsin and were cultured in suspension on 20 mg/mL poly-d-lysine to form self-aggregating cardiospheres. CDCs were obtained by plating and expanding the cardiospheres on a fibronectin-coated flask as an adherent monolayer culture. All cultures were maintained at 5% $O_2$, 5% $CO_2$ at 37° C., using IMDM basic medium supplemented with 10% FBS, 1% penicillin/streptomycin, and 0.1 mL 2-mercaptoethanol. CDCs were grown to 100% confluency on a fibronectin-coated flask to passage 5.

Example 2

Isolation of Exosomes from CDCs

When the CDCs reached the desired confluency, the flask was washed three times with PBS. CDCs were treated with serum-free medium (IMDM) and were incubated at 37° C. at 5% $O_2$, 5% $CO_2$ for 15 days. After 15 days, the conditioned medium was collected in 225 mL BD Falcon polypropylene conical tubes (BD 352075—Blue Top) and centrifuged at 2,000 rpm for 20 minutes at 4° C. to remove cells and debris (care was taken not to disturb the pellet). The conditioned medium was run through a 0.45 µm membrane filter. The conditioned medium was concentrated using centrifugal filter. A 3 KDa Centricon Plus-70 Centrifugal Filter was pre-rinsed with 10-25 mL of molecular grade water and was centrifuged at 3220 g for five minutes at 18° C. Once the filter was rinsed, all remaining water was carefully removed without touching the filter. 15 mL of the conditioned medium was added to the filter and was centrifuged at 3220 g for 45 minutes at 18° C. After the initial spin, the remaining medium was mixed by pipetting and then spun again until the desired concentration was reached. The final sample was then run through a 0.22 µm syringe filter. 25 µL of the concentrated conditioned medium was diluted in 975 µL of PBS for particle count using the Nanosight. Another 100 µL of the concentrated conditioned medium was used to measure protein concentration. Protein was quantified using the DC protein Assay. In some cases, historical data was used to calculate the concentration of protein in the ultra-filtration by centrifugation (UFC) sample. The concentrated conditioned medium was used immediately or was stored at −80° C.

Example 3

Exosome Precipitation with 25% Polyethylene Glycol (PEG)

The appropriate volume of 25% PEG was added to the filtered concentrated conditioned medium. The samples were incubated at 4° C. for 12-16 hours on an orbital shaker. Once incubation was complete, the samples were centrifuged at 1500 g for 30 minutes at 4° C. The supernatant was carefully removed without disrupting the pellet. The pellet was resuspended in the desired volume of serum-free medium and sampled for particle count.

Example 4

Rat Model of HFpEF

All experimental protocols were approved by the Institutional Animal Care and Use Committee and conformed to Position of the American Heart Association on Research Animal Use. DS rats (Charles River, Wilmington, MA) were used for all in vivo experiments. Rats were fed with a 0.3% NaCl (low salt) diet until 7 weeks of age. At 7 weeks of age, diet was switched to an 8% NaCl diet (high salt diet) in 54 rats by random assignment. When fed with a high-salt diet, DS rats develop concentric LV hypertrophy with compensated diastolic dysfunction at 12 weeks of age, followed by an increase in LV end diastolic pressure, pulmonary edema and death after 19 weeks. DS rats fed normal diet comprised a control group (n=14).

Example 5

Treatment

FIG. 1A depicts the experimental protocol. At 13-14 weeks of age, rats on a high-salt diet (for 6-7 weeks) were randomized to receive allogeneic rat CDCs ($5 \times 10^5$ suspended in 100 µL PBS) or placebo via a left thoracotomy under general anesthesia (Isofluorane 4-5% for induction followed by 2%). Cells (or PBS control, 100 µL) were injected into the LV cavity during aortic cross-clamp, over a period of 20 seconds to achieve intra-coronary delivery. CDCs were grown from a freshly-explanted Wistar-Kyoto rat heart as described (FIG. 1B). Briefly, hearts were minced, subjected to enzymatic digestion and then plated on adherent (fibronectin-coated) culture dishes. These explants spontaneously yield monolayer adherent cells (explant-derived cells) which were harvested and plated in suspension culture ($10^5$ cells/mL on poly-D-lysine-coated dishes) to enable the self-assembly of three-dimensional cardiospheres. Subsequent replating of these cardiospheres on adherent culture dishes yielded CDCs. CDCs at passage 2 were used for all experiments.

Example 6

Cardiac Echocardiography

Echocardiography was performed at baseline, before treatment, and 1 and 4 weeks after treatment to assess systolic and diastolic functions (Vevo 770, Visual Sonics, Toronto, Ontario, Canada), under general anesthesia (Isoflurane 4-5% for induction followed by 2%). Two-dimensional long axis and short axis (at the papillary muscle level) LV images were obtained. M-mode tracings were recorded through the anterior and posterior LV walls at the papillary muscle level to measure LV dimension, and LV anterior and posterior wall thickness at end diastole. Pulse-wave Doppler spectra (E and A waves) of mitral inflow were recorded from the apical 4-chamber view, with the sample volume placed near the tips of the mitral leaflets and adjusted to the position at which velocity was maximal and the flow pattern laminar. E/A ratio was used to assess diastolic function as described. Systolic function was assessed by LV ejection fraction (LVEF) calculated from the long axis view and fractional area change (FAC) calculated from the short axis view.

Example 7

Blood Pressure and Hemodynamic Measurements

Hemodynamic measurements were performed at endpoint just before euthanasia. Under general anesthesia (Isoflurane 4-5% for induction followed by 2%) the right carotid artery was cannulated using a 2 french conductance catheter (SPR-838, Millar, Houston, Texas, USA). Blood pressure was recorded and then the catheter was advanced across the aortic valve into the LV to record end systolic and end diastolic pressures and volumes. Data for determination of LV end-diastolic and end-systolic pressure-volume relationships (EDPVR and ESPVR, respectively) were obtained by temporary inferior vena cava occlusion. The time constant of isovolumic LV pressure fall (Tau) was calculated as described. All data were collected and analyzed using pressure-volume analysis software (LabChart, ADInstruments, Colorado Springs, Colorado, USA).

Example 8

Tissue Collection

At endpoint, after hemodynamic measurements, blood was withdrawn by direct apical heart puncture and serum was collected and frozen. Then, hearts were arrested in diastole (intraventricular injection of KCl) and excised. For histology, heart slices were embedded in OCT compound (Sakura Finetek, Torrance, California, USA) and frozen at −80° C. For protein and RNA quantification, tissue samples were maintained in RNA and protein stabilization reagent (Allprotect, Qiagen, Venlo, Netherlands) and frozen at −80° C.

Example 9

Collagen Content Quantification

To measure fibrosis, 8 μm heart sections were stained with 0.1% picrosirius red (Sigma Aldrich, St. Louis, Missouri) for collagen. Images were obtained at ×80 magnification and analyzed using Image J software. The collagen content was calculated as a percentage of the area of each image.

Example 10

Immunostaining

For vessel density, myocardial samples underwent immunostaining for von Willebrand factor (Abcam 6994) and α-smooth muscle actin (Abcam 32575). Arterioles were identified by von Willebrand factor and α-smooth muscle actin positive staining and capillaries by von Willebrand factor positive staining only. For cardiomyocyte cross sectional area, slides were immunostained with wheat-germ agglutinin (Alexa Fluor 488 conjugated, Invitrogen) and αsarcomeric actin (α-SA) (Abcam 72592). Cross-sectional area was measured only in regions where cardiomyocytes met the following 3 criteria: cellular cross-section present; visible nuclei located in the center of the cell; and intact cell borders. Cell proliferation was assessed by staining with Ki67 (Abcam 66155); slides were stained with α-SA (Abcam 72592) and the percent of Ki67-positive cardiomyocytes (α-SA positive) over the total number of cardiomyocytes was calculated. The percent of non-cardiomyocyte Ki-67 positive cells (α-SA negative) was also measured. White blood cells and macrophages in the heart were quantified using CD45 Staining (BD Pharmingen) and CD68 staining (AbD Serotec) respectively. The appropriate fluorescently-conjugated secondary antibodies (Invitrogen) were applied and all slides were counterstained for DAPI (Molecular Probes). Five to 10 images per slide were imaged using a confocal laser microscope and analyzed using Image-J software.

Example 11

Cytokine Array and Western Blot

Inflammatory cytokines were quantified in the serum using a commercially available cytokine array (Raybiotech, Norcross, Georgia, USA). Sera from 4 control rats, 4 CDC-treated and 4 placebo-treated animals were used. All values were normalized to the positive control.

For protein isolation, tissues were minced, suspended in T-PER (with HALT protease and phosphatase inhibitors, Thermo Scientific), homogenized with a bead ruptor and then centrifuged at 10,000 g for 15 minutes at 4° C. The supernatant was collected and protein concentration measured (BCA protein assay, Thermo Scientific). Protein samples were prepared under non-denaturing conditions for gel electrophoresis (NuPAGE 4%-12% Bis-Tris, Invitrogen). Thirty μg of protein was loaded into each well for separation. Proteins were then transferred to a polyvinylidene fluoride membrane (Bio-Rad) for immunoblotting with collagen 1A1 (Santa Cruz sc-25974) and collagen 3 (Santa Cruz sc-8780) antibodies. Bands were visualized following activation with ECL (Thermo Scientific) and exposure on film (Kodak Carestream Biomax, Sigma-Aldrich).

Example 12

RNA Isolation and Semi-Quantitative Reverse Transcriptase Polymerase Chain Reaction Expression, RNA Sequencing RNA was isolated from LV samples (n=7 in each group) (RNA easy kit, Qiagen, Venlo, Netherlands). Then, cDNA was synthesized from mRNA using the High-Capacity cDNA Reverse Transcription Kit (Life Technologies, Carlsbad, California, USA) according to the manufacturer's protocol. The resulting cDNA was standardized across samples and then mixed with master mix and designated primer sets (Life Technologies, Carlsbad, California, USA). Predesigned TaqMan primer sets for collagen-1A1 and collagen-3 were used. Relative mRNA expression of target genes was normalized to the endogenous GAPDH gene.

RNA was isolated from LV samples (n=3 in each group) (RNA easy kit, Qiagen, Venlo, Netherlands). rRNA was removed using the Ribo-Zero rRNA Removal Kit from Illumina. Libraries for RNA-Seq were prepared with KAPA Stranded RNA-Seq Kit. The workflow consists of mRNA enrichment, cDNA generation, and end repair to generate blunt ends, A-tailing, adaptor ligation and PCR amplification. Different adaptors were used for multiplexing samples in one lane. Sequencing was performed on Illumina NextSeq 500 for a single read of 75 run. Data quality check was done on Illumina SAV. Demultiplexing was performed with Illumina Bcl2fastq2 v 2.17 program. The reads were first mapped to the latest UCSC transcript set using Bowtie2 version 2.1.0 and the gene expression level was estimated using RSEM v1.2.15. TMM (trimmed mean of M-values) was used to normalize the gene expression. Differentially expressed genes were identified using the edgeR program. Genes showing altered expression with $p<0.05$ and more than 1.5 fold changes were considered differentially expressed. The pathway and network analysis was performed using Ingenuity (IPA). IPA computes a score for each network according to the fit of the set of supplied focus genes. These scores indicate the likelihood of focus genes to belong to a network versus those obtained by chance. A score >2 indicates a ≤99% confidence that a focus gene network was not generated by chance alone. The canonical pathways generated by IPA are the most significant for the uploaded data set. Fischer's exact test with FDR option was used to calculate the significance of the canonical pathway.

Example 13

Effect on Survival

To examine the effect on survival, all animals were carefully monitored every day. Survival was assessed until 1 month. Seven additional rats in each group were followed for 2 more weeks (total of 6 weeks after treatment). Animals unable to move, drink and eat (as assessed by an animal technician not involved in the study and not aware of the treatment) were euthanized and recorded as dead in order to comply with institutional animal welfare policy.

Example 14

Statistical Analysis

Continuous variables are presented as mean±standard deviation in the text and mean±standard error in the figures. Categorical variables are expressed as absolute number and percentage. Normal distribution of variables was assessed using Kolmogorov-Smirnov test. If normality was established, independent groups (n=2) were compared using unpaired t-test, and multiple groups were compared using 1-way analysis of variance. For non-normal distribution, Mann-Whitney test was used for comparison of 2 groups and Kruskal-Wallis test was used to compare multiple groups. Survival analysis was performed using Kaplan Meier analysis. P value <0.05 was considered statistically significant.

Example 15

Blood Pressure and Cardiac Hypertrophy

Table 2 shows characteristics of the high-salt and control animals at baseline and after 6 weeks of diet (13 weeks of age). As expected, rats fed a high-salt diet developed hypertension and cardiac hypertrophy after 6 weeks, but low-salt controls did not. Those changes were associated with diastolic dysfunction as shown by a decreased E/A ratio by echocardiography (1.7±0.2 vs. 1.2±0.2, P<0.0001), without any changes in LV volumes, LVEF or FAC (Table 2).

TABLE 2

Characteristics of high-salt and low-salt fed rats before (baseline) and after 6 weeks of diet.

| | Baseline | | 6 weeks | |
|---|---|---|---|---|
| | Low salt | High salt | Low salt | High salt |
| SBP (mmHg) | NA | NA | 133 ± 23 | 188 ± 17 * |
| DPB (mmHg) | NA | NA | 92 ± 15 | 130 ± 12 * |
| LVEF (%) | 73.1 ± 4.8 | 73.0 ± 5.1 | 71.6 ± 3.8 | 74.4 ± 5.9 |
| FAC (short axis) (%) | 64.1 ± 3.0 | 64.2 ± 4.9 | 62.3 ± 4.6 | 63.2 ± 5.9 |
| AW thickness (mm) | 1.2 ± 0.1 | 1.2 ± 0.1 | 1.2 ± 0.1 | 1.8 ± 0.2 * |
| PW thickness (mm) | 1.3 ± 0.1 | 1.3 ± 0.1 | 1.3 ± 0.1 | 2.0 ± 0.3 * |
| LVEDV (mL) | 330 ± 46 | 329 ± 70 | 484 ± 112 | 510 ± 110 |
| LVESV (mL) | 89 ± 22 | 89 ± 28 | 142 ± 47 | 130 ± 50 |
| Early-to-late ventricular filling E/A ratio | 1.7 ± 0.2 | 1.7 ± 0.3 | 1.7 ± 0.2 | 1.2 ± 0.2 * |
| Heart weight (g) | NA | NA | 1.42 ± 0.14 | 1.67 ± 0.10 * |
| Heart weight/BW (mg/g) | NA | NA | 4.1 ± 0.4 | 5.2 ± 0.5 * |

* P < 0.05 between high-salt and low-salt group at 6 weeks.

Example 16

Echocardiographic Studies: CDCs Normalize E/A Ratio

Figure 1C:
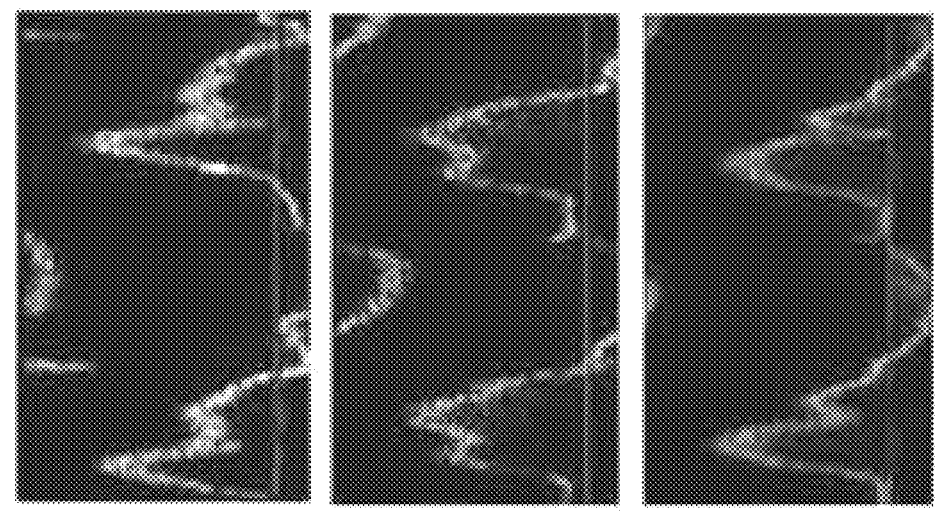
(FIG. 1C) Representative images of trans-mitral flow by Doppler echocardiography at endpoint in control, placebo- and CDC-treated rats.
Figure 1F:
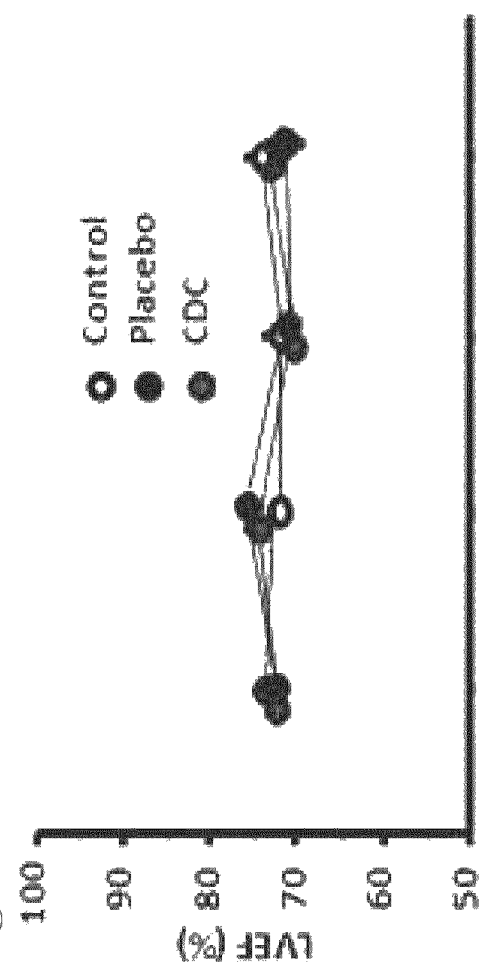
FIG. 1.
(FIG. 1A) Study design.
(FIG. 1B) Cardiosphere-derived cell manufacturing protocol.
Figure 1H:
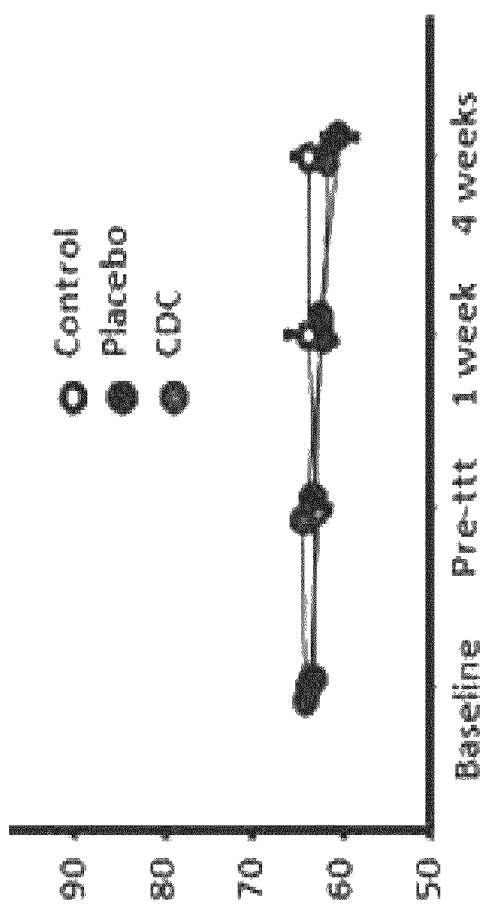
Figure 1E:
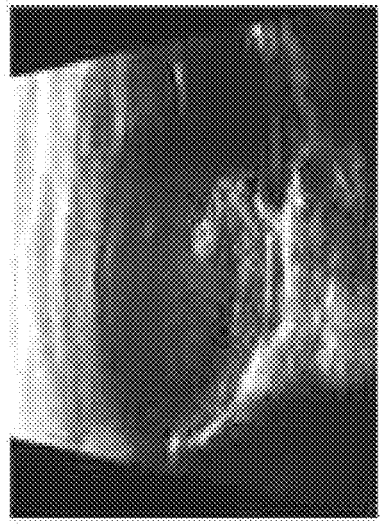
Figure 1G:
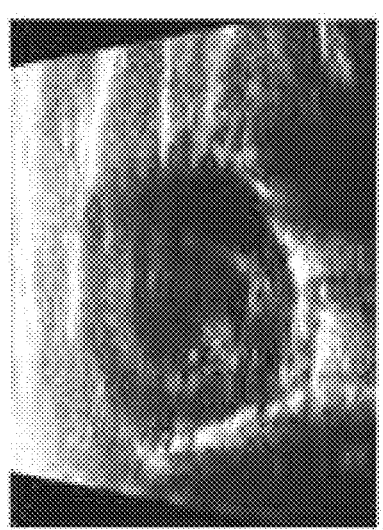

Having confirmed the presence of cardiac hypertrophy and diastolic dysfunction, the Inventors randomly allocated rats to intracoronary CDC or vehicle infusion. FIG. 1C shows representative images of trans-mitral flow at endpoint in control, placebo- and CDC-treated animals. Pooled data (FIG. 1D) reveal that, after 6 weeks of diet but before treatment, Early-to-late ventricular filling (E/A) ratio was similar in placebo and CDC groups, but lower than in control. After intracoronary infusion of CDCs (but not placebo), E/A ratio increased over time (FIG. 1D), a change which was evident as soon as 1 week after treatment. At endpoint, E/A ratio had returned to control levels in CDC-treated animals (1.7±0.2 for CDC vs. 1.8±0.16 for control, P=0.36) whereas it remained depressed in placebo-treated animals (1.2±0.3, P<0.0001 vs. CDC and vs. control), indicating a likely normalization of LV relaxation with CDC treatment (an interpretation verified below by hemodynamic recordings). In contrast, LVEF (measured in long-axis views, FIG. 1 E-F), FAC (from short axis views, FIG. 1 G-H) and LV volumes (FIG. 1I-J) were equivalent in all groups.

Example 17

Figure 2A:
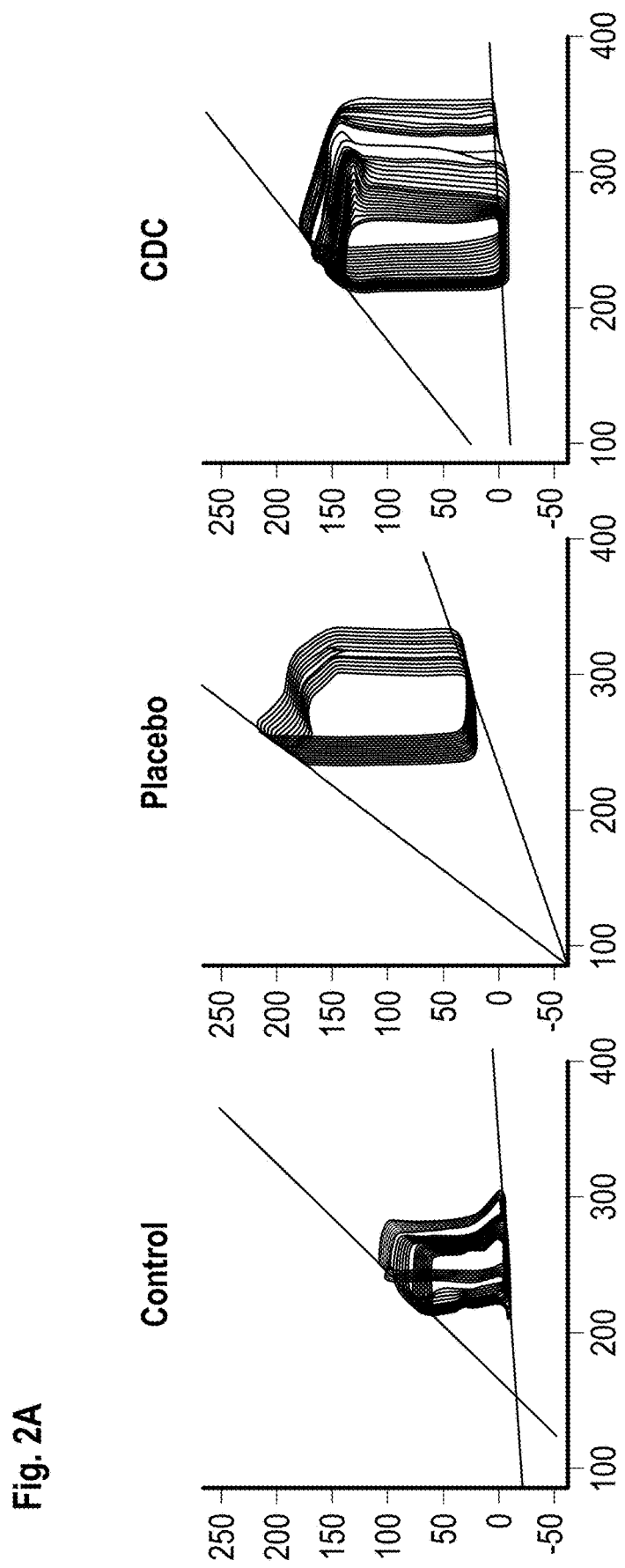
(FIG. 2A) Representative PV loop recordings in control, placebo- and CDC-treated rats. CDCs normalize Tau (FIG. 2B) and −dP/dt min (FIG. 2C) in rats with HFpEF without change in dP/dt max (FIG. 2D). PV loop analysis reveals normalization of the slope of the end-diastolic pressure volume relationship (EDPVR) (FIG. 2E) with no change in end-systolic pressure volume relationship (ES-PVR) (FIG. 2F). LV end diastolic pressure (LVEDP) is normal in the CDC but not in placebo-treated animals (FIG. 2G). The differences between CDC- and placebo-treated rats are not related to changes in systolic (FIG. 2H) or diastolic (FIG. 2I) blood pressure or heart rate (FIG. 2J) (n=8 for control and n=12 for placebo and CDC; for PV loop families, n=6 for control, n=7 for placebo and n=8 for CDC). *P<0.05 vs. placebo and CDC. *P<0.05 vs. placebo and CDC. †P<0.05 vs. control and CDC, ‡P<0.05, all by ANOVA.
Figure 2D:
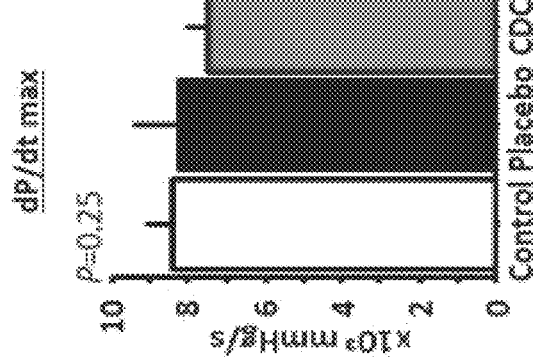
FIG. 2.
Figure 2C:
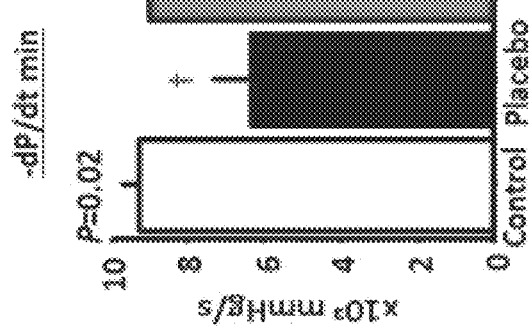
Figure 2B:
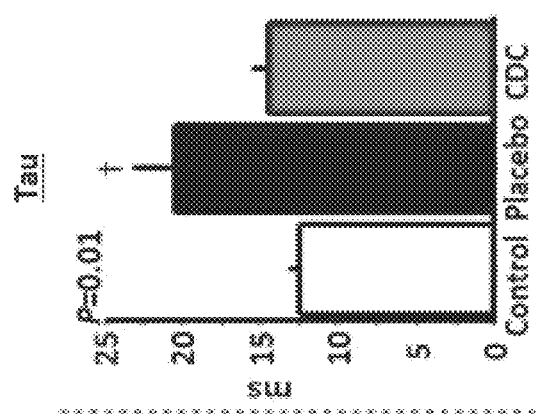

Hemodynamic Studies: CDC Treatment Normalizes LV Relaxation and Prevents Elevation of LVEDP FIG. 2A shows representative recordings of PV loop families at endpoint. The time constant of isovolumic LV pressure fall (Tau) was prolonged in placebo-treated animals compared to CDC-treated animals (21±8 s vs. 13±1 s in control, P=0.02 and 14±4 s in CDC, P=0.006; FIG. 2B) and control, while -dP/dt min was lower, indicating impaired relaxation (FIG. 2C) without changes in dP/dt max (FIG. 2D). In parallel, PV loop analyses confirmed that LV distensibility was decreased in the placebo-treated animals as demonstrated by the steeper slope of EDPVR in placebo-treated animals as compared to CDC-treated and control animals (FIG. 2E), again without changes in ESPVR (FIG. 2F).

LVEDP was twofold higher in the placebo- than in CDC-treated and control animals (17±10 mmHg vs. 9±4 mmHg in control, P=0.01 and 8±3 mmHg in CDC, P=0.002; FIG. 2G). The normalization of LVEDP and Tau in CDC-treated rats confirms that the increase of E/A ratio over time in this group was due to normalization of LV relaxation rather than to progression toward a pseudo-normal pattern of trans-mitral flow (which would have been associated with increased LVEDP and Tau).

The Inventors did not observe any differences in blood pressure or heart rate between CDC- and placebo-treated animals that could have confounded relaxation and LVEDP measurements (although blood pressure was lower in the control group as expected; FIGS. 2H-J). Thus, the improvements in diastolic function were not due to antihypertensive or chronotropic effects of CDCs.

Example 18

CDC Treatment Improves Survival and Decreases Lung Congestion

Consistent with the improvement of diastolic function, the Inventors observed a dramatic improvement of survival in CDC-treated rats (Kaplan-Meier survival curves, FIG. 3A; Logrank P=0.03). Postmortem lung weight and lung weight/body weight ratio were higher in placebo-treated rats, indicative of pulmonary congestion (FIG. 3B). In parallel, FIG. 3C shows that animals treated with CDCs resumed some physiological weight gain, while placebo rats lost weight, presumably due to cardiac cachexia (an impression which was confirmed visually).

Example 19

Figure 4A:
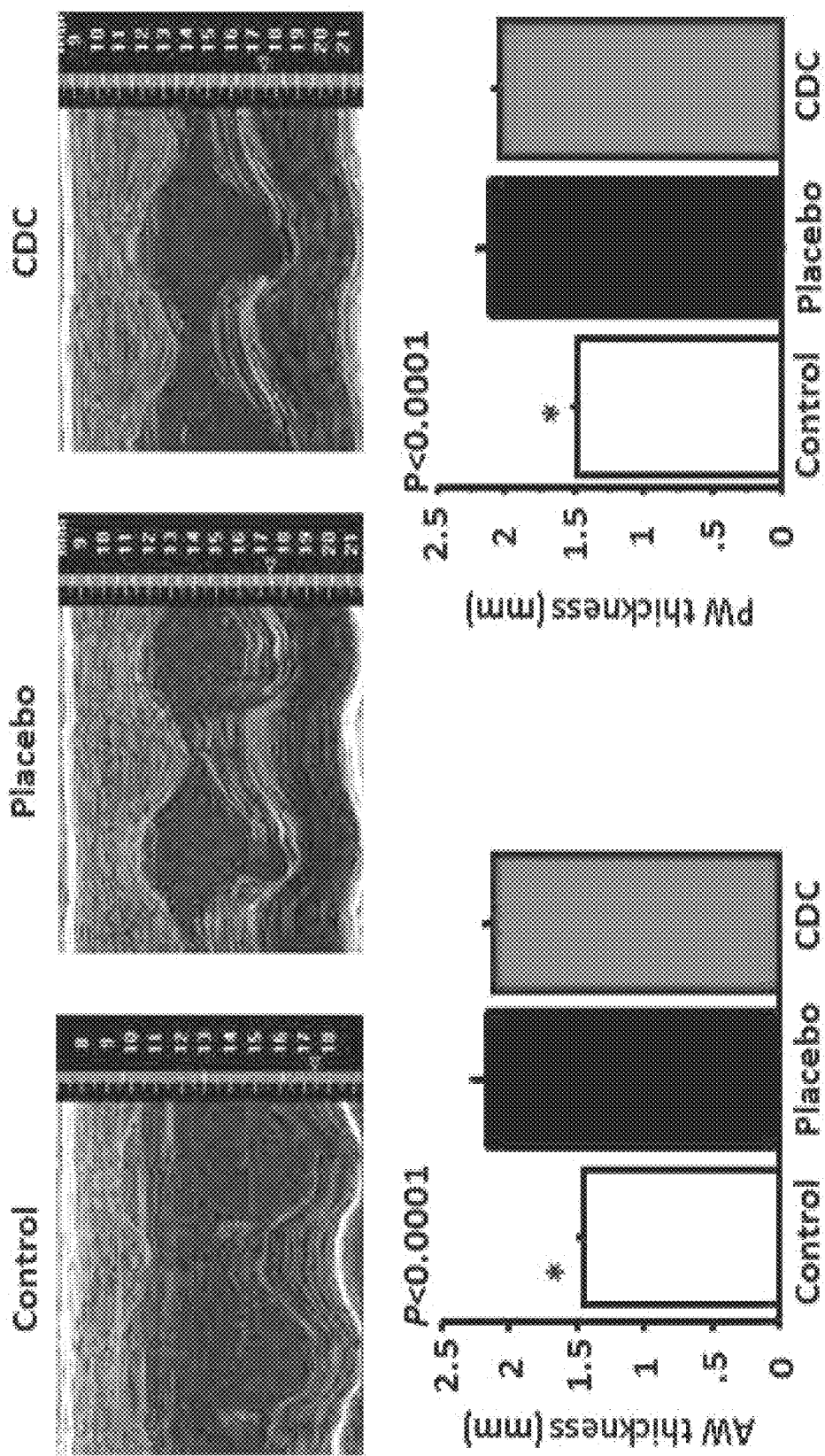
FIG. 4: Benefit of CDC treatment is not related to decreased cardiac hypertrophy. Cardiac anterior wall (AW) and posterior wall (PW) thickness by echocardiography (FIG. 4A), heart weight and heart weight/body weight ratio (FIG. 4B) and cross-sectional cardiomyocyte area (FIG. 4C) are equally elevated in placebo- and CDC-treated rats relative to control. (n=10 for controls and n=15 for placebo and n=18 for CDC in A; n=6 for control, n=11 for placebo and n=14 for CDC in B; n=5 in each group for FIG. 4C). *P<0.05 vs. placebo and CDC by ANOVA.
Figure 4C:
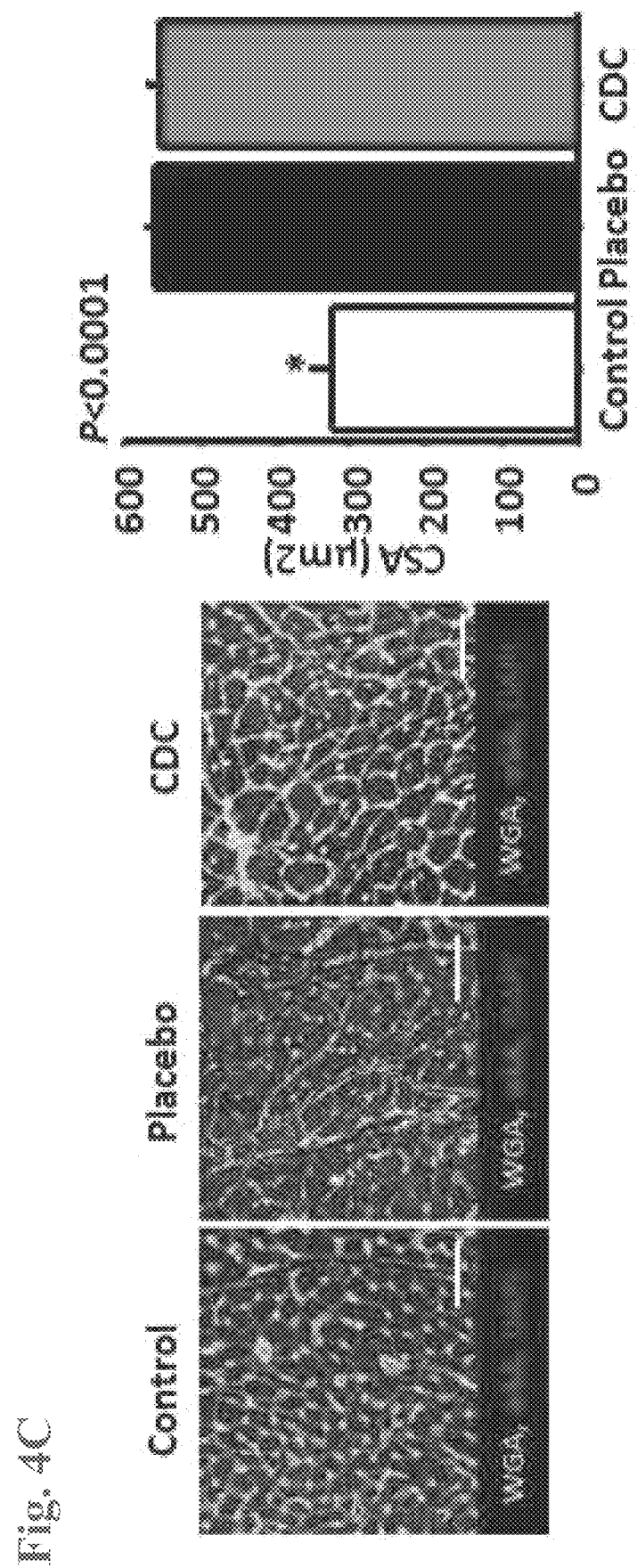

Improvement of LV Relaxation is not Associated with Quantitative Changes in Cardiac Hypertrophy LV hypertrophy (both macroscopic and cellular) can occur with or without diastolic dysfunction. The Inventors quantified cardiac hypertrophy using LV wall thickness by echocardiography, heart weight and cardiomyocyte cross sectional area. Notably, the CDCrelated improvement in diastolic function was not due to a decrease in cardiac hypertrophy: wall thickness by echocardiography (FIG. 4A), as well as post-mortem heart weight and cardiomyocyte cross-sectional area (FIG. 4B), remained equivalent in CDC and placebo groups. Thus, CDCs were salutary without decreasing cardiac hypertrophy.

Figure 5A:
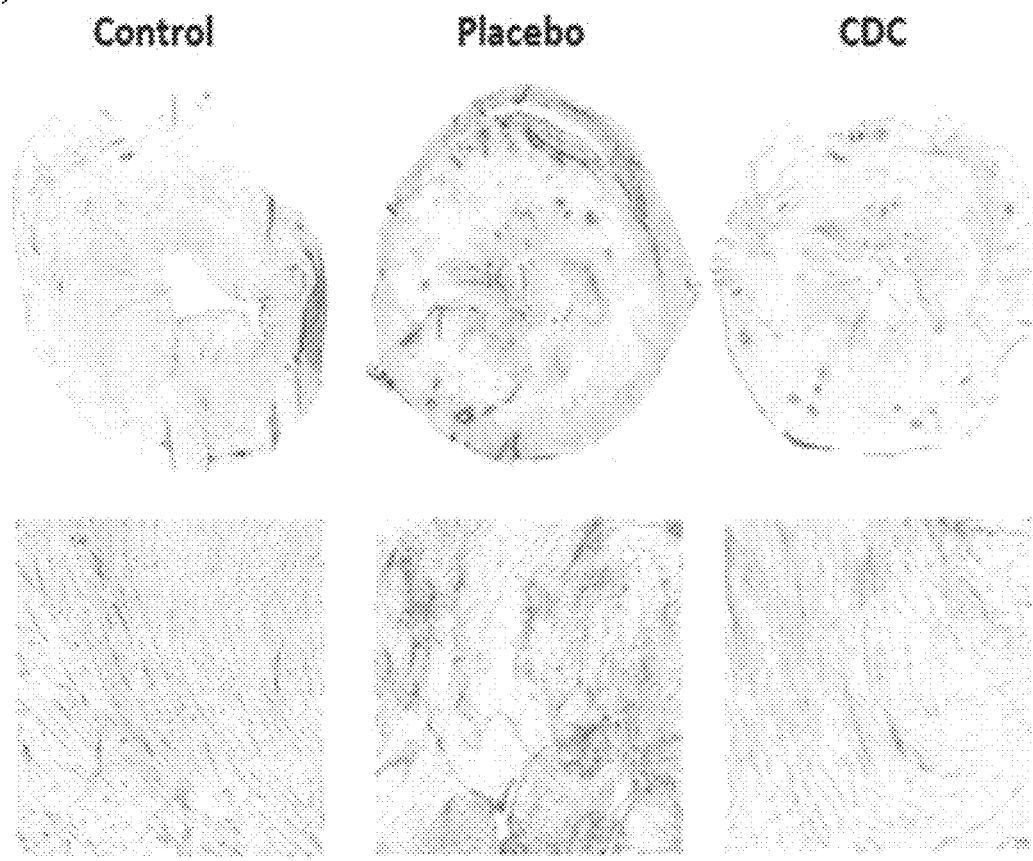
(FIG. 5A) Representative LV sections stained with picrosirius red in control, placebo- and CDC-treated rats.
Figure 5B:
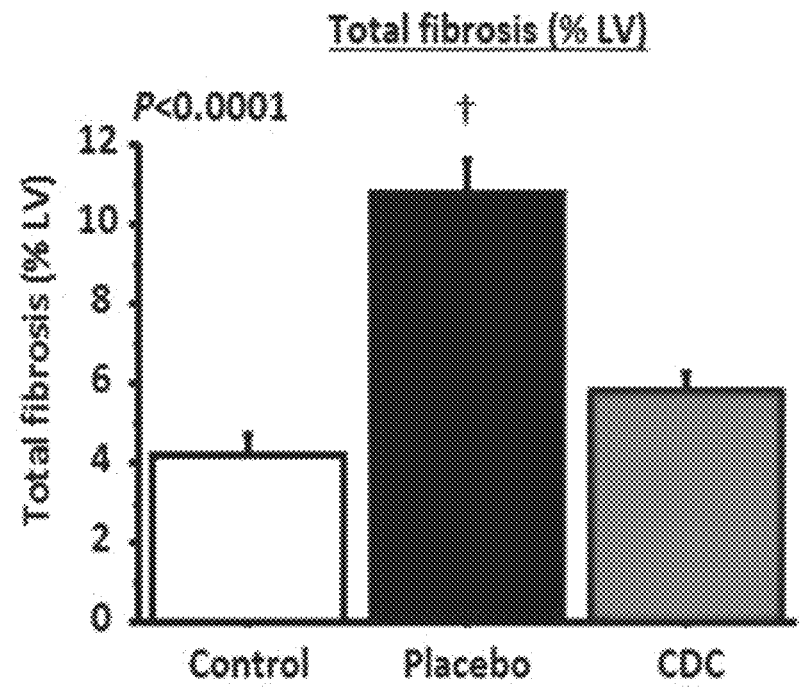
(FIG. 5B) LV fibrosis quantified from such images is higher in placebo- than in CDC-treated and control rats.
Figure 5C:
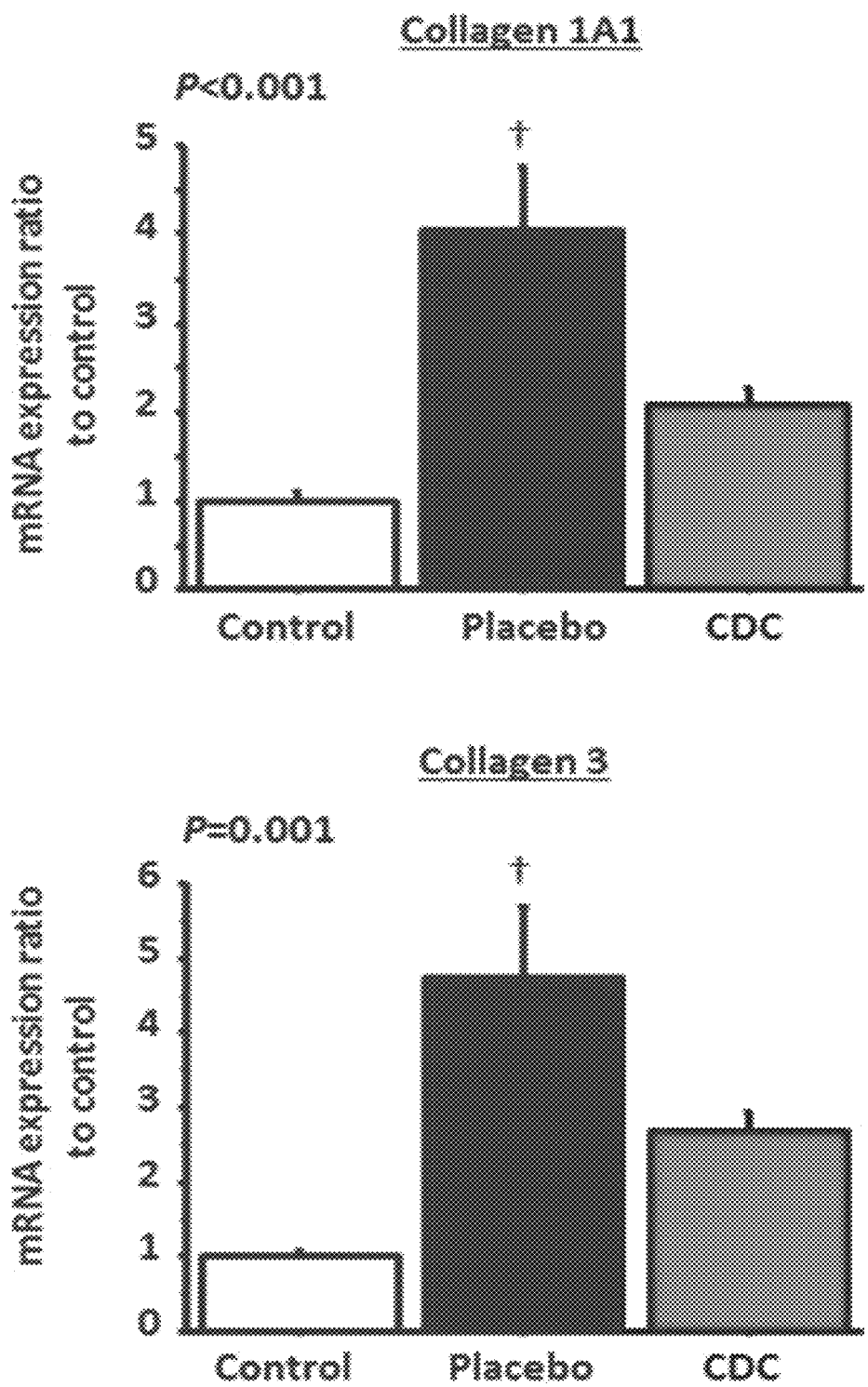
(FIG. 5C) mRNA expression for collagen 1A1 and collagen 3 is higher in placebo- than in CDC-treated and control rats. (n=6-8 in each group). †P<0.05 vs. control and CDC by ANOVA.
Figure 9A:
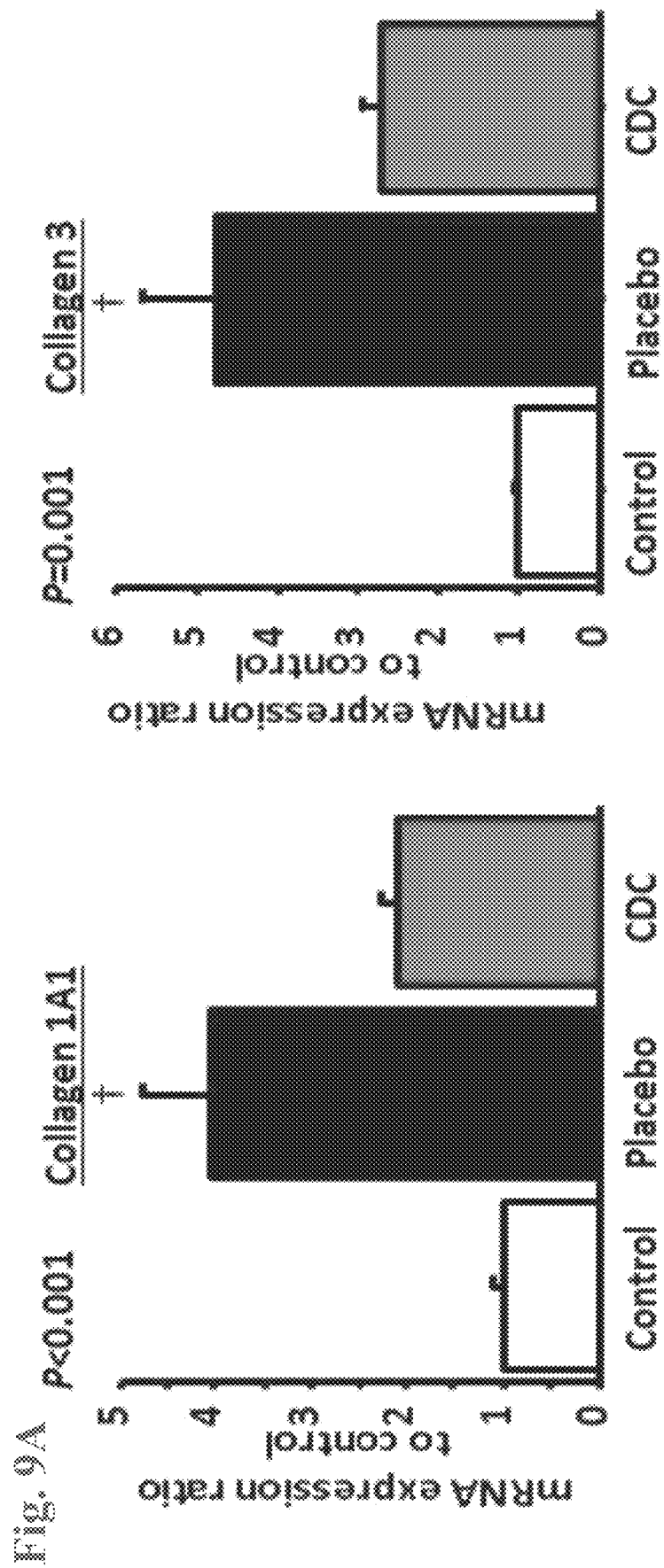
(FIG. 9A) mRNA expression for collagen A1 and collagen 3 is higher in placebo- than in CDC-treated and control rats.
Figure 9B:
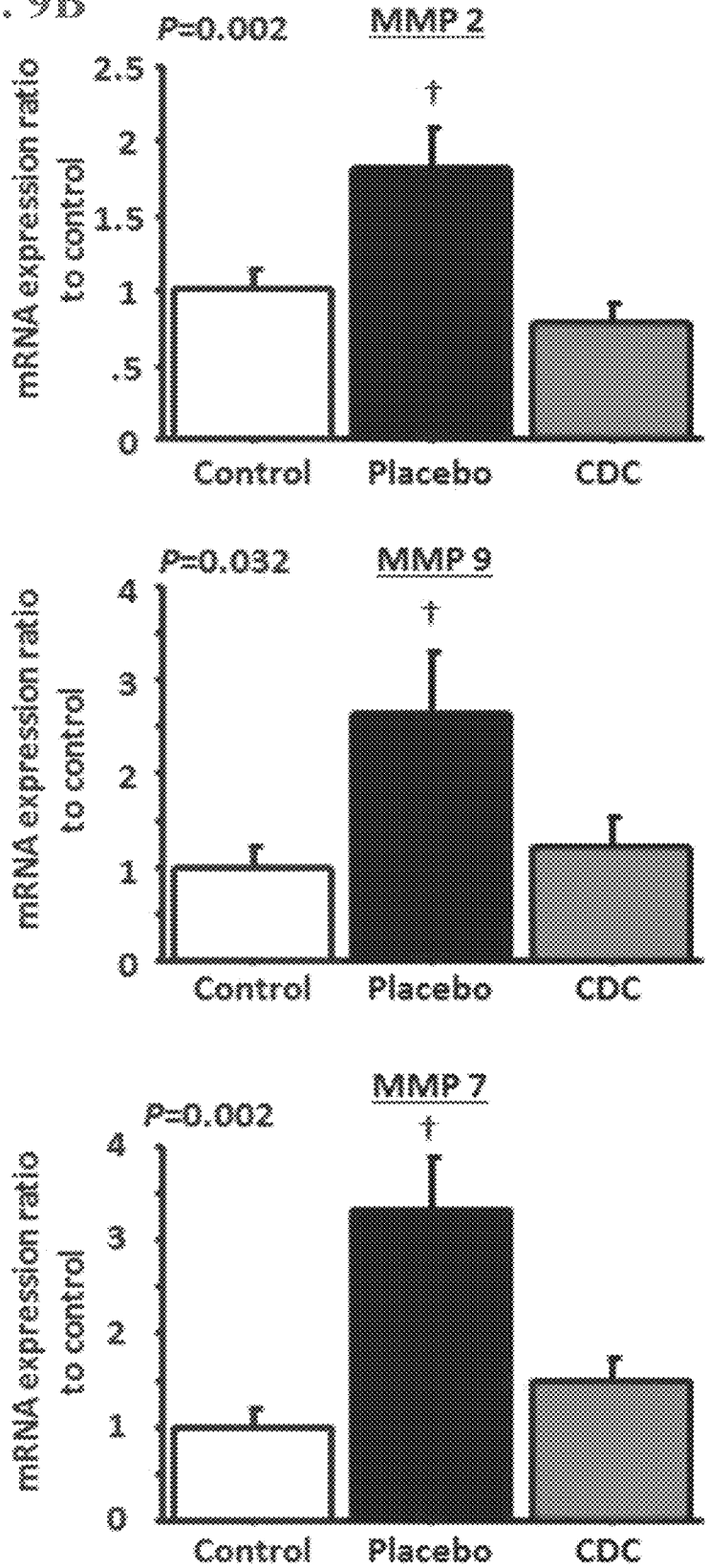
(FIG. 9B) mRNA expression for MMP-2, MMP-9 and MMP-7 is higher in placebo- than in CDC-treated and control rats.
Figure 9C:
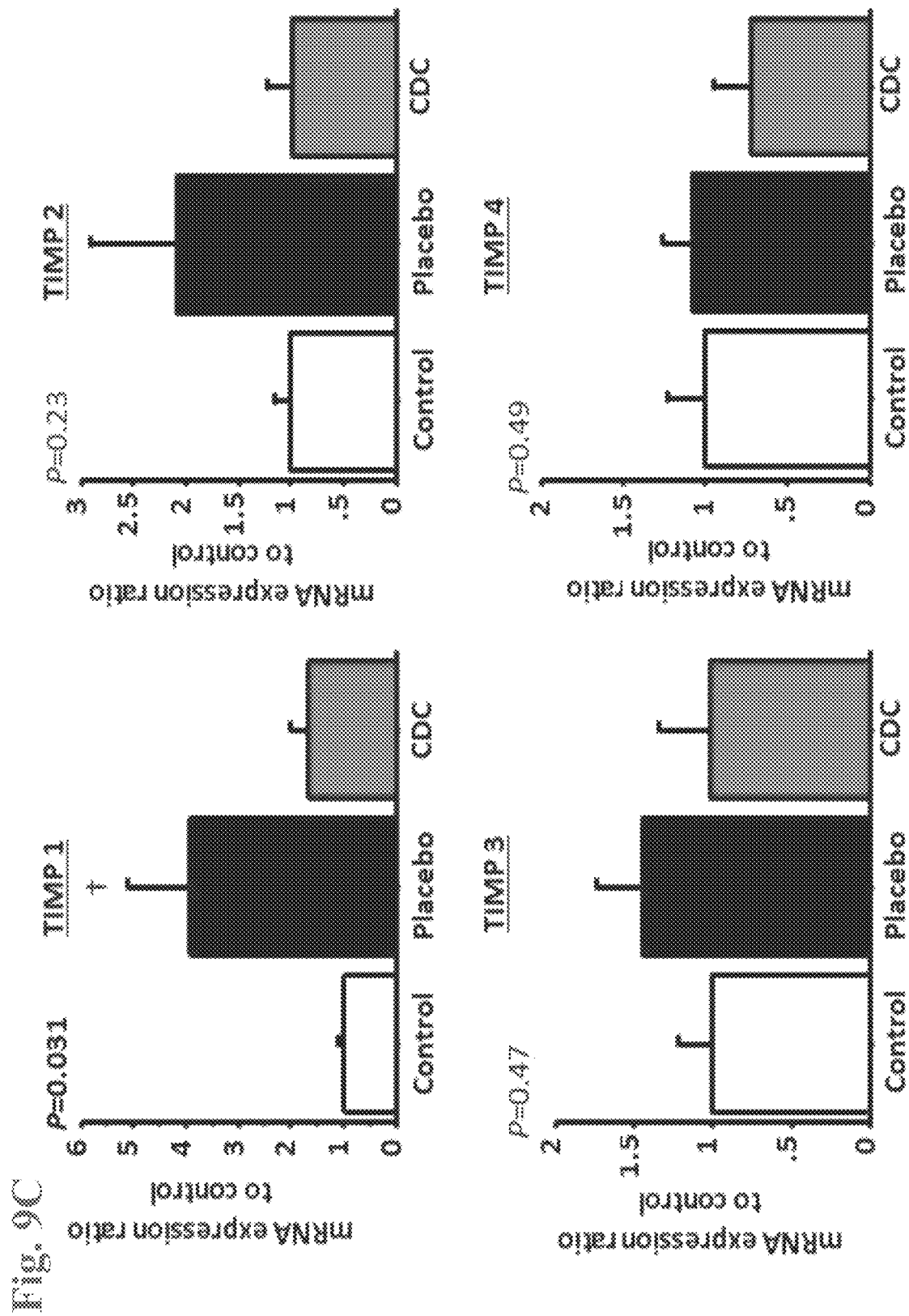
(FIG. 9C) mRNA expression for TIMP 1 (but not TIMP-2, TIMP3 and TIMP4) is higher in placebo- than in CDC-treated and control rats (n=7 in each group).

Anti-fibrotic effect of CDCs. Fibrosis is increased in HFpEF. The Inventors assessed fibrosis using picrosirius red staining for total collagen and semi-quantitative reverse transcriptase polymerase chain reaction to measure transcript levels for collagen 1 and 3. FIG. 5A shows representative images of hearts stained with picrosirius red. Overall LV fibrosis was two-fold higher in placebo- versus CDC-treated rats; fibrosis in the latter approached control values (FIG. 5B-C). Concomitantly, collagen-1 and collagen-3 in the LV (quantified by western blot) were higher in placebo-treated rats than in control or CDC-treated rats (FIG. 5D). Moreover, cardiac myofibroblasts increased dramatically in placebo-treated, but not in CDC-treated, DS rats (FIG. 5E). Also, transcript levels of MMP-2, MMP-7, MMP-9 and TIMP-1 as well as collagen 1A1 and collagen 3 were higher in the placebo treated animals compared to the control and CDC-treated animals (which had similar levels; FIG. 9). These increased transcript levels are suggesting of increased extracellular matrix turnover associated with HFpEF which is normalized by CDC treatment.

Figure 6A:
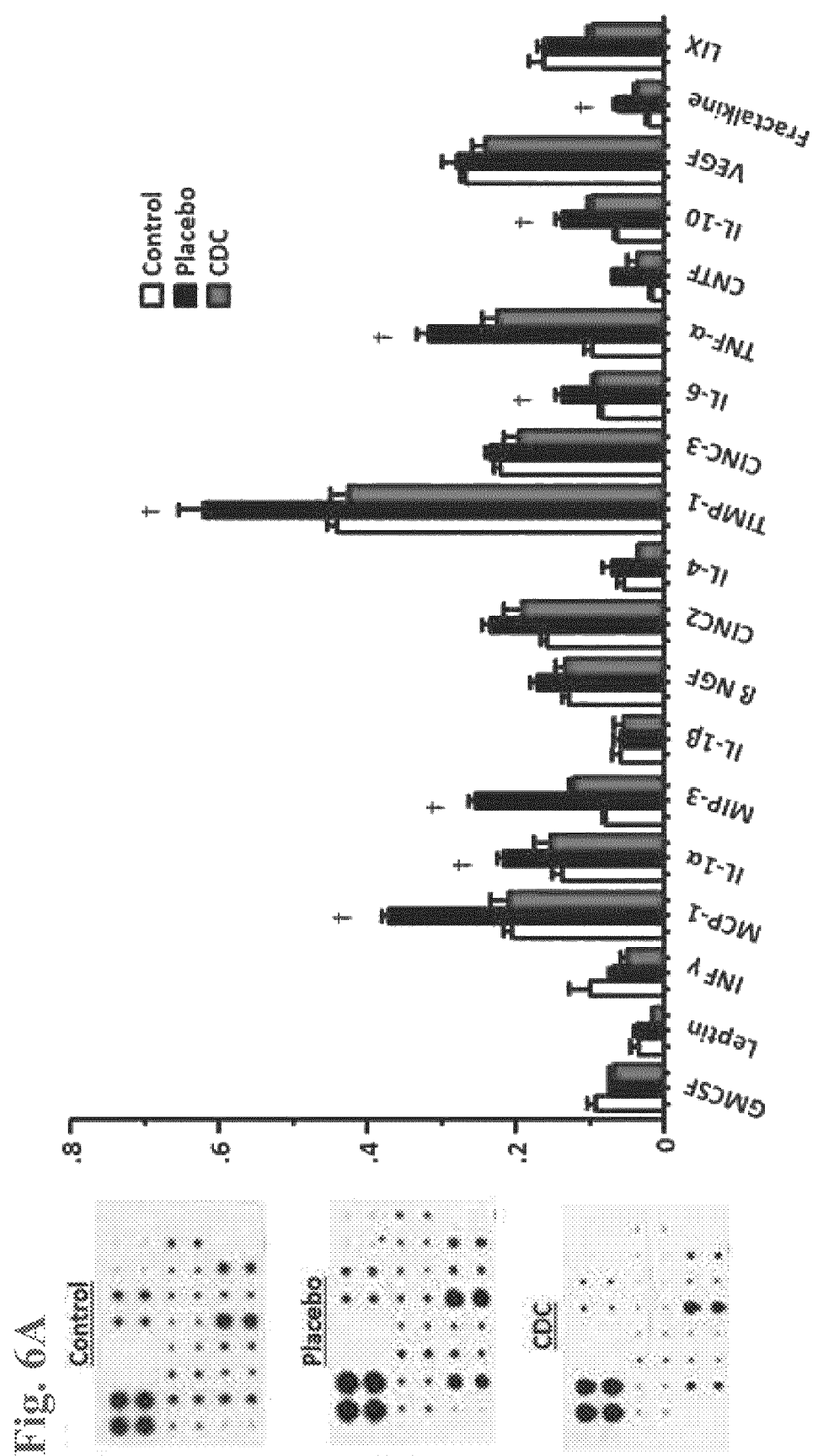
(FIG. 6A) CDC treatment normalizes the expression of pro-inflammatory and pro-fibrotic cytokines in serum including TNF-α, IL-6, MCP-1 and TIMP-1 (n=4 in each group).
Figure 6B:
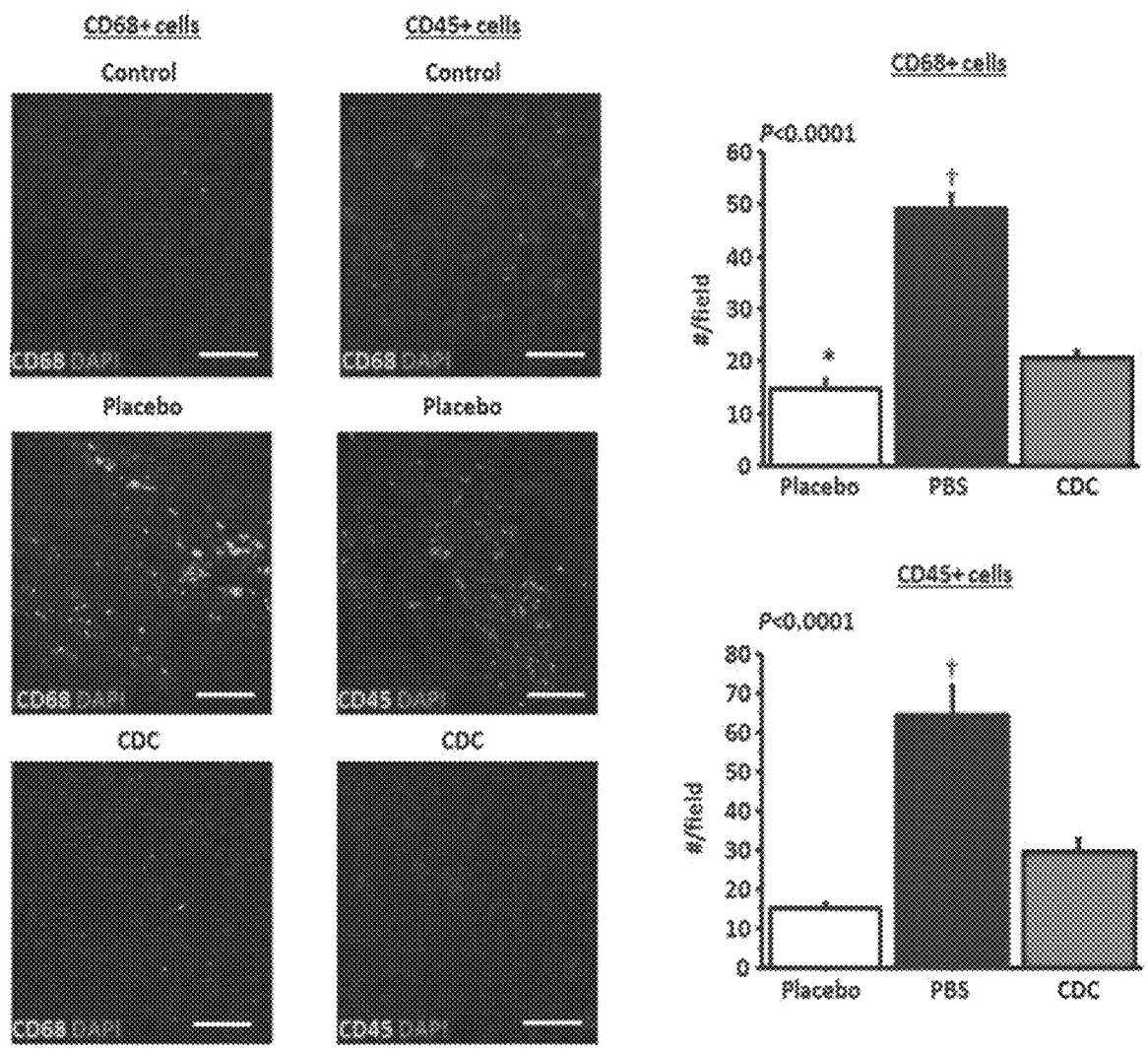
(FIG. 6B) CDC treatment decreases myocardial infiltration by macrophages (CD68) and leukocytes (CD45) in the LV (n=5 in each group). *P<0.05 vs. placebo and CDC; †P<0.05 vs. control and CDC, by non-parametric tests for FIG. 6A and by ANOVA for FIG. 6B.

Attenuation of inflammation. Quantification of cytokines in the serum revealed lower levels of pro-inflammatory and pro-fibrotic cytokines in CDC-treated rats as compared to placebo; the levels in CDC-treated rats were comparable to those in controls (FIG. 6A). Among those cytokines, some have been linked to the development of HFpEF (especially MCP1, IL6, TNFα) and to the accumulation of collagen (TIMP1). CDC treatment was also associated with a twofold reduction of macrophages (CD68-positive cells) and leukocytes (CD45-positive cells) in the heart compared to placebo, approaching control levels (FIG. 6B).

Figure 7A:
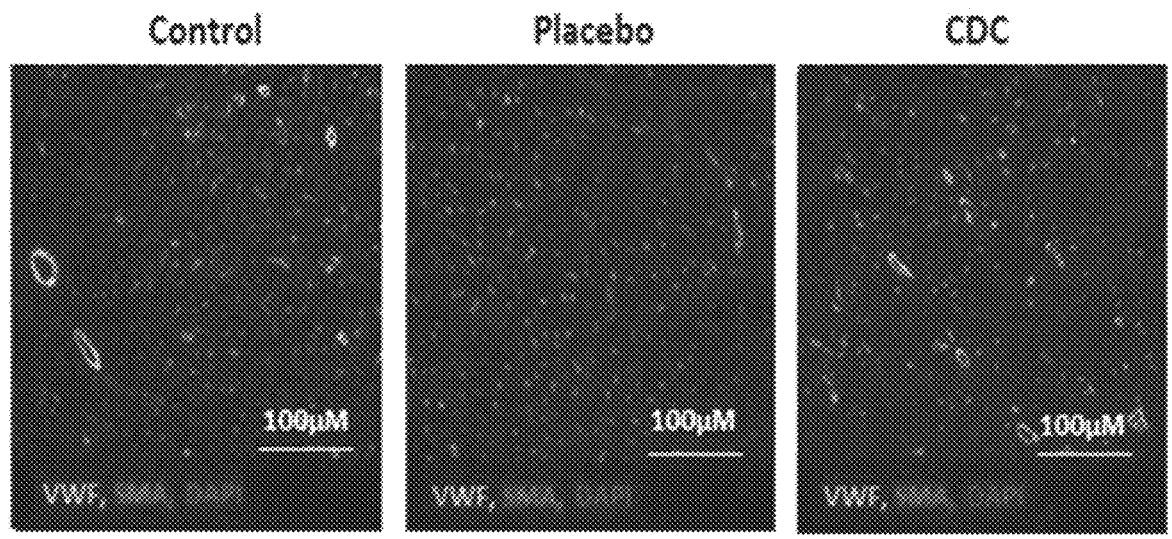
(FIG. 7A) Immunostaining for von Willebrand factor and smooth muscle actin in control, placebo- and CDC-treated rats. CDC treatment increases arteriolar (FIG. 7B) and capillary (FIG. 7C) density in the LV.
Figure 7B:
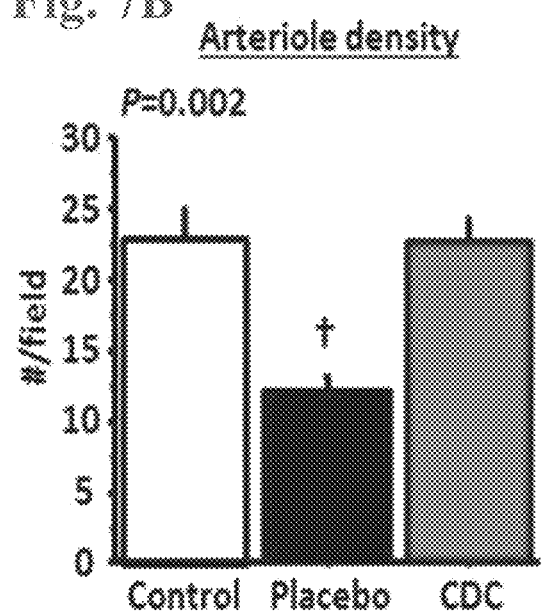
FIG. 7.
(FIG. 7D) Immunostaining for Ki67 and α-actin in control, placebo- and CDC-treated rats. CDC treatment increased cardiomyocyte proliferation (FIG. 7E) and decreased the proliferation of fibroblasts (FIG. 7F) compared to placebo. (n=5 in each group). †P<0.05 vs. control and CDC, both by ANOVA; ‡P<0.05 vs. control and placebo.
Figure 7C:
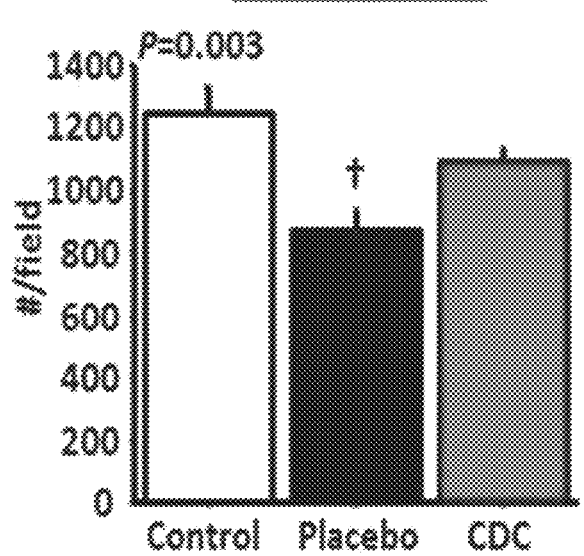
Figure 7D:
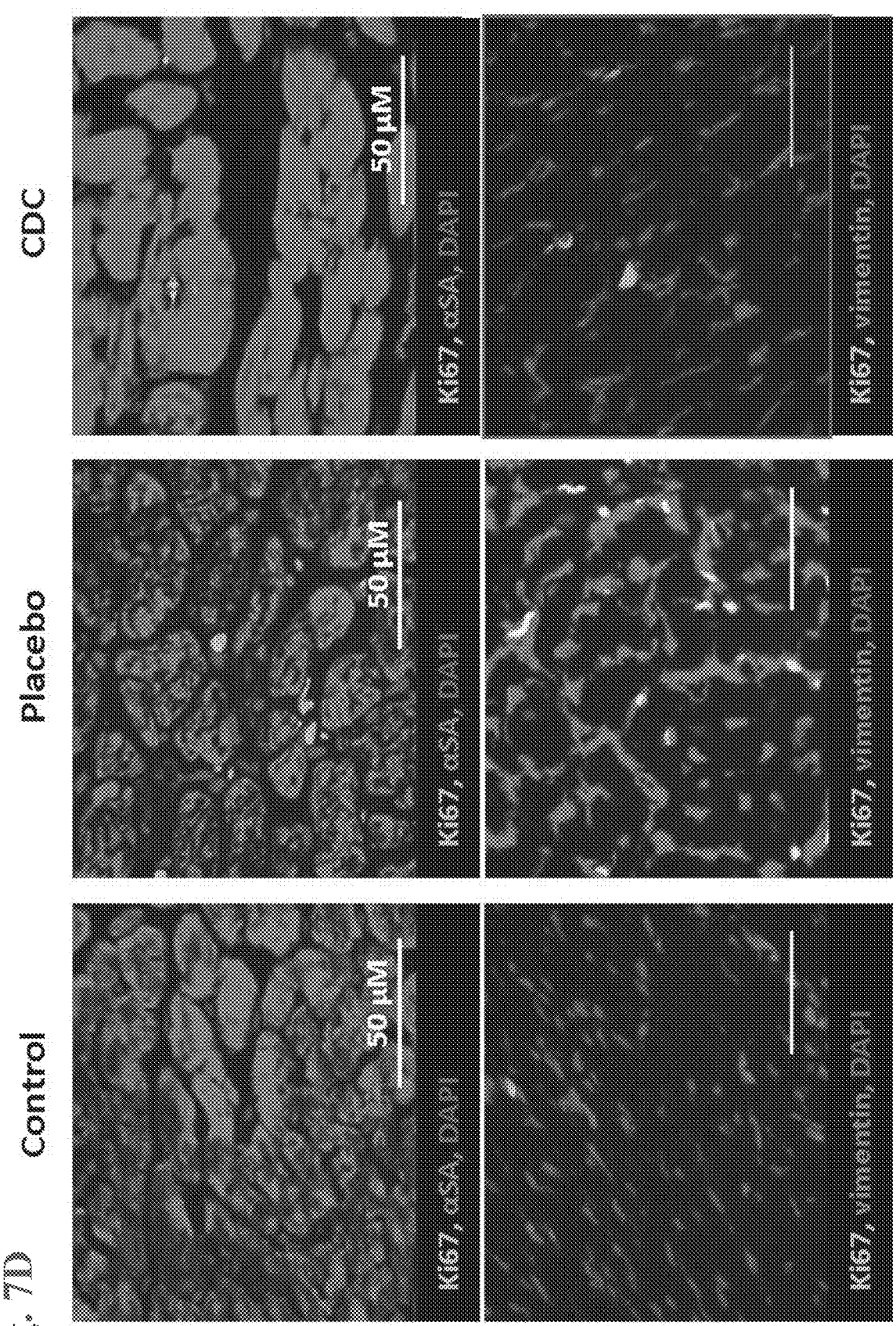

Vessel density and cell proliferation. The Inventors investigated arteriolar and capillary density in the LV (FIG. 7A). Both vascular densities were lower in placebo-treated rats as compared to control (FIG. 7B-C); CDC treatment normalized arteriolar density and significantly increased capillary density compared to placebo, although capillary density did not reach the value measured in controls. Parallel measurements of cell proliferation using Ki67 immunostaining (FIG. 7D) revealed that CDCs stimulated cardiomyocyte proliferation (cells positive for both αSA and Ki67; FIG. 7E). In contrast, placebo-treated rats had more non-cardiomyocyte proliferating cells (Ki67 positive, αSA negative; FIG. 7E) than control. The level of non-cardiomyocyte proliferating cells was partially normalized by CDC treatment.

Figure 8A:
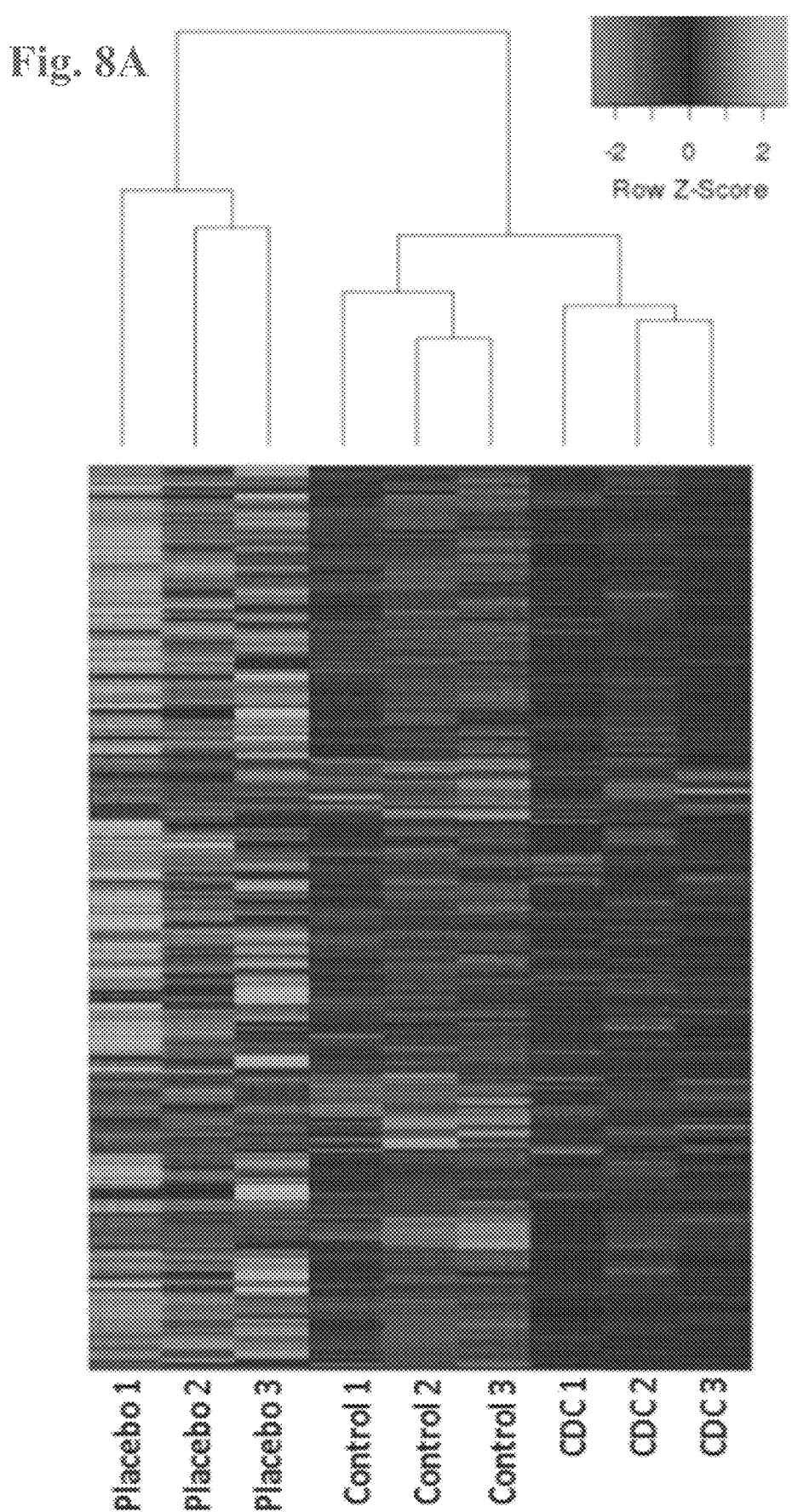
(FIG. 8A) Heat map showing the transcripts which are up- or down regulated by HFpEF and normalized partially or completely by CDC-treatment.
Figure 8B:
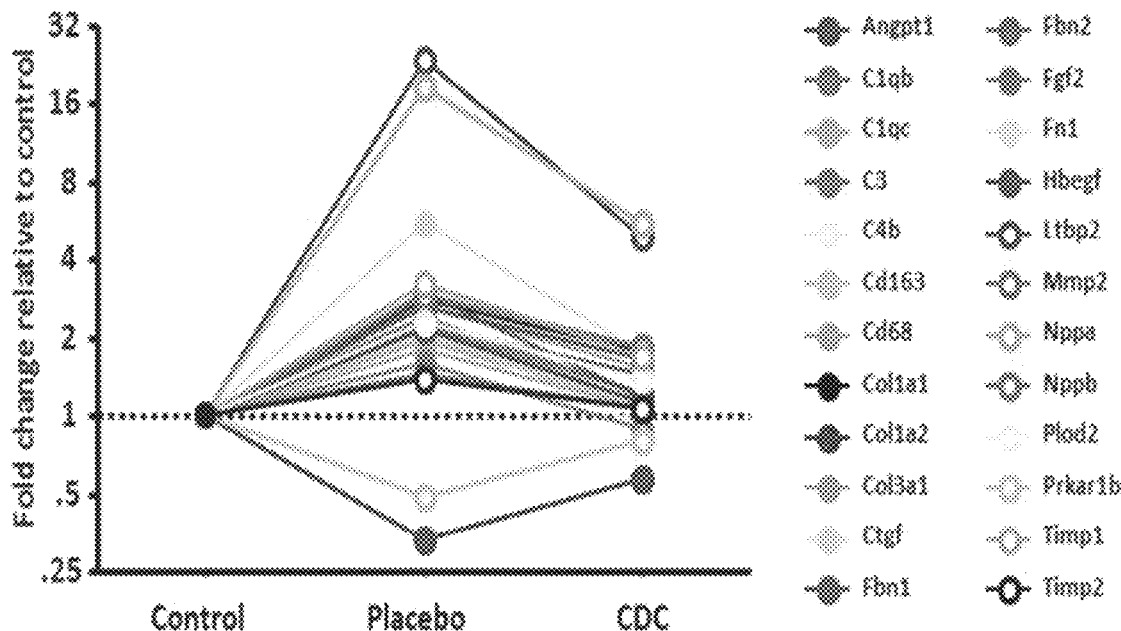
(FIG. 8B) Selected genes involved in inflammation and fibrosis or associated with HFpEF which are rescued by CDC-treatment.
Figure 8C:
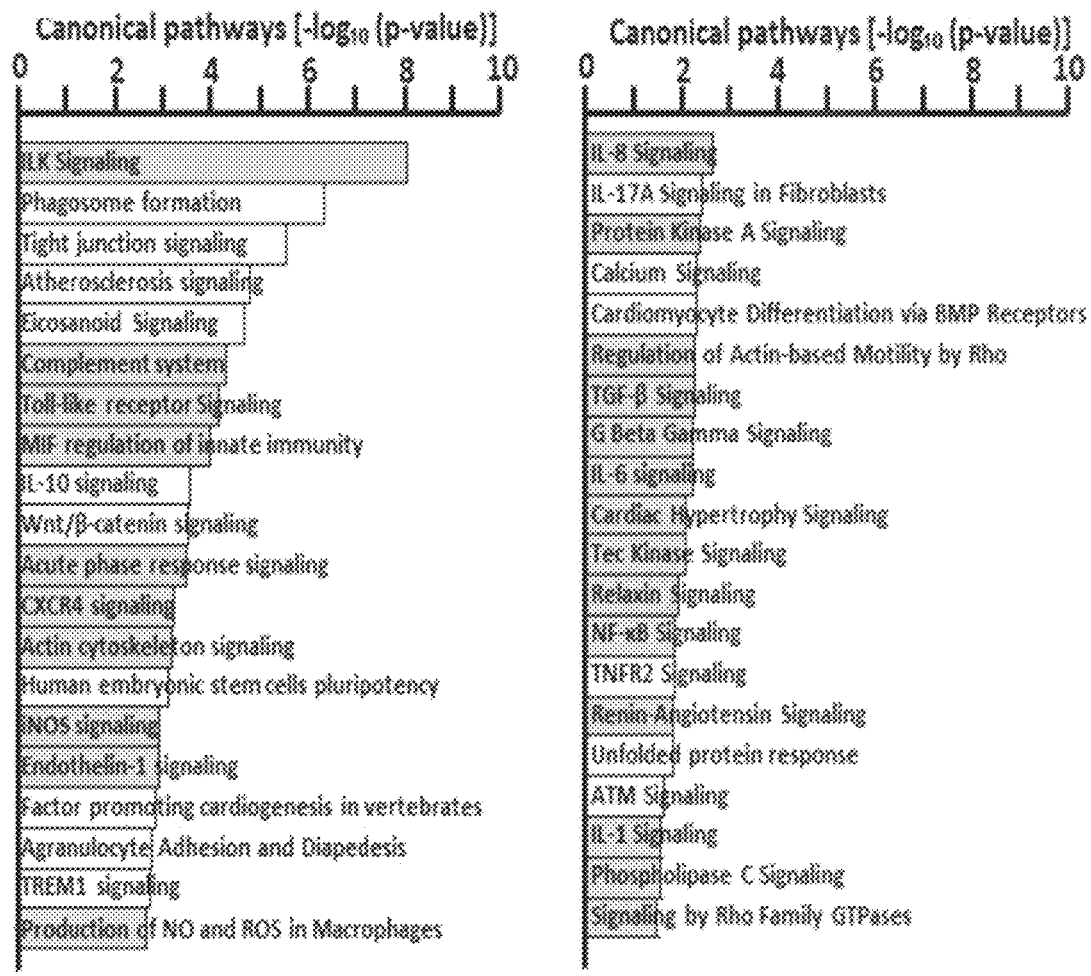
(FIG. 8C) Selected pathways modified by CDC-treatment compared to placebo; blue: inhibited, orange: activated, white: not clear from the database (literature missing).
Figure 10A:
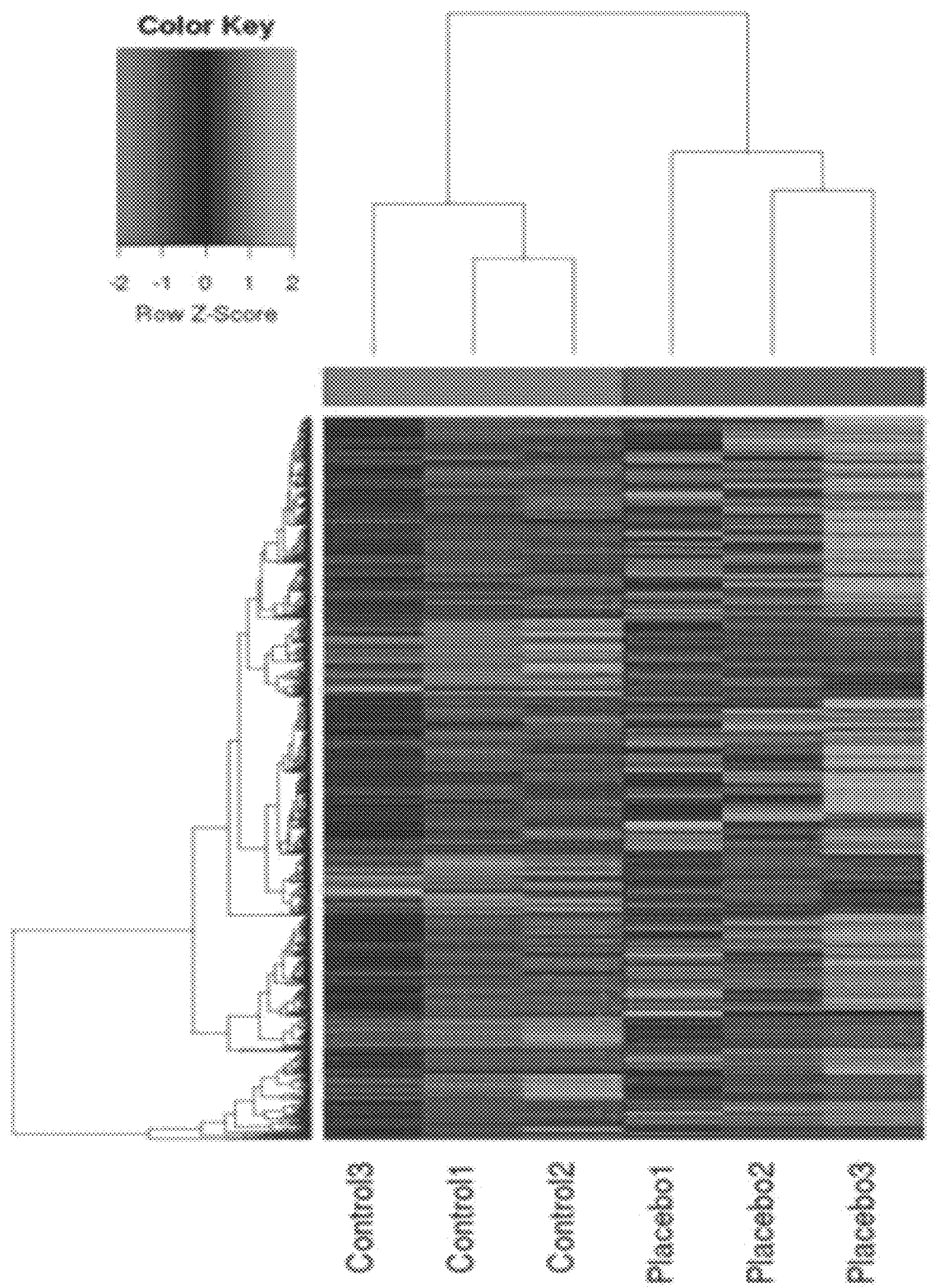
FIG. 10: Heat map comparing gene expression in placebo-treated and control rat hearts (FIG. 10A), CDC- and placebo-treated rat hearts (FIG. 10B) and control and CDC-treated rat hearts (FIG. 10C).
Figure 10B:
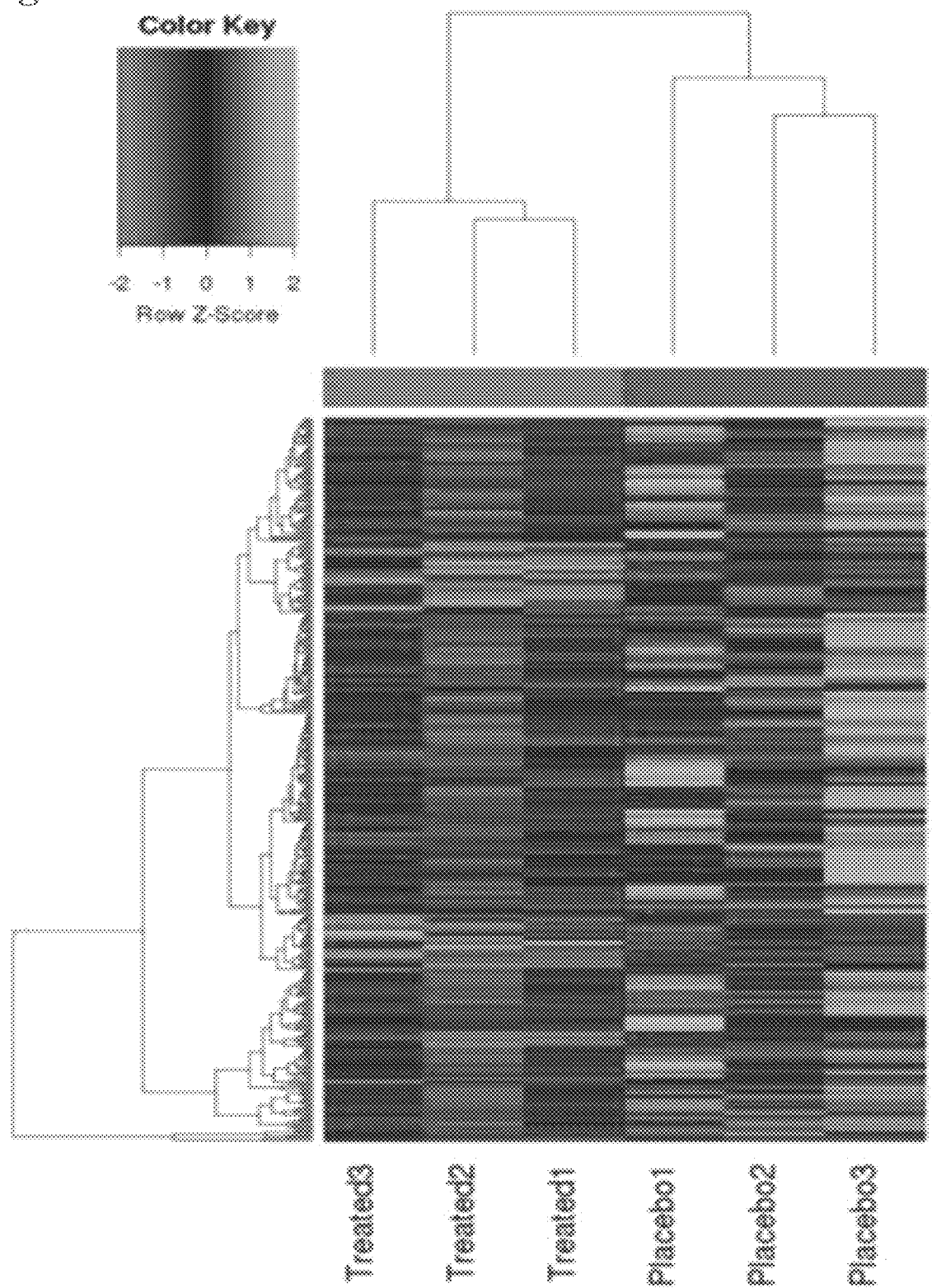
Figure 10C:
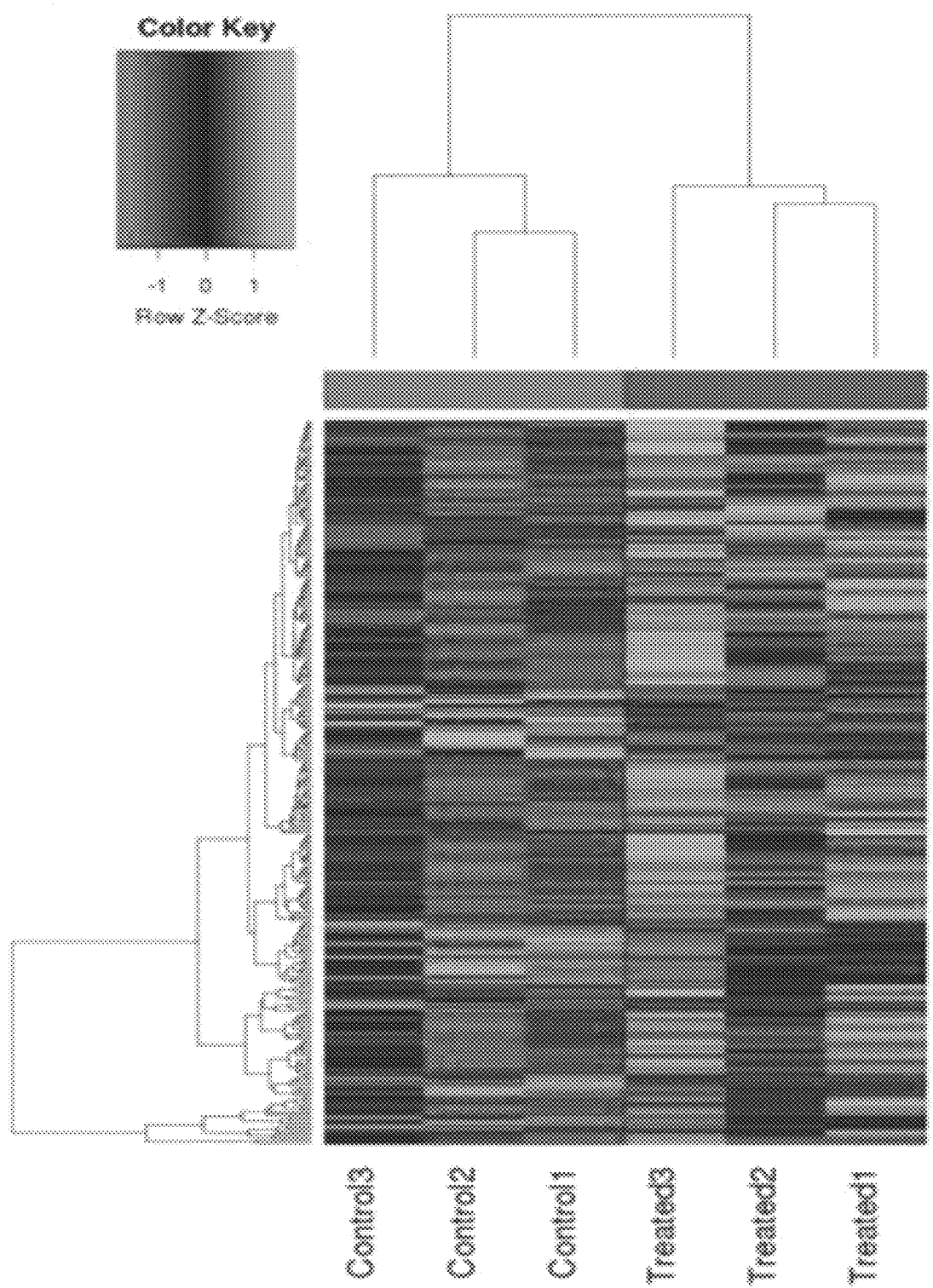

Next generation RNA sequencing. Next generation sequencing was performed in the 3 groups. FIG. 10A-C shows head-to-head pairwise comparison of gene expression in the 3 groups. The heat maps reveal that the HFpEF phenotype is associated with major global changes in gene expression as shown by the placebo vs. control comparison (FIG. 10A). More important, the CDC vs. placebo comparison (FIG. 10B) reveals that CDC-treatment dramatically changed gene expression. Interestingly, >300 genes whose expression was up- or down regulated in HFpEF (i.e., in high-salt placebo hearts) had their expression levels "rescued" by CDC treatment (FIG. 8A). Some of these transcript changes involved genes which underlie HFpEF-related pathophysiologic features that have been identified (non-exhaustive list shown in FIG. 8B). Indeed, key genes involved in fibrosis, inflammation and macrophage signaling, or associated with the consequences of HFpEF (brain natriuretic and atrial natriuretic peptides) were up-regulated in placebo hearts but returned fully or partially to control levels after CDC-treatment. These profound changes in the transcriptome reveal HFpEF-related activation, and CDC-induced inhibition, of key disease-associated signaling and effector pathways (FIG. 8C).

Example 20

Summary of Findings

CDCs normalized LV relaxation and improved survival in a rat model of HFpEF, without blunting hypertension or hypertrophy. The selective correction of functional HFpEF abnormalities creates an unprecedented opportunity for mechanistic insights. Potentially causal pathways (i.e., those that accompany the abnormalities in HFpEF) can now be distinguished from those that are merely associative. The Inventors' findings indicate that fibrosis and inflammation are causative in HFpEF: reductions in those two pathophysiological processes underlie the resolution of HFpEF, while hypertrophy and hypertension remain unchanged.

In hypertensive rats fed with a high-salt diet, hypertension associated with left ventricular (LV) hypertrophy and diastolic dysfunction was observed, without impairment of ejection fraction. After receiving intracoronary CDCs ($5 \times 10^5$) or placebo for 4 more weeks, early-to-late ventricular filling (E/A) ratio returned to normal in CDC-treated rats but remained depressed in placebo. Tau and end-diastolic pressure volume relationship were higher in placebo-treated rats than in CDC-treated rats and control. Improved LV relaxation was also associated with lower LV end-diastolic pressure, decreased lung congestion and enhanced survival (80% vs. 48%) in CDC-treated rats. Histological analysis revealed no decrease in cardiac hypertrophy after CDC treatment, consistent with sustained, equally-elevated blood pressure in CDC- and placebo-treated rats. Nevertheless, CDC treatment decreased LV fibrosis and collagen 1A1 and 3 mRNA expression levels, while increasing microvascular density. Inflammatory infiltrates (CD68+ and CD45+ cells) in the LV, and serum inflammatory cytokines (MCP-1, IL-6 and TNF-α), were decreased after CDC treatment. As such, CDCs normalized LV relaxation and LV diastolic pressure while improving survival in a rat model of HFpEF. These functional benefits occurred despite persistent hypertension and hypertrophy. By reversing inflammation and fibrosis, CDCs are beneficial in the treatment of HFpEF.

Example 21

Discussion

The Inventors have demonstrated that cell therapy by CDCs can reverse the functional abnormalities of HFpEF and improve survival in a rat model of hypertension-induced HFpEF. The CDC-induced reversal of HFpEF occurred without reductions in either blood pressure or cardiac hypertrophy. The Inventors' findings indicate fibrosis and inflammation are causative in HFpEF: reductions in those two pathophysiological processes underlie the resolution of HFpEF, while hypertrophy and hypertension remain unchanged.

Cardiac hypertrophy has long been thought to be the linchpin in HFpEF. However, several recent studies in animal models and humans have implicated inflammation and collagen infiltration. Hypertension and other comorbidities can favor a systemic pro-inflammatory state with high circulating cytokine levels, including IL-6, TNF-α and MCP-. Inflammation leads to activation, recruitment and trans-endothelial migration of leukocytes and monocytes/macrophages into the heart. These inflammatory cells contribute to LV fibrosis by promoting the differentiation of fibroblasts into myofibroblasts. The resulting increase in LV collagen content is the main contributor to the increase in passive myocardial fiber stiffness, a major component of diastolic impairment in HFpEF. The observed phenotypic improvements after CDC treatment were associated with decreases in circulating inflammatory cytokines (including IL-6, TNF-α and MCP-1) and less myocardial inflammation. In addition, collagen production was increased in placebo treated animals but fell markedly after CDC treatment. The parallel decrease in TIMP-1 (FIG. 6) suggests that collagen clearance was increased in CDC-treated animals. In addition, myofibroblast infiltration, collagen content, and collagen production were increased in placebo-treated animals but fell markedly after CDC treatment. The parallel decrease in transcripts for MMPs and TIMPs (FIG. 9) suggests increased extracellular matrix turnover in the placebo-treated animals which is normalized by CDC-treatment. These findings show that proinflammatory and profibrotic stimuli play a major role in the development of HFpEF. The mechanism whereby CDCs modify inflammation and fibrosis involves major changes in gene expression (FIG. 8C). Such changes are long-lasting, as the transcriptome was analyzed 4 weeks after CDC injection (at which point injected allogeneic cells are no longer detectable). This affirms the role of CDC-derived exosomes laden with microRNAs and other noncoding RNAs that collectively mold the target transcriptome. The drastic changes in the expression of the genes involved in fibrosis and inflammation seen here appear to be in vivo manifestations of exosome-mediated phenotypic conversions.

It is noteworthy that no changes in the magnitude of cardiac hypertrophy were observed after CDC treatment. Cardiac hypertrophy assessed by 3 different techniques (echocardiography, heart weight, and cardiomyocyte cross-sectional area) was present and virtually identical in both high-salt groups at endpoint but not in control. Here, decreased inflammation and fibrosis underlie the resolution of HFpEF, despite persistent hypertrophy and hypertension. Thus, attenuation of cardiac hypertrophy is not required to normalize diastolic function.

Microvascular dysfunction and rarefaction have been reported as additional contributors to HFpEF. Several studies have shown that, even in the absence of coronary artery disease, patients with HFpEF have fewer microvessels and lower coronary reserve. In addition to their anti-inflammatory and anti-fibrotic properties, CDCs are able to promote the growth of new vessels. The Inventors observed an increase in the numbers of arterioles and capillaries in the LV after CDC treatment (FIG. 7). Cardiosphere-related increases in vessels by histology were associated with augmented myocardial perfusion and coronary reserve.

Example 22

CDCs Lower Risk of Arrhythmias in HFpEF

Figure 12:
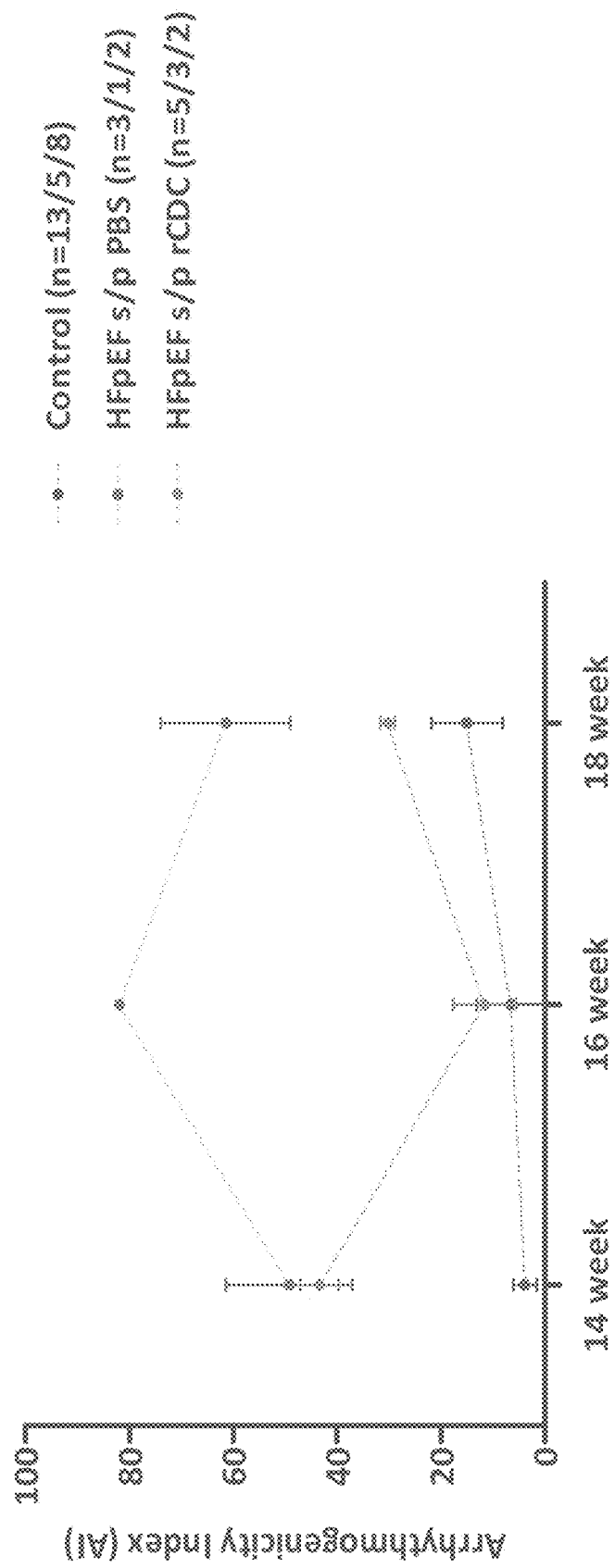
FIG. 12: Arrhythmogenicity index (AI) was calculated as (number of arrhythmia beats+coupling interval of last stimuli−40)/square root of number of extra stimuli. AI was decreased in rCDC-injected rats compared to PBS-injected animals at 18 weeks of age (30.4 vs. 61.5). (P value was non-significant due to low N)
Figure 13:
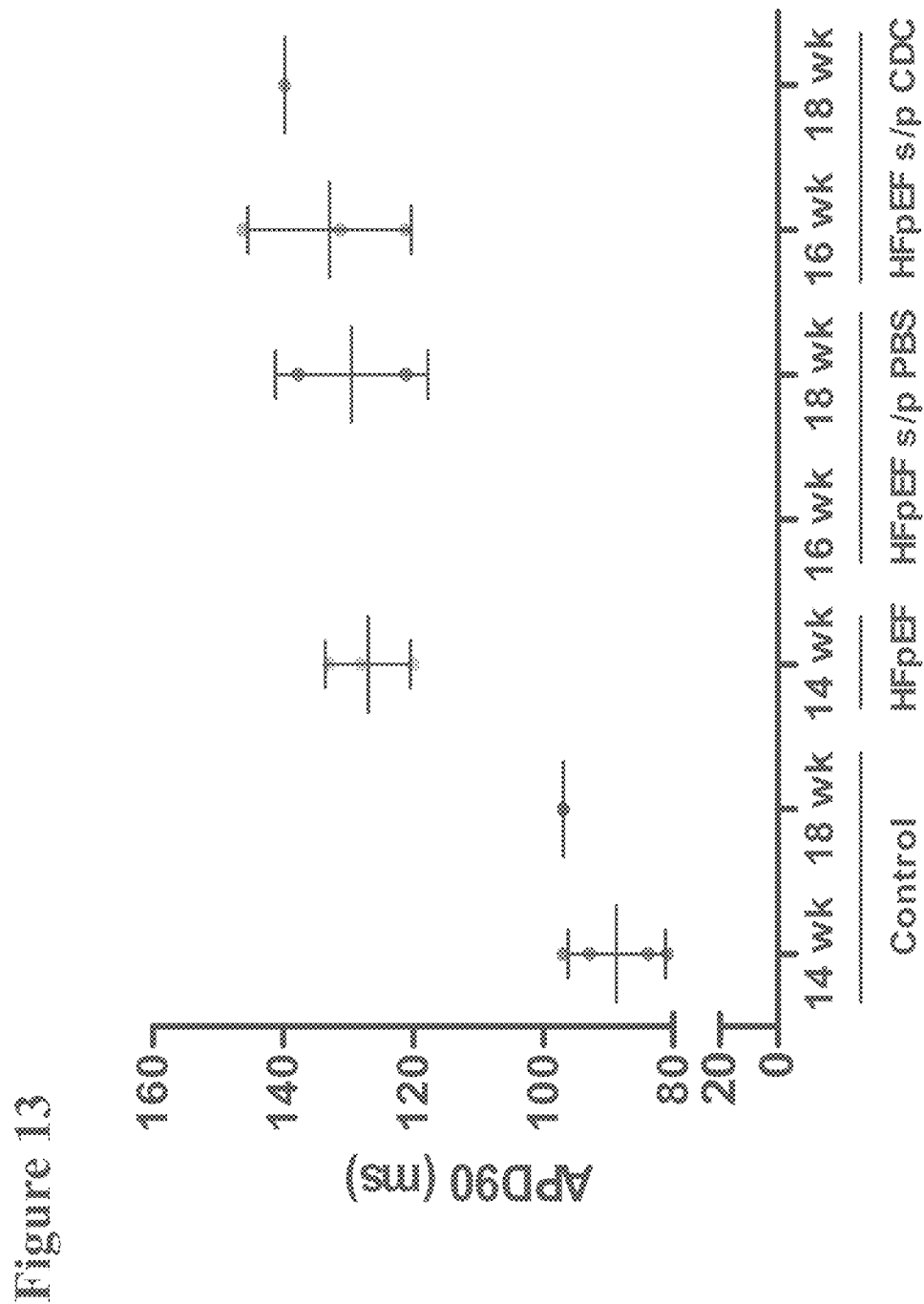
FIG. 13: Action potential duration (APD90) can be checked with optical mapping system.
Figure 14:
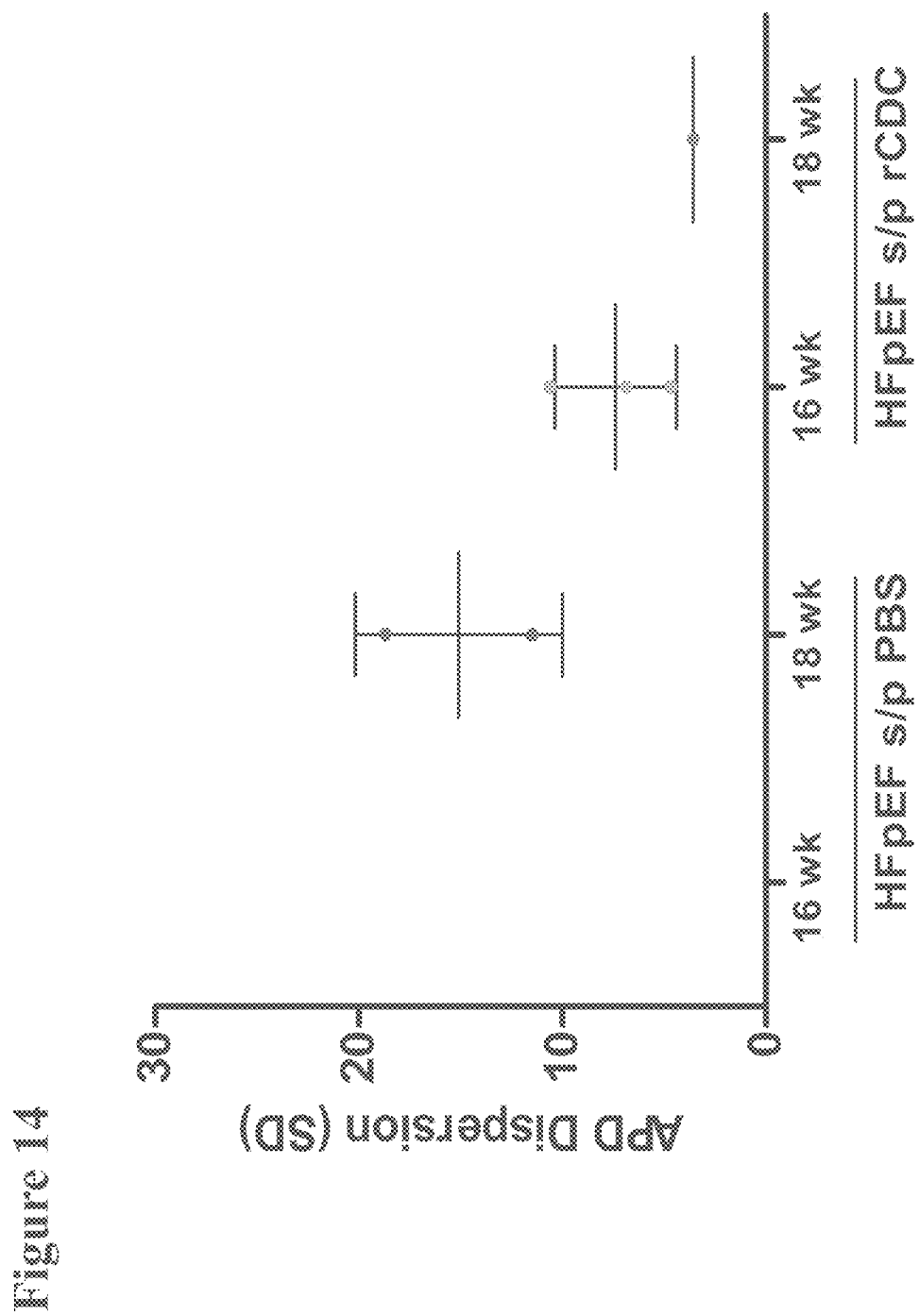
FIG. 14: APD 90 dispersion was checked in different regions of the heart using optical mapping system. CDCs appear to decrease APD dispersion.
Figure 15:
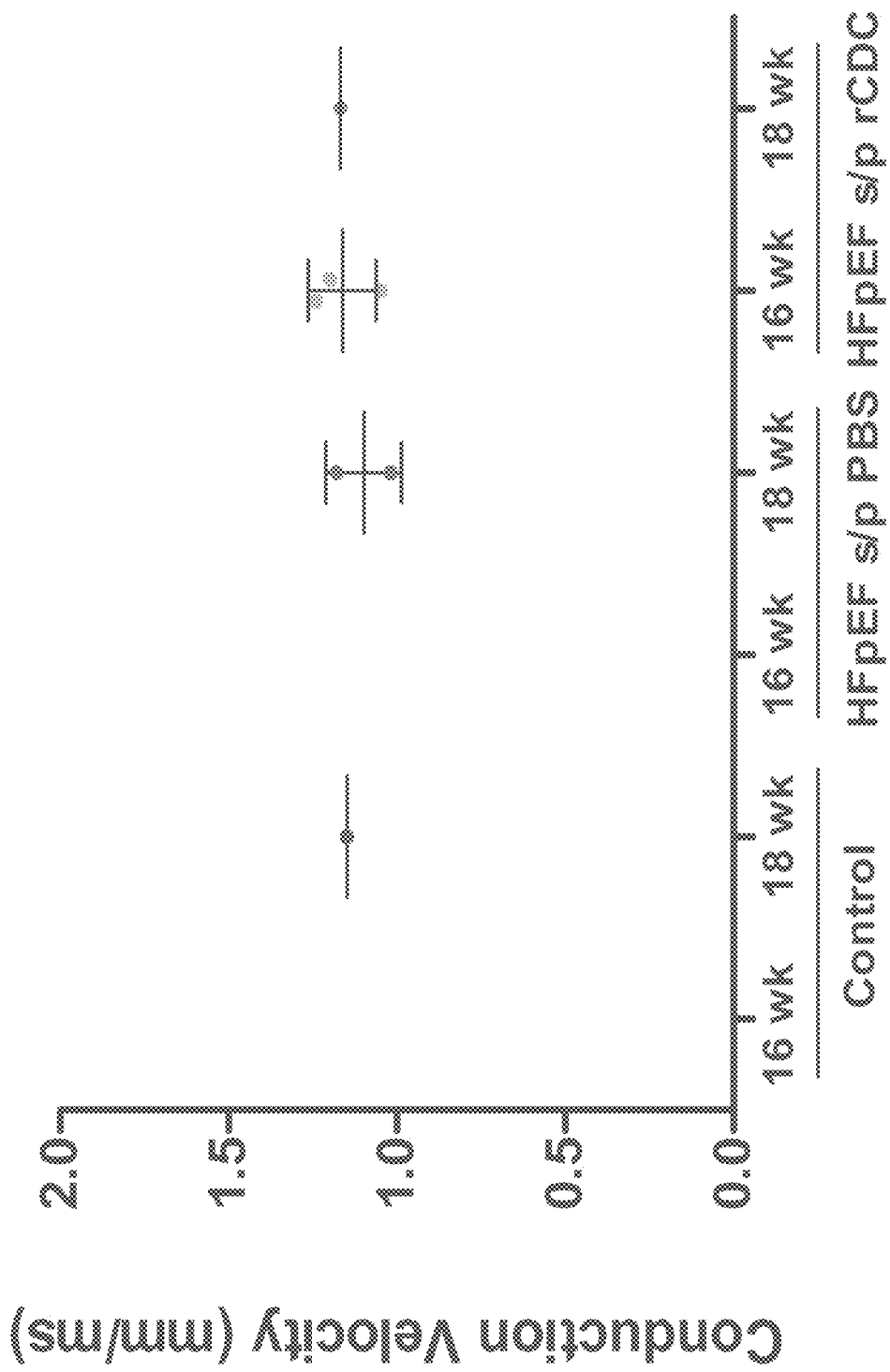
FIG. 15: Conduction Velocity (Depolarization) Conduction velocity was checked during depolarization using optical mapping system.
Figure 16:
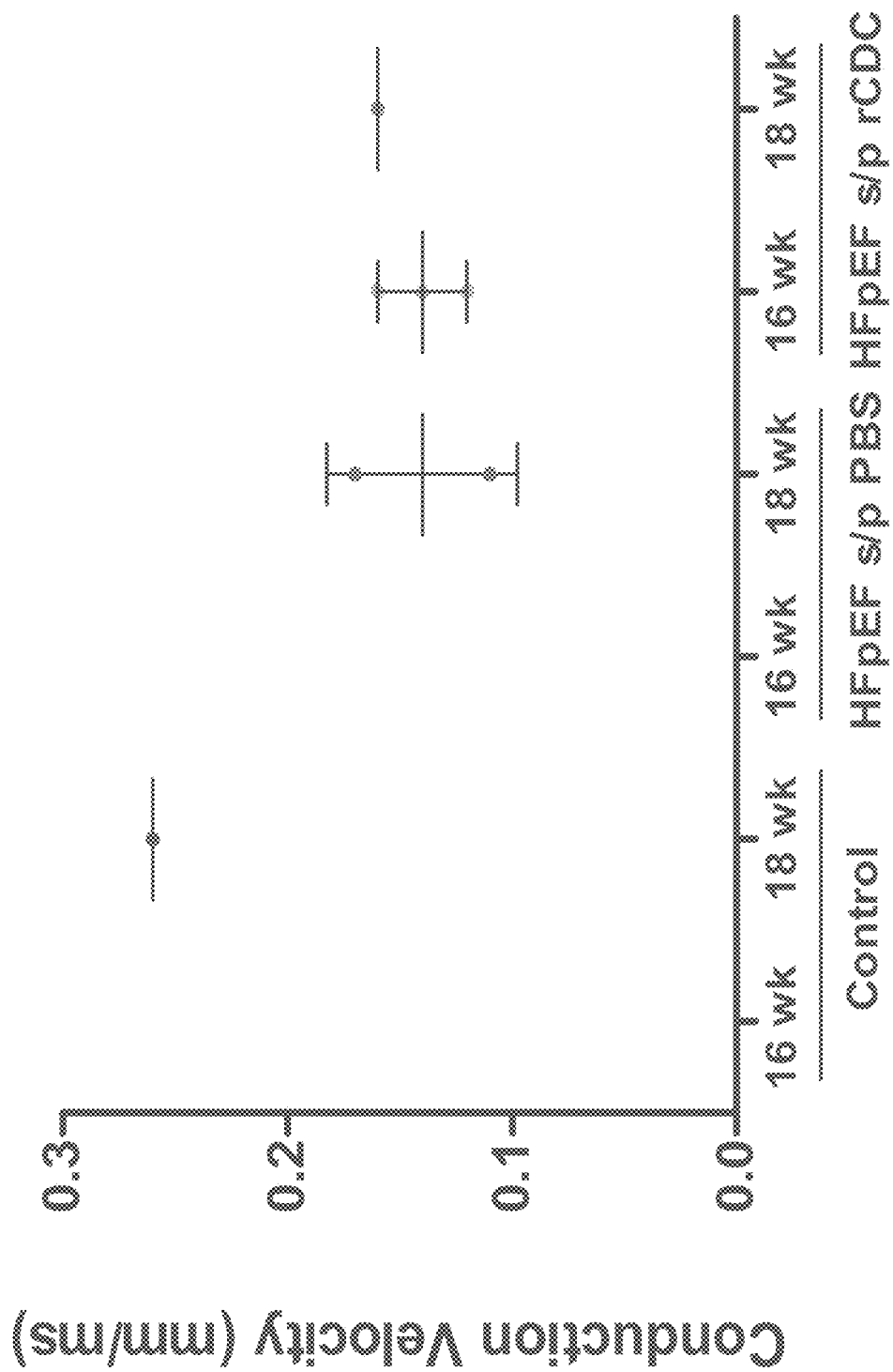
FIG. 16: Conduction Velocity (Repolarization) Conduction velocity was checked during repolarization using optical mapping system.

As shown in FIG. 12, arrhythmogenicity index (AI) was calculated as (number of arrhythmia beats+coupling interval of last stimuli−40)/square root of number of extra stimuli. AI was decreased in rCDC-injected rats compared to PBS-injected animals at 18 weeks of age (30.4 vs. 61.5). As shown in FIG. 13, action potential duration (APD90) was checked with optical mapping system. ADPD 90 dispersion was checked in different regions of the heart using optical mapping system and CDC administration appeared to decrease APD dispersion as shown in FIG. 14. As shown in FIG. 15, conduction velocity (depolarization) was checked during depolarization using optical mapping system and as shown in FIG. 16 conduction velocity (repolarization) was checked during repolarization using optical mapping system.

Example 23

Exosomes and CDC Activity

Figure 11:
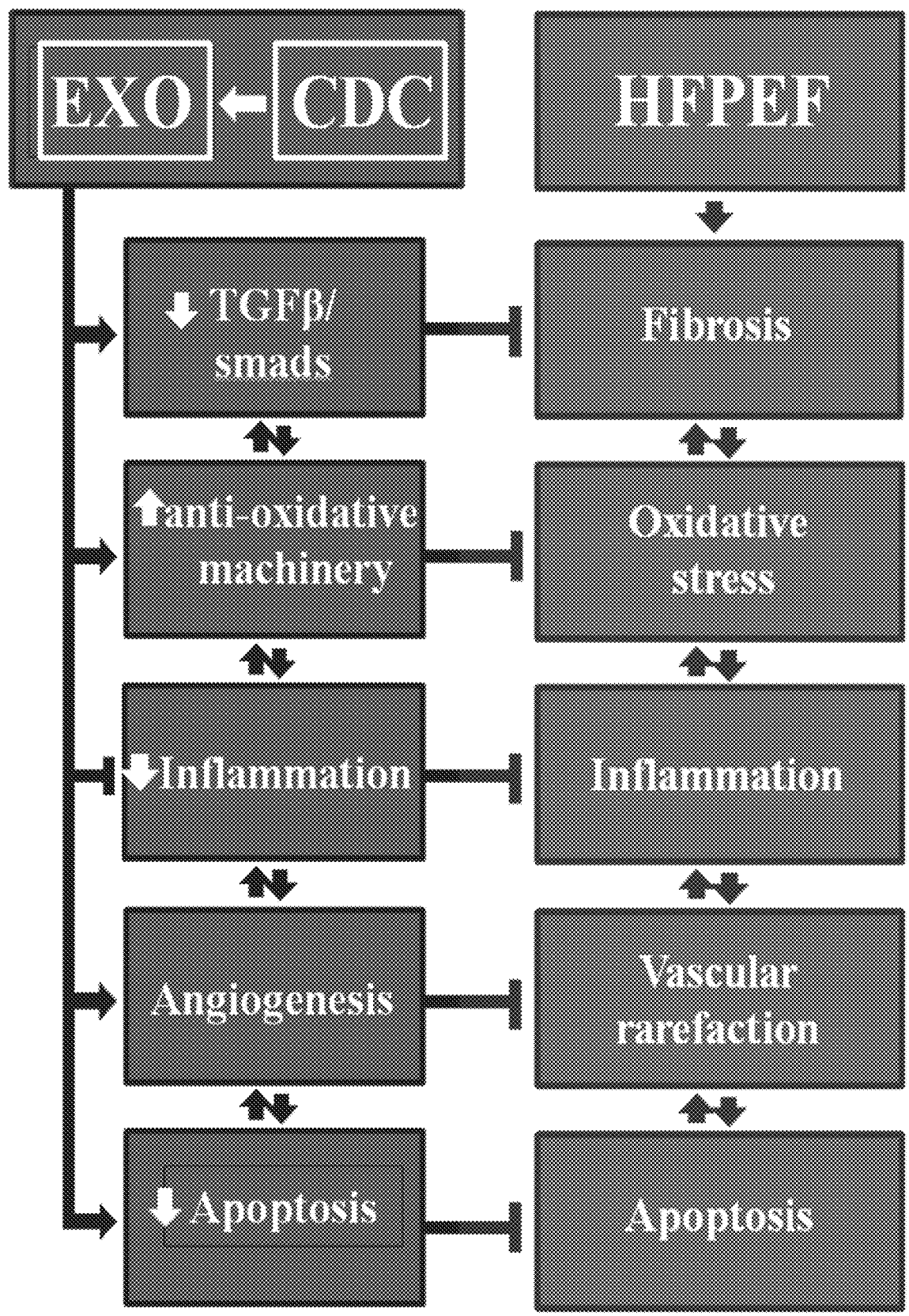
FIG. 11: How known features of CDCs might improve HFpEF, including secreted exosomes and their RNA payloads.
Figure 17A:
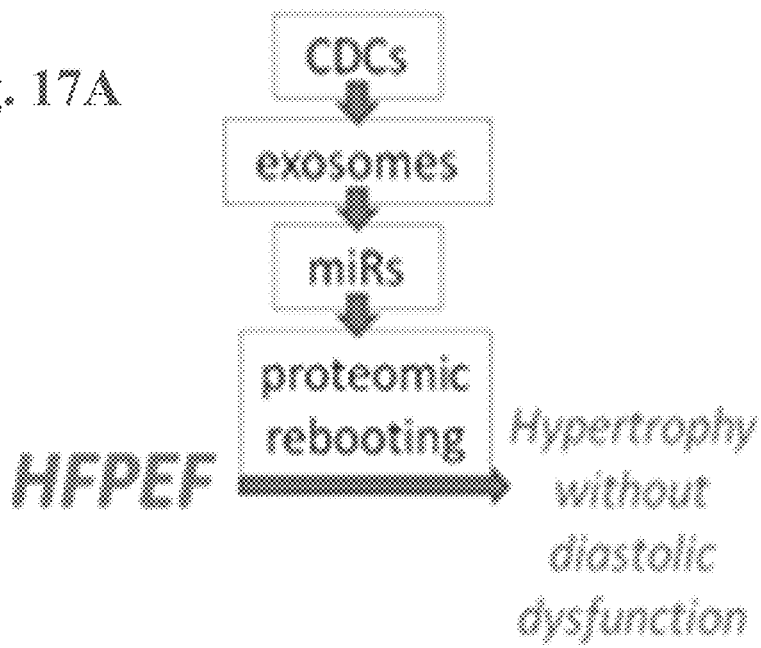
(FIG. 17A) Exemplary model for exosome activity in HFpEF.

The above described results establish virtues of CDCs retarding HFpEF (FIG. 11). Extending these results, growing evidence indicate that exosomes are critical agents of the indirect effects of CDCs, likely due to the transfer of microRNAs (e.g., miR-146a) from CDCs to surrounding heart tissue. The role of exosomes in CDC-induced improvements in HFpEF are further studied and described herein. While not wishing to be bound by any particular theory, the Inventors believe that CDCs are capable of effectively treating HFpEF by secreting exosomes that transfer microRNAs to the heart, leading to coordinated changes in gene expression, proteomic "rebooting," and inhibition of key fibrotic and inflammatory pathways in the myocardium. Alterations in the proteome, orchestrated by exosomal miRs, underlie the functional abnormalities in HFpEF, and CDC treatment selectively resets/recruits cellular responses so as to reduce fibrosis and inflammation, and reestablish physiological Ca$^{2+}$ handling and contractile function. This model is depicted schematically in FIG. 17A.

Figure 17B:
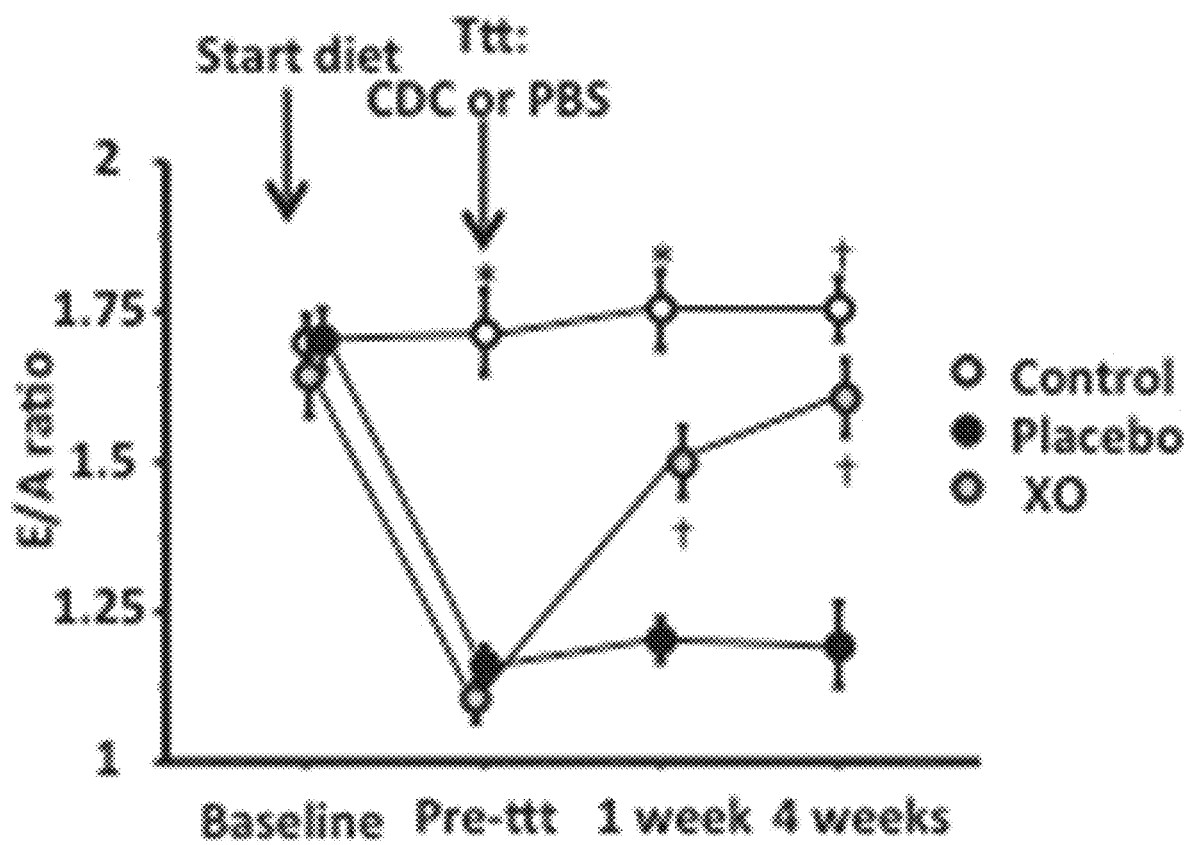
(FIG. 17B) CDC-derived exosomes (XO) reverse E/A ratio abnormalities in DS rats with HFpEF. *P<0.05 vs. placebo, and exosomes; †P<0.05 vs. placebo.

Experiments have identified an effective dose of human CDC-derived exosomes in the aforementioned DS rat model: FIG. 17B shows that intramyocardial injection of human CDC-derived exosomes (350 μg protein divided among 4 LV sites) tends to normalize the E/A ratio measured by echo. Exoquick® and/or ultracentrifugation will be used to isolate exosomes from conditioned media.

One can quantify size distribution using Nanosight® particle counter; if needed, 0.45 μm filters or sucrose gradients can be applied to enrich the exosome fraction. Purity is additionally be checked by quantification of exosome-characteristic tetraspanin proteins. As exosomes are likely mediators of CDC benefits in HFpEF, and permeabilized exosomes turn out not to be bioactive, one can search for individual miRs that confer key therapeutic properties.

Example 24

Further Exosome Studies

Figure 18:
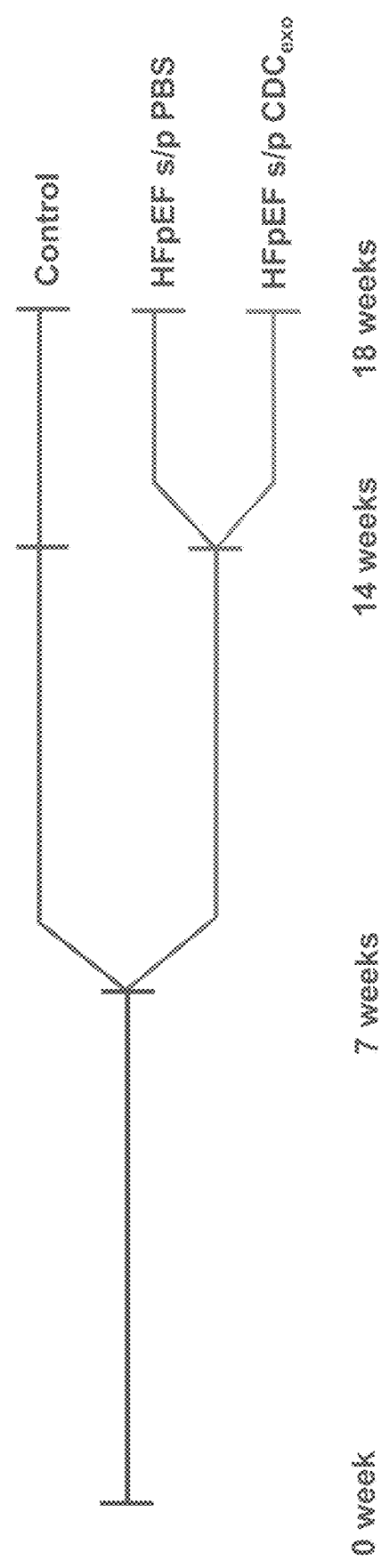
FIG. 18: For CDC-derived exosome experiments, Dahl salt-sensitive rats were fed high-salt (HS) diet from 7 weeks of age to induce HFpEF. Normal-salt (NS) fed rats served as controls. At 14 weeks of age, diastolic dysfunction was confirmed with echocardiogram. Human CDC-derived exosomes (CDCexo) (300-400 ug) were injected intra-myocardially (4 different sites) to HFpEF rats. Follow-up experiments were performed 4 weeks after the injection. PBS-injected HFpEF rats served as placebo.

As shown in FIG. 18, for CDC-derived exosome experiments, Dahl salt-sensitive rats were fed high-salt (HS) diet from 7 weeks of age to induce HFpEF. Normal-salt (NS) fed rats served as controls. At 14 weeks of age, diastolic dysfunction was confirmed with echocardiogram. Human CDC exosomes (CDC-derived exosomes) (300-400 ug) were injected intra-myocardially (4 different sites) to HFpEF rats. Follow-up experiments were performed 4 weeks after the injection. PBS-injected HFpEF rats served as placebo.

Figure 19:
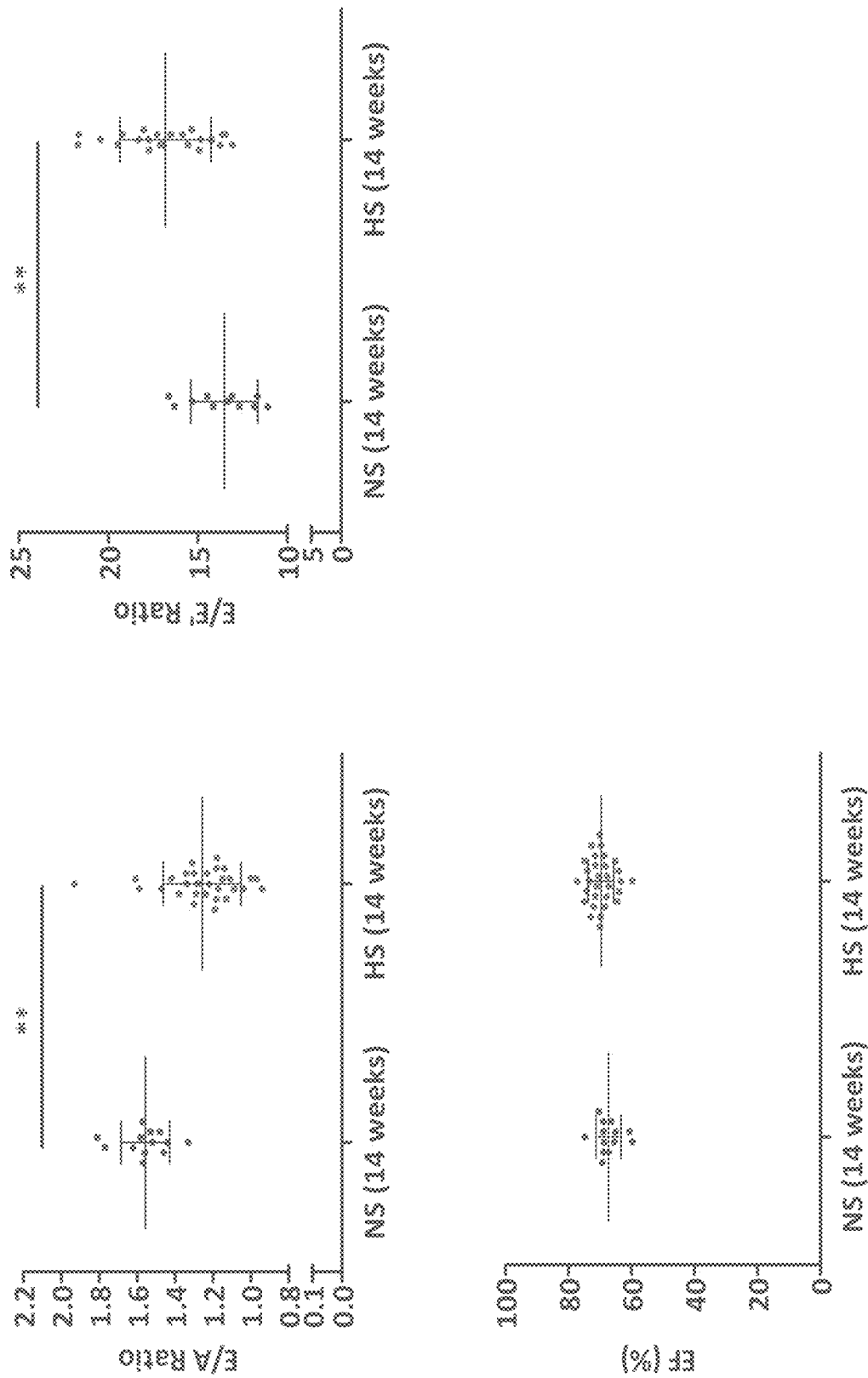
FIG. 19: Echocardiogram At 14 weeks of age, echocardiogram was performed to check systolic and diastolic functions. Early-to-late ventricular filling E/A ratio was decreased in HS-fed rats compared to NS-fed animals (1.26±0.20 vs. 1.56±0.13, p<0.001) and Early filling (E) to early diastolic mitral annular velocity (E') E/E' ratio was increased in HS group compared to NS rats (16.82±2.54 vs. 13.53±1.87, p<0.001), which indicate the development of diastolic dysfunction. Ejection fraction (EF) did not differ between the two groups (67.30±3.96 vs. 69.74±4.04, p=0.075).
Figure 20:
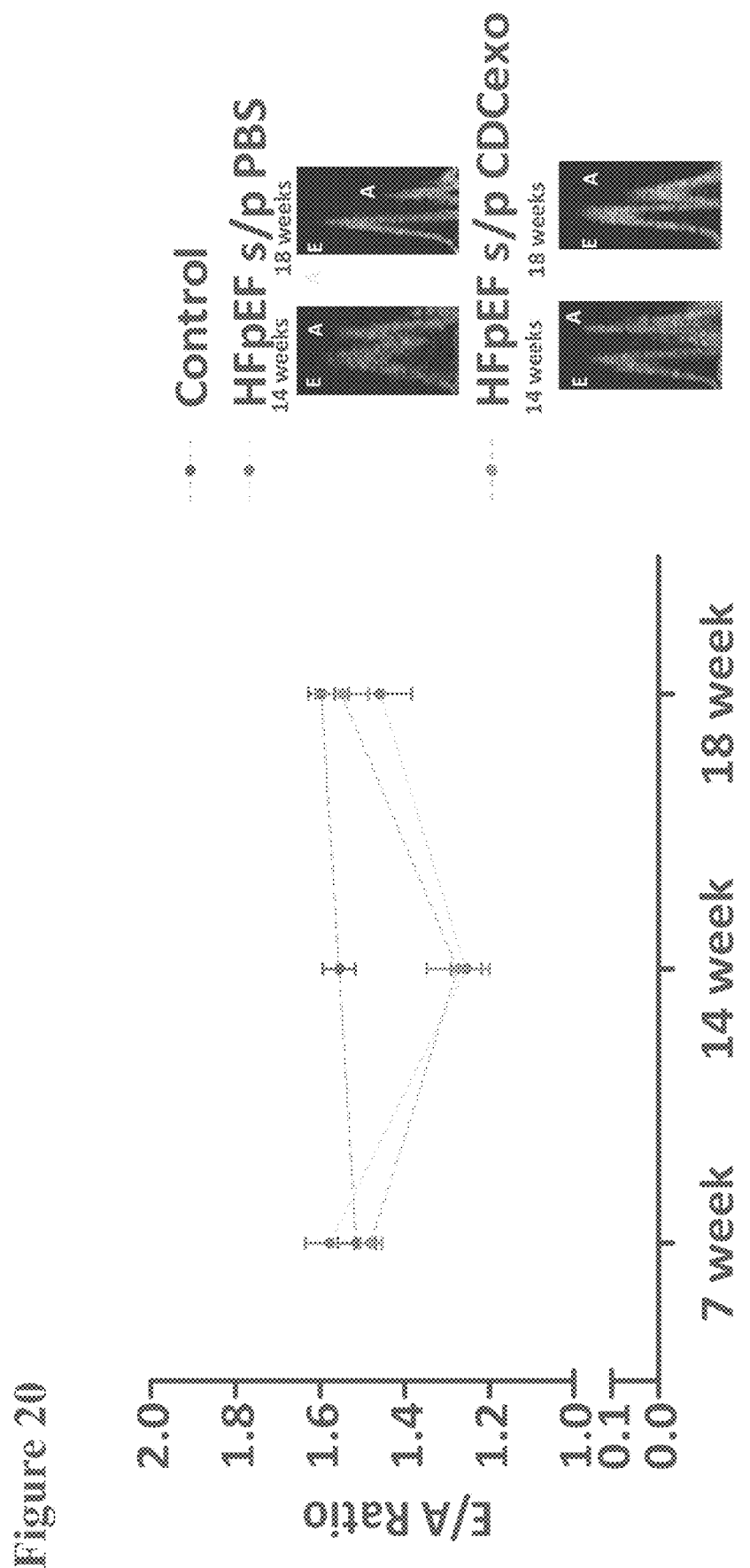
FIG. 20: Early-to-late ventricular filling (E/A) ratio four weeks after the injection of CDC-derived exosome (CDCexo) and PBS, echocardiogram was performed to check the systolic and diastolic functions. E/A ratio normalized in both of CDC-derived exosome and PBS-treated groups (1.57±0.16 vs. 1.46±0.17, p=0.189).

At 14 weeks of age, echocardiogram was performed to check systolic and diastolic functions as shown in FIG. 19. E/A ratio was decreased in HS-fed rats compared to NS-fed animals (1.26±0.20 vs. 1.56±0.13, $p<0.001$) and E/E' ratio was increased in HS group compared to NS rats (16.82±2.54 vs. 13.53±1.87, $p<0.001$), which indicate the development of diastolic dysfunction. Ejection fraction (EF) did not differ between the two groups (67.30±3.96 vs. 69.74±4.04, $p=0.075$). As shown in FIG. 20, E/A Ratio Four weeks after the injection of CDC-derived exosomes and PBS, echocardiogram was performed to check the systolic and diastolic functions. E/A ratio normalized in both of CDC-derived exosomes and PBS-treated groups (1.57±0.16 vs. 1.46±0.17, $p=0.189$).

Figure 21:
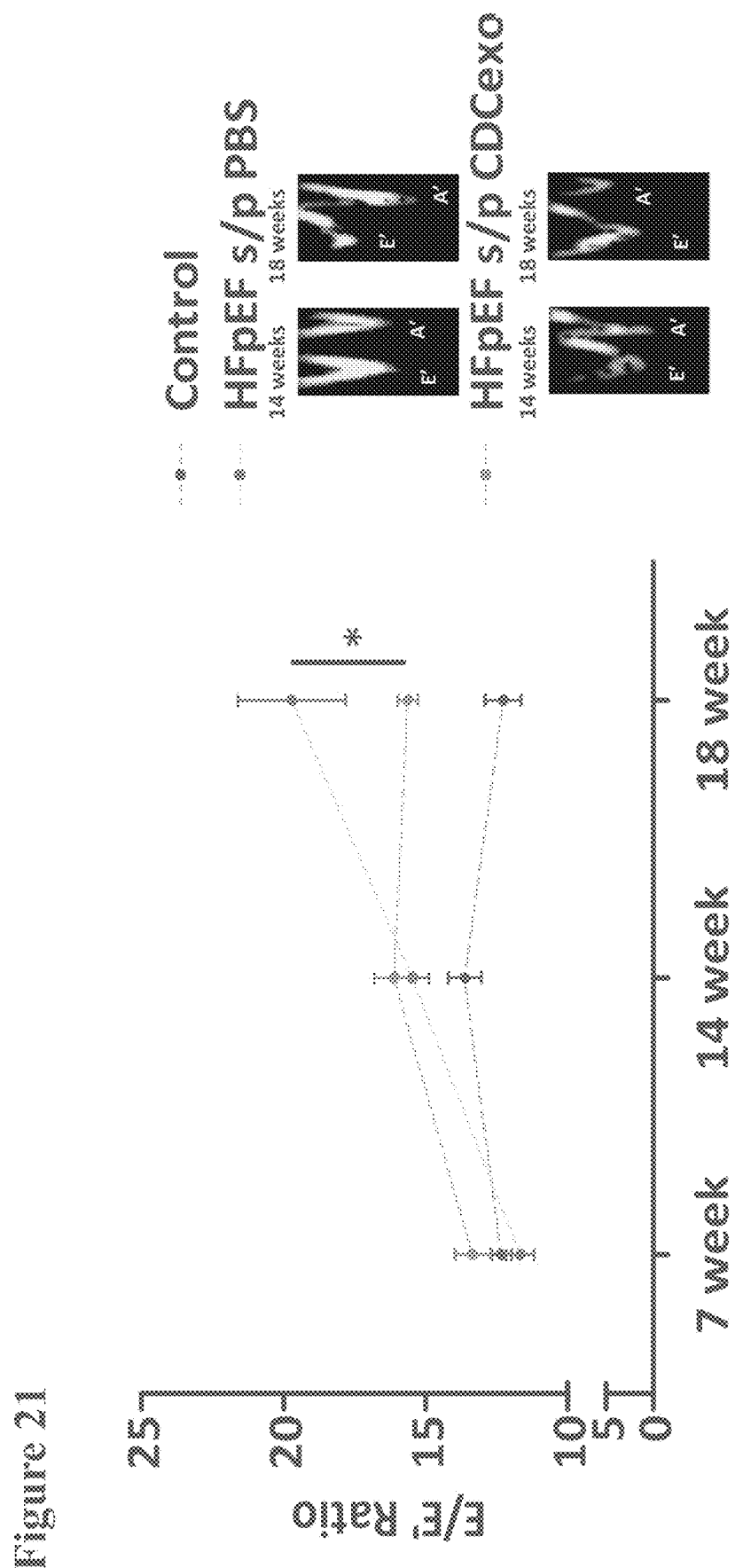
FIG. 21: Early filling (E) to early diastolic mitral annular velocity (E') E/E' ratio was decreased in CDC-derived exosome (CDCexo)-treated rats compared to PBS-injected animals (15.62±0.93 vs. 19.71±4.25, p=0.031). These indicate improvement of diastolic dysfunction in CDCexo-injected HFpEF rats compared to placebo animals.
Figure 22:
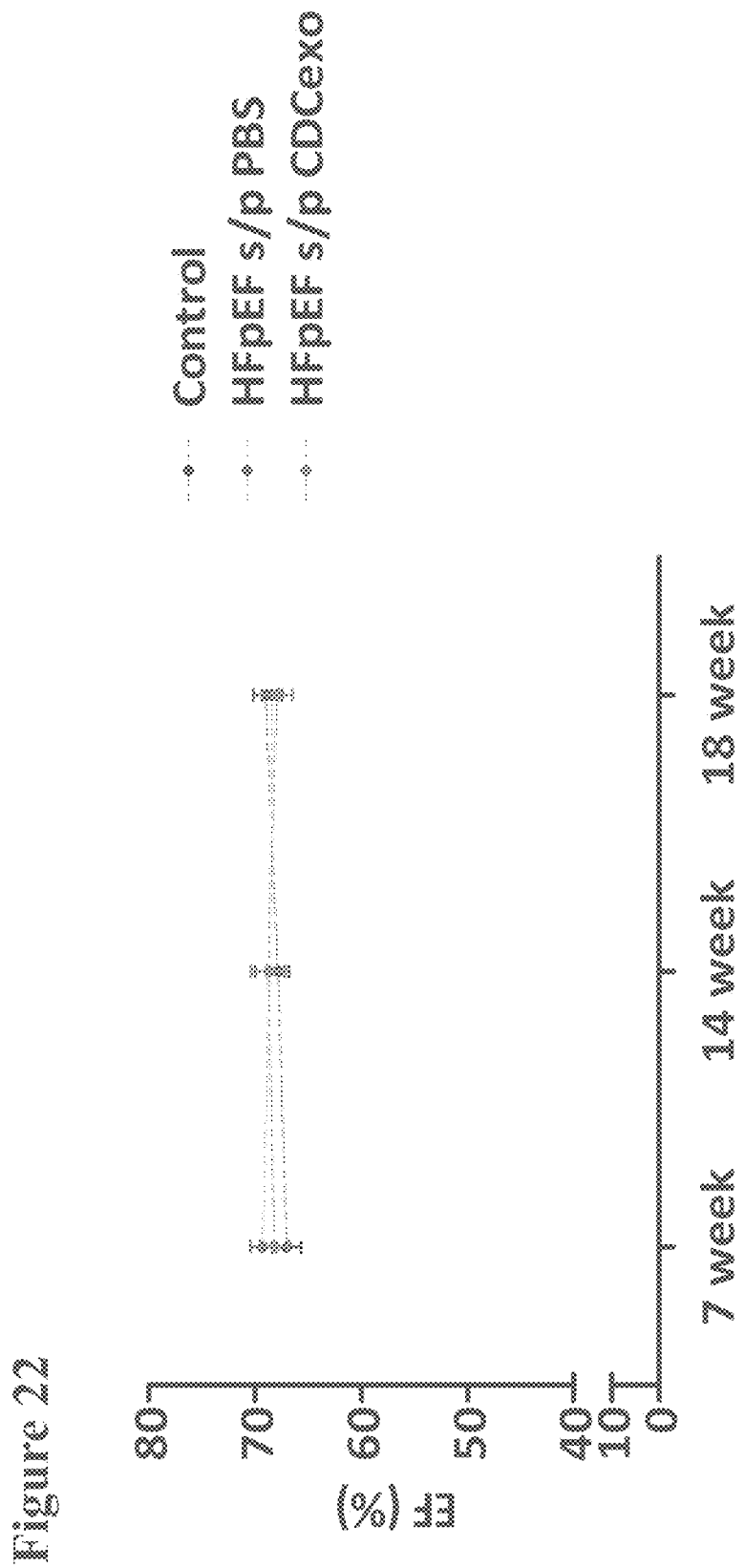
FIG. 22: Ejection fraction (EF) did not change between CDC-derived exosome (CDCexo) and PBS-treated rats (68.42±2.14 vs. 69.12±6.21, p=0.161).
Figure 23:
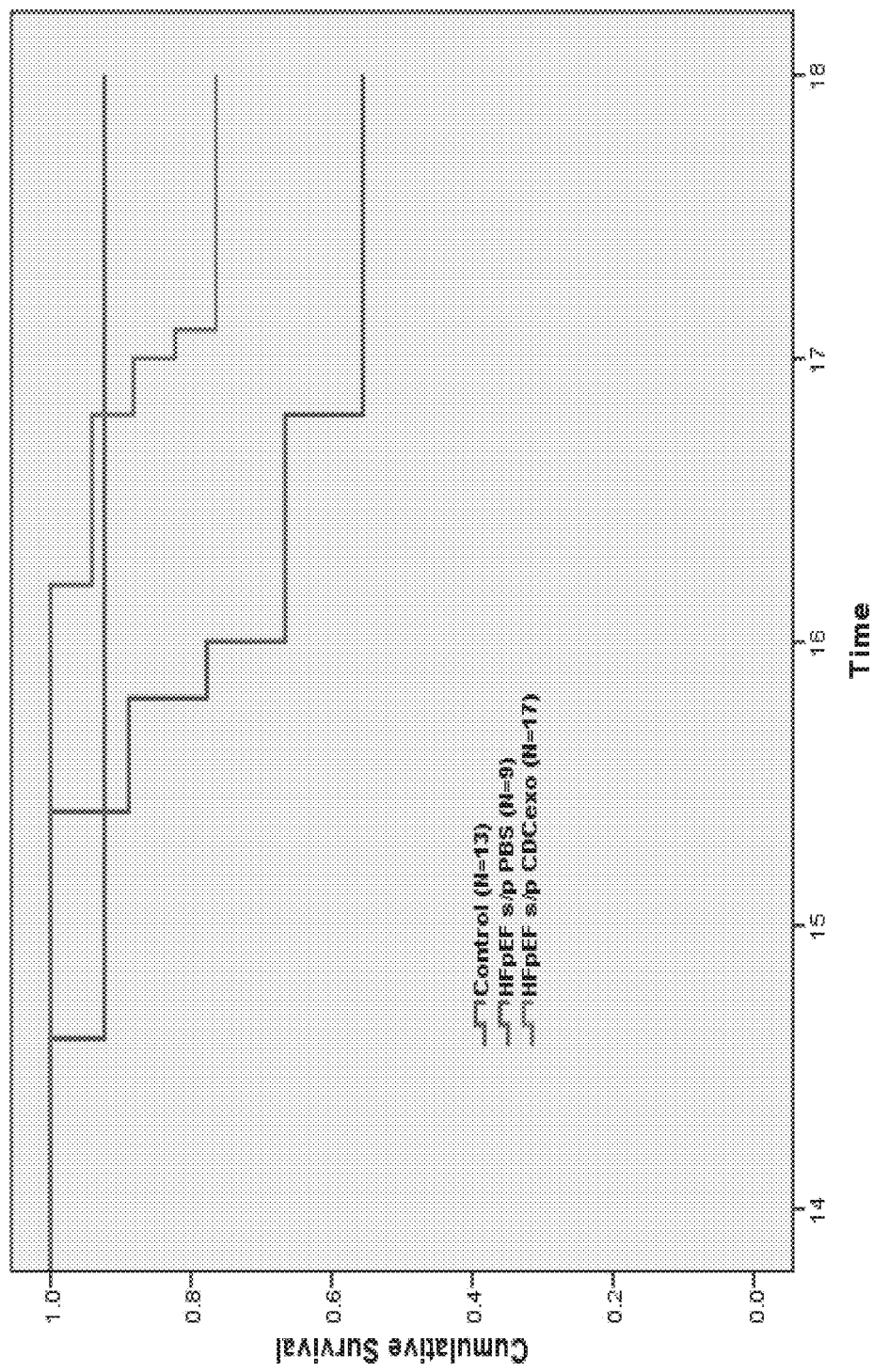
FIG. 23: Kaplan-Meier survival analysis showed a trend towards decreased mortality in CDC-derived exosome (CDCexo)-treated rats compared to PBS-injected animals (4/17=23.5% vs. 4/9=44.4%, Log rank 0.176).

However, E/E' was decreased in CDC-derived exosomes-treated rats compared to PBS-injected animals (15.62±0.93 vs. 19.71±4.25, $p=0.031$) as shown in FIG. 21. This indicates improvement of diastolic dysfunction in CDC-derived exosomes-injected HFpEF rats compared to placebo animals. Although EF did not change between CDC-derived exosomes and PBS-treated rats (68.42±2.14 vs. 69.12±6.21, $p=0.161$) as shown in FIG. 22, Kaplan-Meier survival analysis clearly showed a trend towards decreased mortality in CDC-derived exosomes-treated rats compared to PBS-injected animals (4/17=23.5% vs. 4/9=44.4%, Log rank 0.176) as shown in FIG. 23.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of cardiosphere derived cells, the use of alternative sources such as cells derived directly from heart biopsies (explant-derived cells), or from self-assembling clusters of heart-derived cells (cardiospheres), method of isolating, characterizing or altering such cells, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of treating heart failure with preserved ejection fraction, comprising:
administering a therapeutically effective amount of a composition comprising a plurality of exosomes isolated from cardiosphere-derived cells (CDCs) grown in serum-free media and essentially free of non-exosome components to a subject in need of treatment for heart failure with preserved ejection fraction (HFpEF), thereby treating HFpEF in the subject, wherein treating HFpEF comprises a reduction in fibrosis and/or inflammation.

2. The method of claim 1, wherein the plurality of exosomes comprise exosomes with a diameter of about 90 nm to about 200 nm and are CD81+, CD63+, or both.

3. The method of claim 1, wherein treating HFpEF comprises an improvement in cardiac performance.

4. The method of claim 3, wherein the improvement in cardiac performance comprises an improvement in early-to-late ventricular filling (E/A) ratio, left ventricle (LV) relaxation, LV end-diastolic pressure and/or lung congestion.

5. The method of claim 3, wherein the improvement in cardiac performance comprises a reduction in Tau and/or end-diastolic pressure volume relationship.

6. The method of claim 1, wherein administering a therapeutically effective amount of a composition comprising a plurality of exosomes to the subject is primary therapy.

7. The method of claim 1, wherein administering a therapeutically effective amount of a composition comprising a plurality of exosomes to the subject is adjunctive to standard therapy for heart failure.

* * * * *